(12) United States Patent
Dai et al.

(10) Patent No.: US 9,905,774 B2
(45) Date of Patent: *Feb. 27, 2018

(54) ORGANIC ELECTRONIC MATERIAL

(71) Applicants: GUANGDONG AGLAIA OPTOELECTRONIC MATERIALS CO., LTD, Foshan, Guangdong (CN); BEIJING AGLAIA TECHNOLOGY DEVELOPMENT CO., LTD, Beijing (CN)

(72) Inventors: Lei Dai, Beijing (CN); Jinhai Huang, Beijing (CN); Jinxin Chen, Foshan (CN); Lifei Cai, Beijing (CN)

(73) Assignees: GUANGDONG AGLAIA OPTOELECTRONIC MATERIALS CO., LTD, Foshan (CN); BEIJING AGLAIA TECHNOLOGY DEVELOPMENT CO., LTD, Beijing (CN)

( * ) Notice: Subject to any disclaimer, the term of this patent is extended or adjusted under 35 U.S.C. 154(b) by 588 days.

This patent is subject to a terminal disclaimer.

(21) Appl. No.: 14/404,604

(22) PCT Filed: May 26, 2013

(86) PCT No.: PCT/CN2013/076236
§ 371 (c)(1),
(2) Date: Nov. 28, 2014

(87) PCT Pub. No.: WO2013/178041
PCT Pub. Date: Dec. 5, 2013

(65) Prior Publication Data
US 2015/0108448 A1    Apr. 23, 2015

(30) Foreign Application Priority Data

May 30, 2012  (CN) .......................... 2012 1 0174028
May 17, 2013  (CN) .......................... 2013 1 0185347

(51) Int. Cl.
| | | |
|---|---|---|
| *H01L 51/00* | (2006.01) |
| *H01L 51/50* | (2006.01) |
| *C09K 11/06* | (2006.01) |
| *C07C 13/567* | (2006.01) |
| *C07C 13/66* | (2006.01) |
| *C07C 13/72* | (2006.01) |
| *C07C 15/60* | (2006.01) |
| *C07C 211/54* | (2006.01) |
| *C07C 211/58* | (2006.01) |

(52) U.S. Cl.
CPC ........ *H01L 51/0058* (2013.01); *C07C 13/567* (2013.01); *C07C 13/66* (2013.01); *C07C 13/72* (2013.01); *C07C 15/60* (2013.01); *C07C 211/54* (2013.01); *C07C 211/58* (2013.01); *C09K 11/06* (2013.01); *H01L 51/5012* (2013.01); *C07C 2603/18* (2017.05); *C07C 2603/24* (2017.05);

(Continued)

(58) Field of Classification Search
CPC ....... C07C 13/567; C07C 13/66; C07C 13/72; C07C 15/60; C07C 211/54; C07C 211/58; C07C 2603/18; C07C 2603/24; C07C 2603/26; C07C 2603/40; C07C 2603/50; C07C 2063/94; C09K 11/06; C09K 2211/1007; C09K 2211/1011; C09K 2211/1029; H01L 51/0058; H01L 51/5012; H01L 51/5056; H01L 51/5072; H01L 51/5088; H01L 51/5092; H01L 51/5096; Y02E 10/549; Y02P 70/521
See application file for complete search history.

(56) References Cited

U.S. PATENT DOCUMENTS 6,534,199 B1 *  3/2003  Hosokawa .......... H01L 51/0052
                                                      252/301.16
6,730,419 B2    5/2004  Kim et al.
(Continued)

FOREIGN PATENT DOCUMENTS

CN        1407053 A     4/2003
CN      101143830 A     3/2008
(Continued)

OTHER PUBLICATIONS

Machine translation for JP 2007-227717 A (publication date Sep. 2007).*

(Continued)

*Primary Examiner* — Dawn Garrett
(74) *Attorney, Agent, or Firm* — Maschoff Brennan

(57) ABSTRACT

The present invention discloses an "organic electronic material", belonging to the organic light-emitting device (OLED) display materials field. The organic electronic material in the present invention has a structural formula (I). The OLED made by this kind of organic light-emitting material has the advantages of excellent light-emitting efficiency, excellent color purity and long service lifetime.

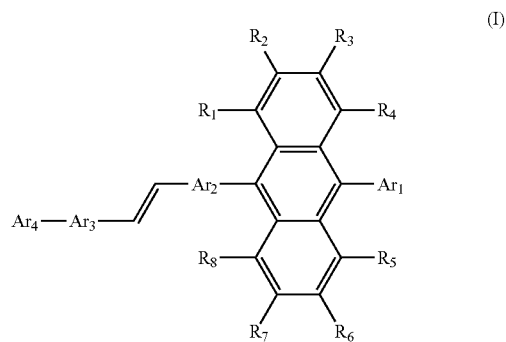

14 Claims, 1 Drawing Sheet

(52) U.S. Cl.
CPC ...... *C07C 2603/26* (2017.05); *C07C 2603/40* (2017.05); *C07C 2603/50* (2017.05); *C07C 2603/94* (2017.05); *C09K 2211/1007* (2013.01); *C09K 2211/1011* (2013.01); *C09K 2211/1029* (2013.01); *Y02E 10/549* (2013.01); *Y02P 70/521* (2015.11)

(56) References Cited

U.S. PATENT DOCUMENTS

| | | | |
|---|---|---|---|
| 6,803,120 B2* | 10/2004 | Fukuoka | C09K 11/06 313/504 |
| 7,651,787 B2* | 1/2010 | Seo | H01L 51/0052 313/504 |
| 2006/0257687 A1* | 11/2006 | Hosokawa | B32B 9/00 428/690 |
| 2013/0113367 A1* | 5/2013 | Jung | C07D 401/14 313/504 |
| 2014/0027721 A1* | 1/2014 | Kim | C07C 211/61 257/40 |

FOREIGN PATENT DOCUMENTS

| | | | |
|---|---|---|---|
| CN | 101698795 A | | 4/2010 |
| EP | 1094101 A2 | | 4/2001 |
| EP | 2182038 A1 | * | 5/2010 |
| JP | 2002-093582 A | | 3/2002 |
| JP | 2004-231563 A | * | 8/2004 |
| JP | 2007-227717 A | | 9/2007 |
| WO | WO 2011/105700 A1 | * | 9/2011 |

OTHER PUBLICATIONS

H. Huang et al., "Solution-processable 1,3,5-tri(9-anthracene)-benzene cored propeller-shaped materials with high Tg for blue organic light-emitting diodes" Organic Electronics, vol. 12, Issue 10, Oct. 2011, pp. 1716-1723.

\* cited by examiner

ORGANIC ELECTRONIC MATERIAL

TECHNICAL FIELD

This invention relates to a new type of organic blue light-emitting OLED produced by organic electronic material, which belongs to OLED display technology field.

BACKGROUND ART

OLED, as a new type of display technology, has unique advantages such as self-illumination, wide viewing angle, low power consumption, high efficiency, thin, rich colors, fast response, extensive application temperature range, low driving voltage, applicable for flexible and transparent display panel, and environmental friendliness, etc. Therefore, OLED technology can be applied to flat panel displays and new generation of lighting, or can be used as backlight of LCD.

OLED is a device made through spin-coating or depositing organic material layers between two electrodes. A classic three-layer OLED comprises a hole transport layer, a light emitting layer and an electron transport layer. The holes injected from the anode and hopping through the hole transport layer, and the electrons injected from the cathode and hopping through the electron transport layer combine to form excitons in the light emitting layer and emit light. By changing the materials of the light emitting layer, the OLED can emit red, green and blue light. Therefore, stable, efficient organic light-emitting materials with pure colors play an important role in the application and promotion of OLEDs, and are urgently needed for the application and promotion of large area panel display in OLEDs.

Among three primary colors (red, blue, green), the red and green emitting materials have made great development, which also meet the market demands of the panels. There are a series of commercially available materials for the blue light emission, such as 4,4'-bis(2,2'-diphenyl vinyl)-1,1'-biphenyl (DPVBi) compounds produced by Idemitsu are widely used in the early period. The devices made by this type of compounds have high efficiency, but these materials often have poor stability, and even worse, this type of compounds often emit sky-blue light, with $CIE_y > 0.15$. Therefore, its poor stability and impure color greatly restrict the application of this type of compounds in the full-color display devices. Some other blue-light materials, such as ADN and tetra-butyl perylene made by Kodak, have relatively poor luminous efficiency and cannot be widely used.

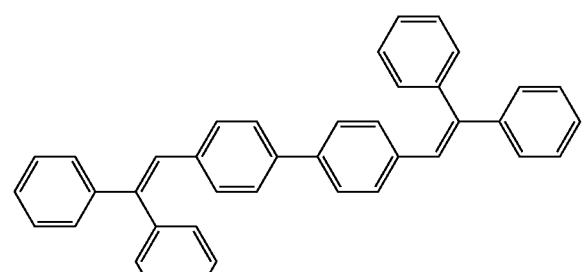

(DPVBi)

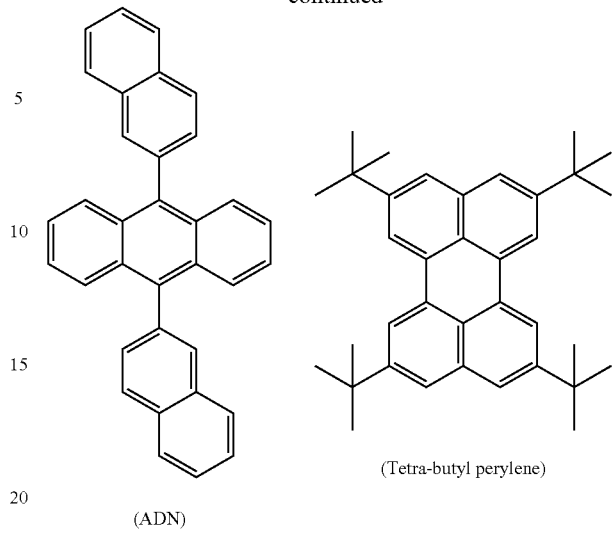

(ADN)　(Tetra-butyl perylene)

SUMMARY OF THE INVENTION

In the present invention, a kind of blue light-emitting OLED with good electroluminescent efficiency, excellent color purity and long lifetime is provided to overcome the deficiencies of the above devices.

An organic light-emitting device comprises an anode, a cathode, and one or more organic layers, wherein the said organic layer contains at least one compound having the formula I:

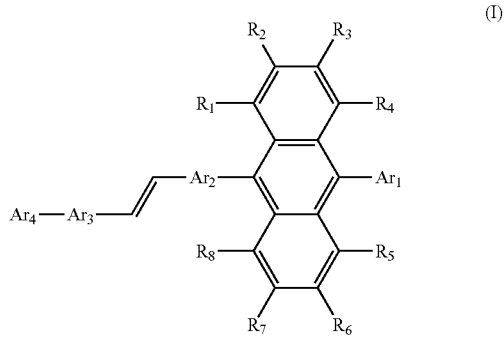

(I)

Wherein, $R_1$-$R_8$ independently represent hydrogen, deuterium, halogen, cyano, nitro, C1-C8 alkyl, C1-C8 alkoxy, C6-C30 substituted or unsubstituted aryl, C3-C30 substituted or unsubstituted heteroaryl containing one or more heteroatoms, C2-C8 substituted or unsubstituted alkenyl, C2-C8 substituted or unsubstituted alkynyl, wherein, $Ar_1$-$Ar_4$ represent independently C6-C60 substituted or unsubstituted aryl, C3-C60 substituted or unsubstituted heteroaryl containing one or more heteroatoms, triaryl (C6-C30) amine.

Preferably, wherein $R_1$-$R_8$ independently represent hydrogen, halogen, cyano, nitro, C1-C8 alkyl, C1-C8 alkoxy, C2-C8 substituted or unsubstituted alkenyl, C2-C8 substituted or unsubstituted alkynyl, C1-C4 alkyl substituted or unsubstituted phenyl, C1-C4 alkyl substituted or unsubstituted naphthyl; $Ar_1$-$Ar_4$ independently represent C1-C4 alkyl or C6-C30 aryl substituted phenyl, C1-C4 alkyl or C6-C30 aryl substituted naphthyl, phenyl, naphthyl, N-aryl (C6-C30) or C1-C4 alkyl-substituted carbazolyl, dibenzothiophenyl, dibenzofuranyl, anthryl, phenanthryl, pyrenyl, perylenyl, fluoranthenyl, (9,9-di-alkyl) fluorenyl, (9,9-dialkyl-substituted or unsubstituted aryl) fluorenyl, 9,9-spiro-fluorenyl.

Preferably, wherein $R_1$-$R_8$ independently represent hydrogen, halogen, C1-C4 alkyl, C1-C4 alkyl substituted or unsubstituted phenyl, C1-C4 alkyl substituted or unsubstituted naphthyl; preferably, $Ar_1$-$Ar_4$ independently represent phenyl, tolyl, t-butyl phenyl, naphthyl, methyl naphthalene, biphenyl, diphenyl phenyl, naphthyl phenyl, diphenyl-biphenyl, biaryl amine pheny, N-phenyl-carbazolyl, (9,9-di-alkyl) fluorenyl, (9,9-dialkyl-substituted or unsubstituted phenyl) fluorenyl, 9,9-spiro-fluorenyl.

Preferably, wherein, $R_1$, $R_4$, $R_5$, $R_8$ are hydrogen, $R_2$, $R_3$, $R_6$, $R_7$ independently represent hydrogen, fluorine, methyl, ethyl, propyl, isopropyl, tert-butyl, phenyl, naphthyl; $Ar_1$-$Ar_4$ independently represent phenyl, tolyl, naphthyl, methyl naphthyl, biphenyl, diphenyl phenyl, naphthyl phenyl, diphenyl-biphenyl, (9,9-di-alkyl) fluorenyl, (9,9-dimethyl-substituted or unsubstituted phenyl) fluorenyl, 9,9-spiro-fluorenyl.

Preferably, wherein $Ar_2$, $Ar_3$, $Ar_4$ independently represent phenyl, naphthyl, biphenyl, $Ar_1$ is phenyl, naphthyl, biphenyl, diphenyl phenyl, naphthyl phenyl, diphenyl-biphenyl, (9,9-di-alkyl) fluorenyl, (9-tolyl, 9'-phenyl) fluorenyl, 9,9-spiro-fluorenyl.

Preferably, wherein $R_2$, $R_3$, $R_6$, $R_7$ are hydrogen, $Ar_2$, $Ar_3$, $Ar_4$ independently represent phenyl, naphthyl.

Preferably, the said compound with formula (I) is the compound with the following structures:

The said organic layers is one or more layers that may contain hole injection layer, hole transport layer, light emitting layer, hole blocking layer and electron transport layer. It should be particularly noted that, not all organic layers are necessary according to the needs.

The said hole transport layer, electron transport layer and/or light emitting layer may contain the compound with formula (I).

The said compound with formula (I) is located at the light emitting layer.

The OLED in the present invention comprises a light-emitting layer, and the emission wavelength is within the range of 380-740 nm, covering the entire white zone. Preferably, the emission is within the range of 380-550 nm, and more preferably in the blue region within the range of 440-490 nm.

The said light-emitting layer is a non-doped system or guest-host doped system composed of host material and guest material.

The said compound with formula (I) is host material and/or guest material.

In the doped system, the concentration of host material is 20-99.9% of the whole light emitting layer in weight, preferably 80-99%, more preferably 90-99%; while the concentration of guest material is 0.01-80% of the whole light emitting layer in weight, preferably 1-20%, more preferably 1-10%.

The total thickness of the organic layers of electronic device in the present invention is 1-1000 nm, preferably 1-500 nm, more preferably 50-300 nm.

The said organic layer can be formed as thin film by vacuum evaporating or spin coating.

As mentioned above, the said compound with formula (I) in the present invention is exemplified as follows, but not limited to the structures as below:

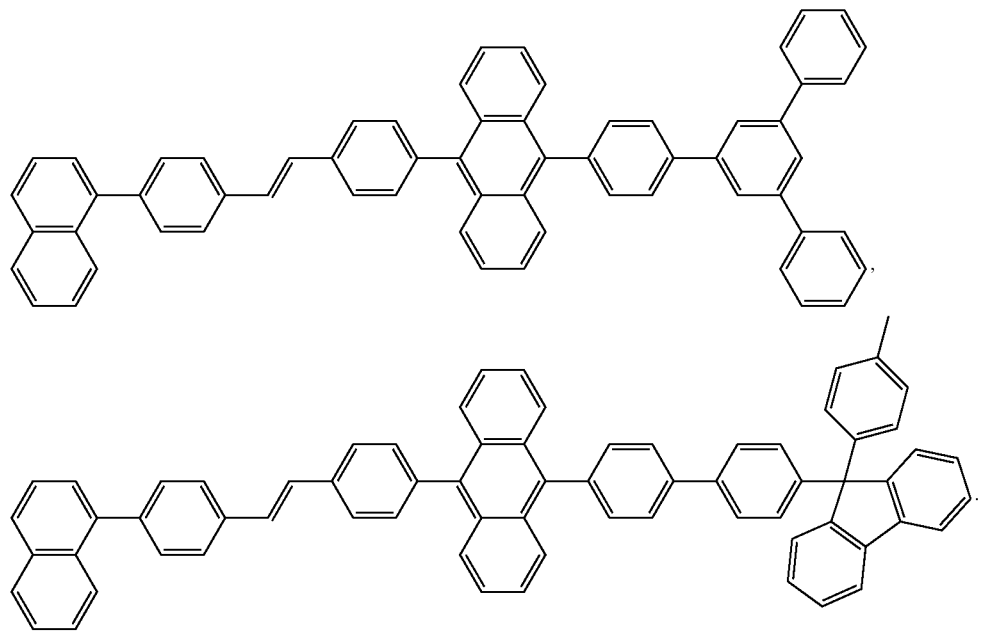

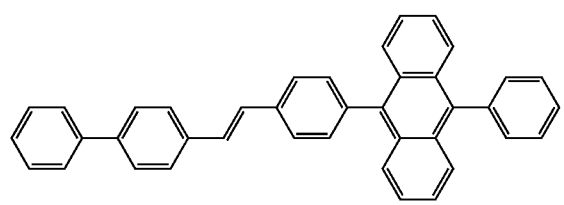
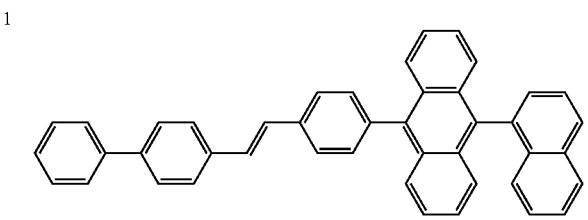
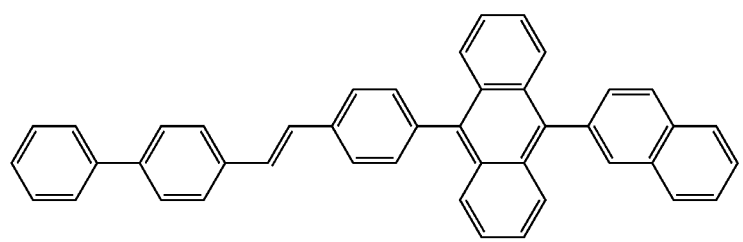
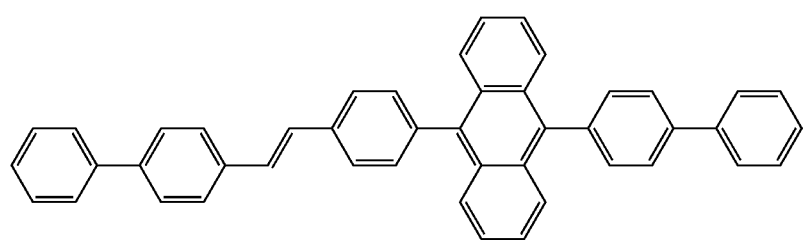
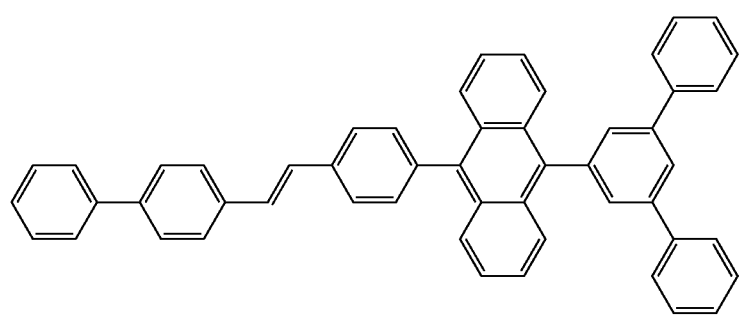
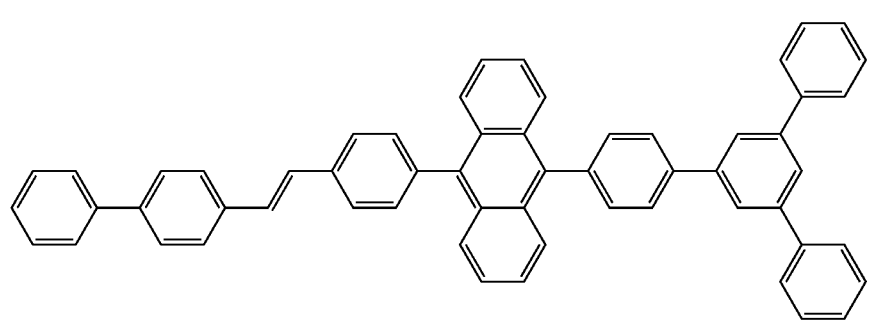
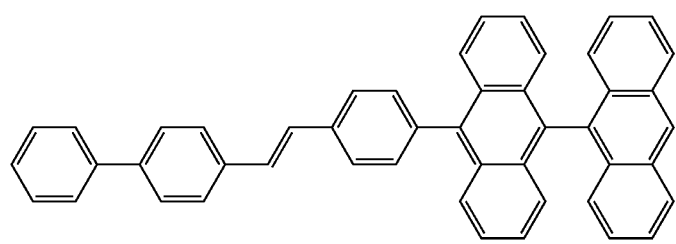 [SMILES: C(=C\c1ccc(-c2c3ccccc3c(-c3c4ccccc4cc4ccccc34)c3ccccc23)cc1)/c1ccc(-c2ccccc2)cc1]

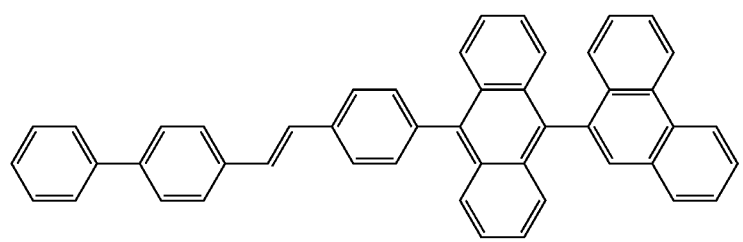
8
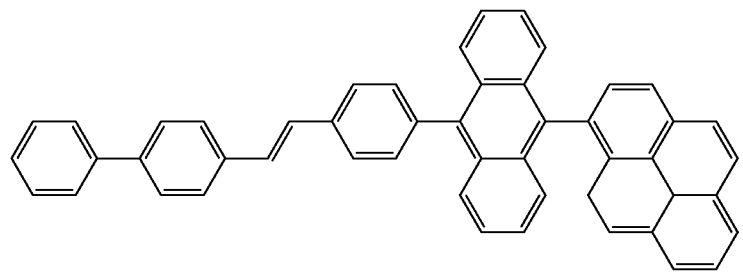
9
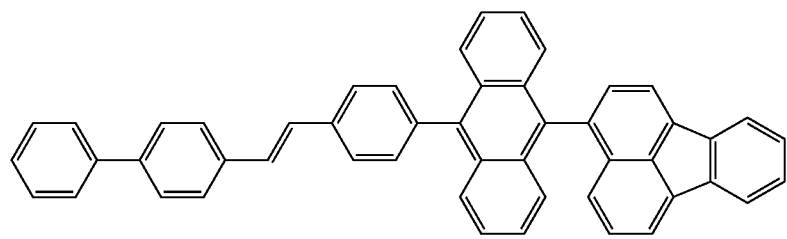
10
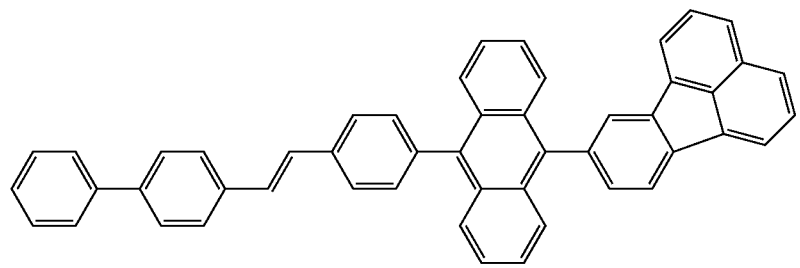
11
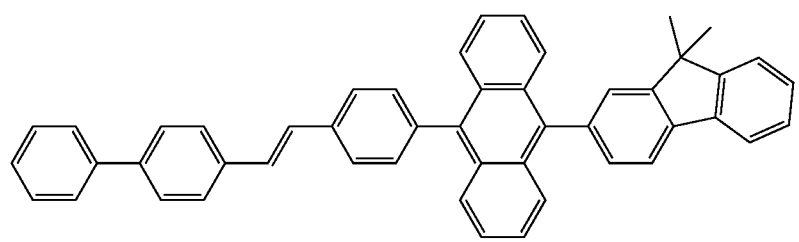
12
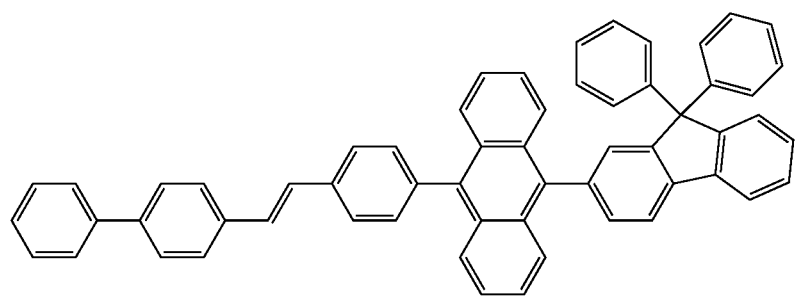
13

-continued
14
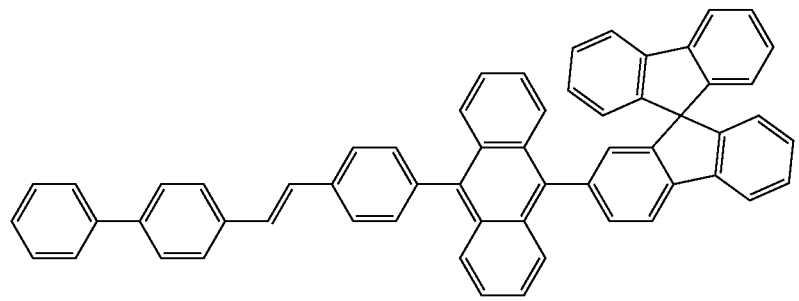
15
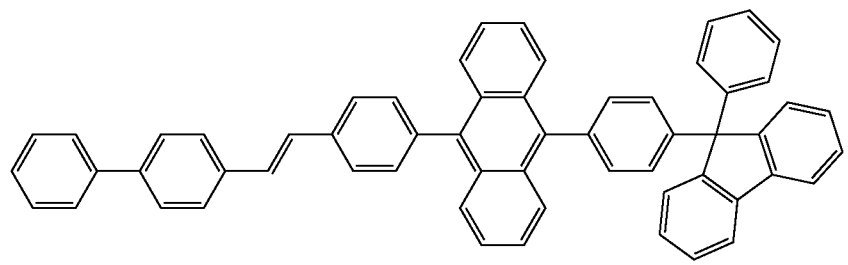
16
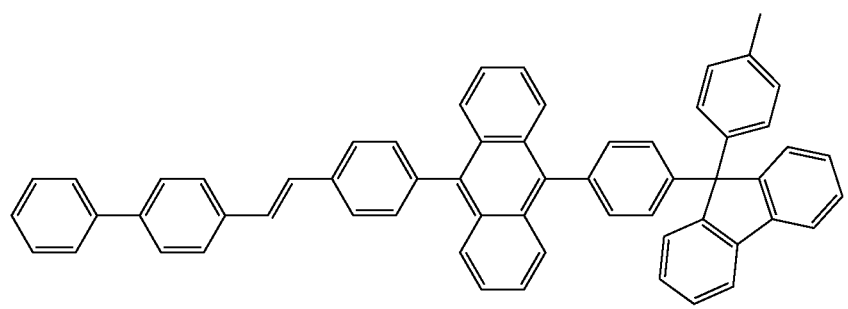
17
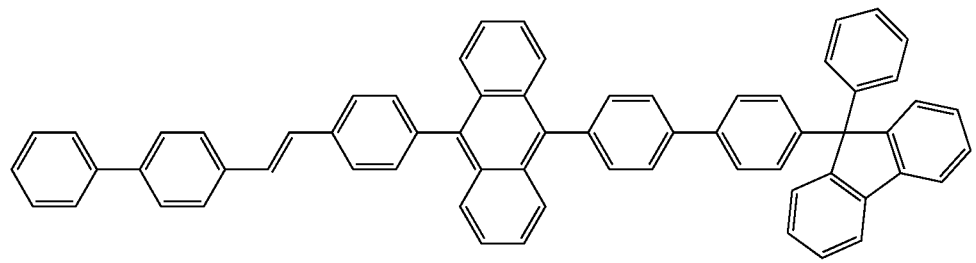
18
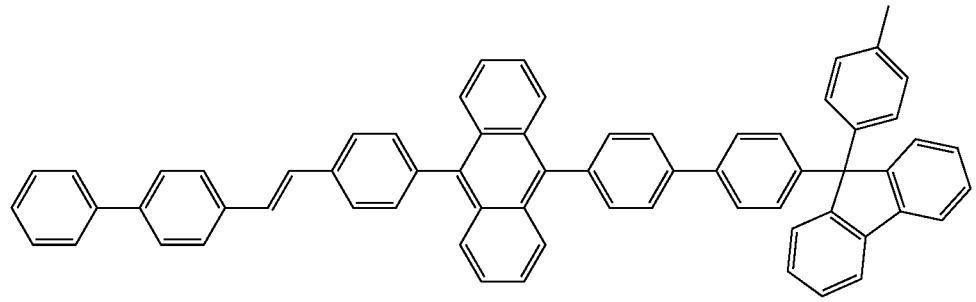

-continued
19
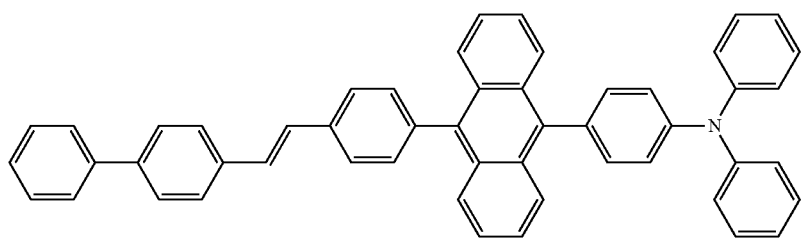
20
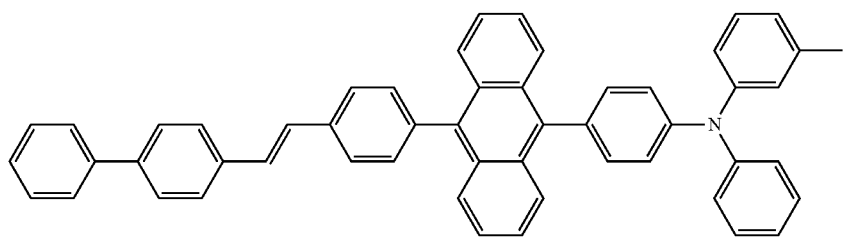
21
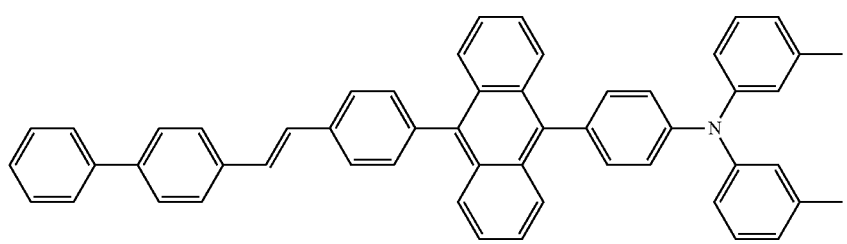
22
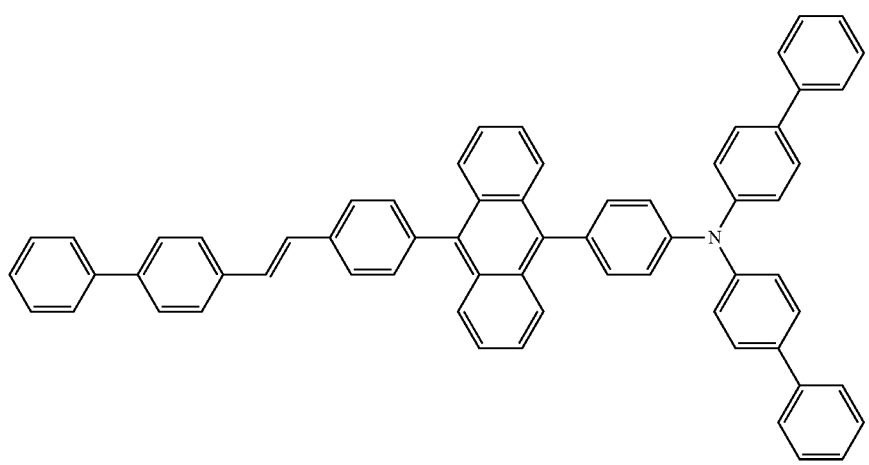
23
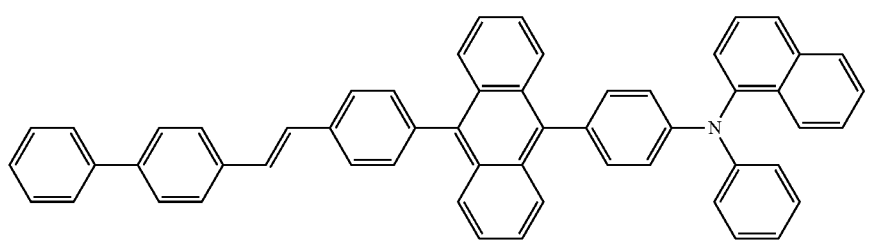

24
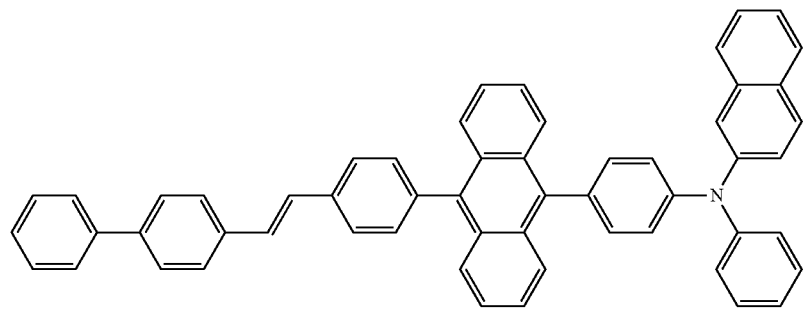
25
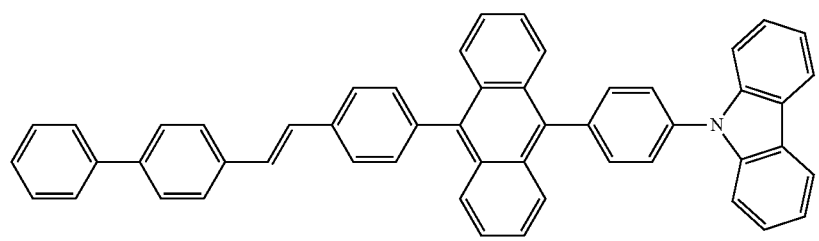
26
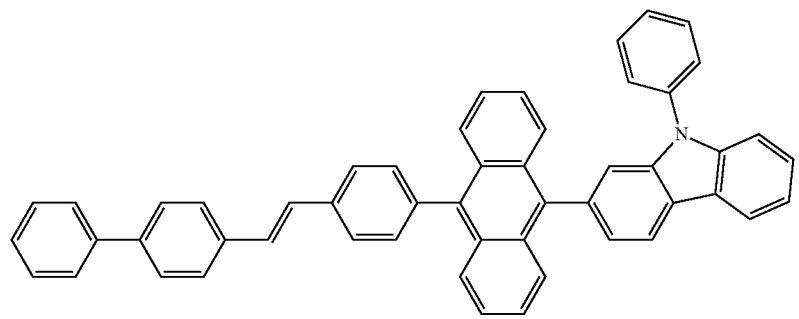
27 28
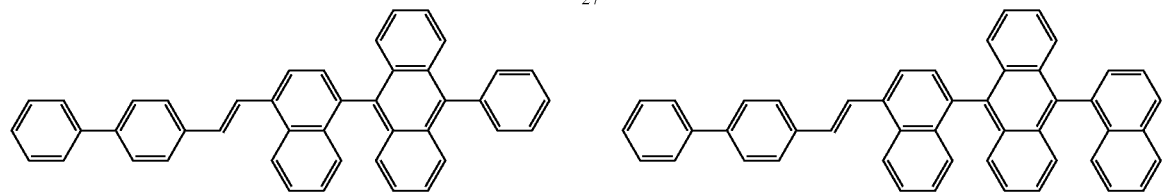
29
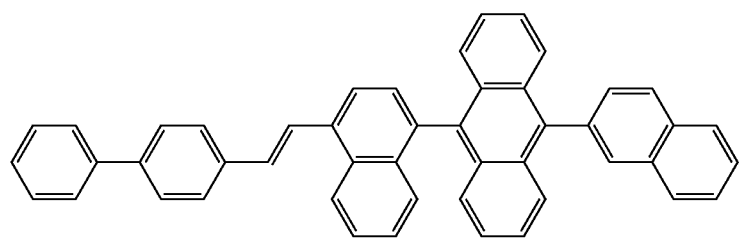
30
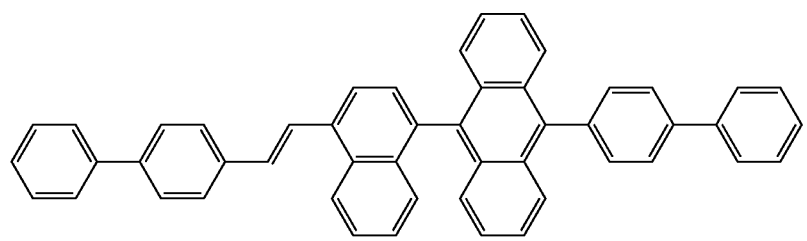

31
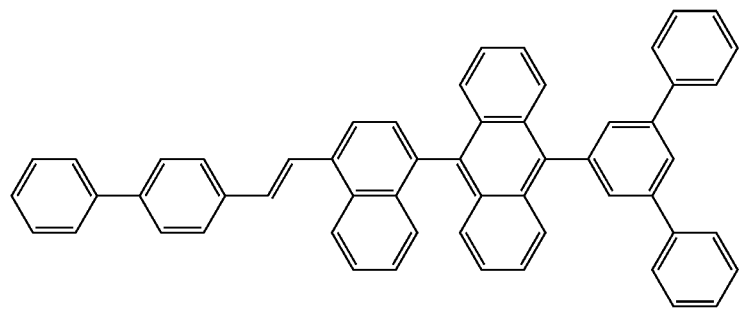 [SMILES: C(=C\c1ccc(-c2c3ccccc3c(-c3cc(-c4ccccc4)cc(-c4ccccc4)c3)c3ccccc23)c2ccccc12)/c1ccc(-c2ccccc2)cc1]
32
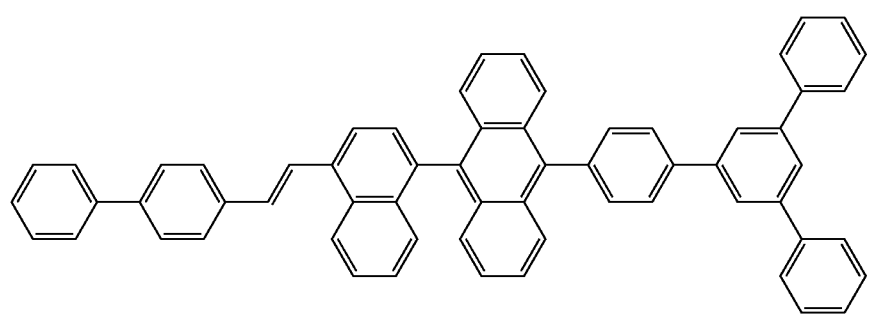
33 34
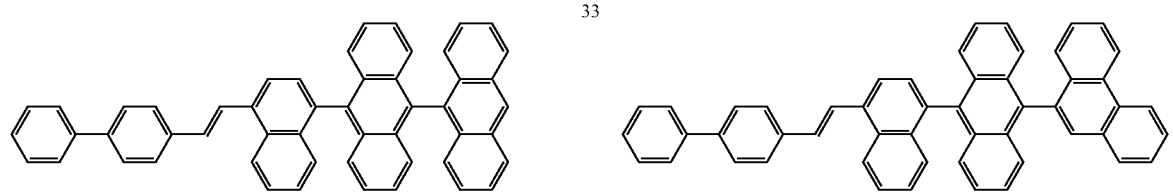
35
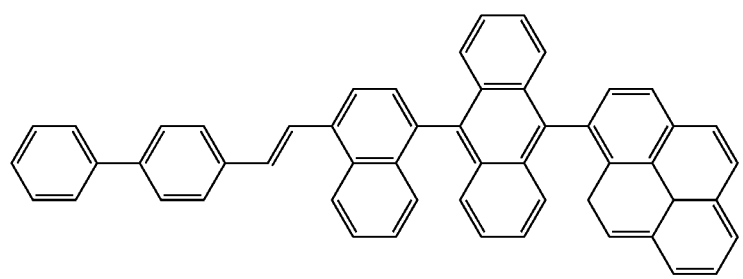
36
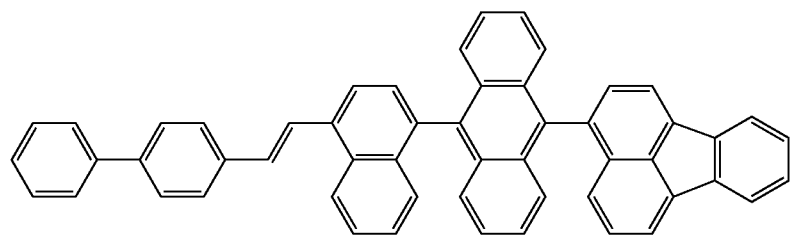
37
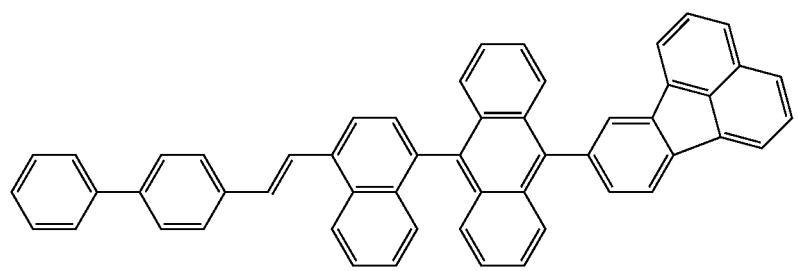

38
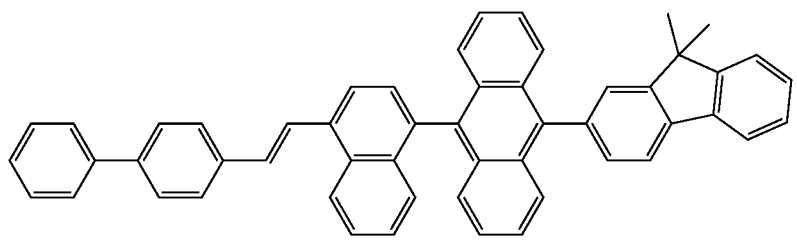 [SMILES: CC1(C)c2ccccc2-c2ccc(-c3c4ccccc4c(-c4ccc(/C=C/c5ccc(-c6ccccc6)cc5)c5ccccc45)c4ccccc34)cc21]
39
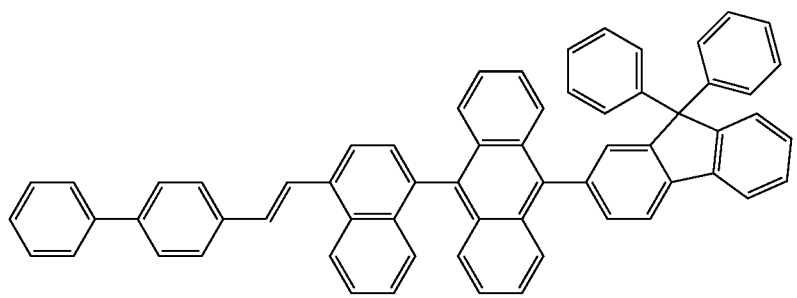
40
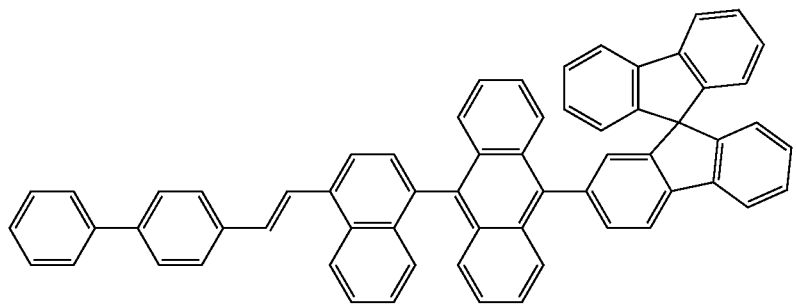
41
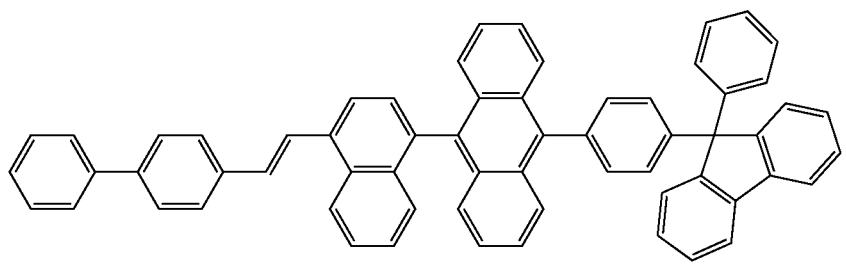
42
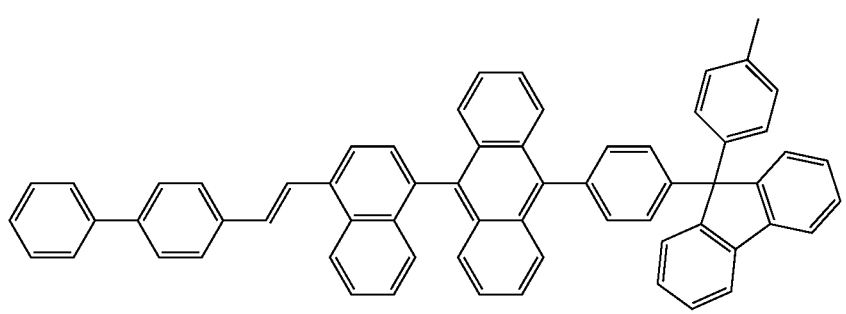

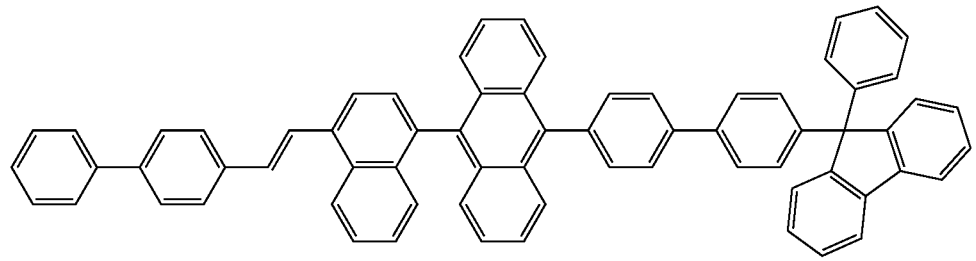
43
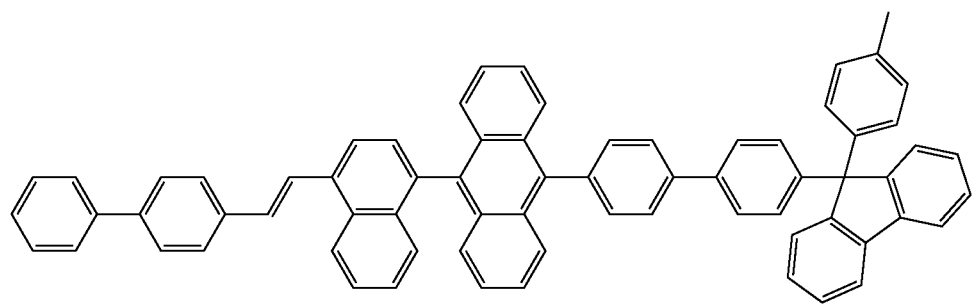
45
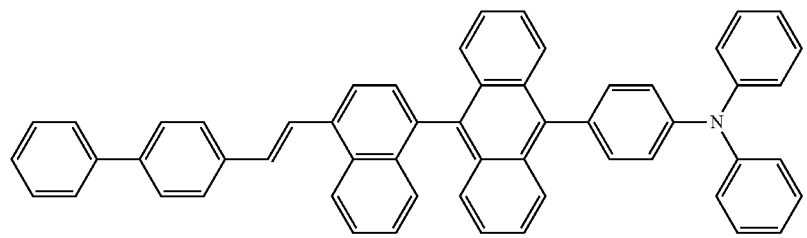
46
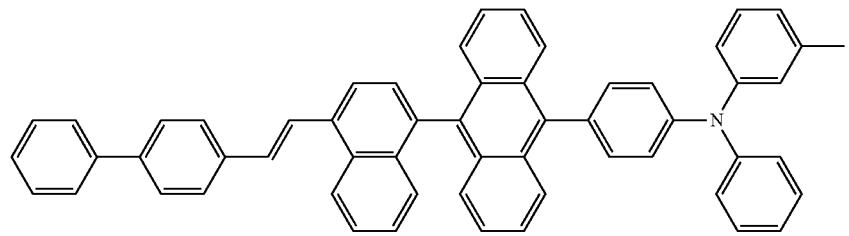
47
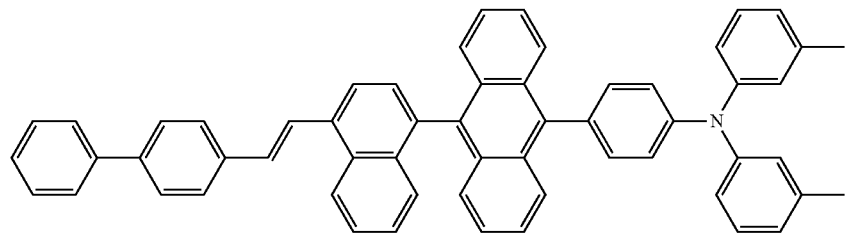

48
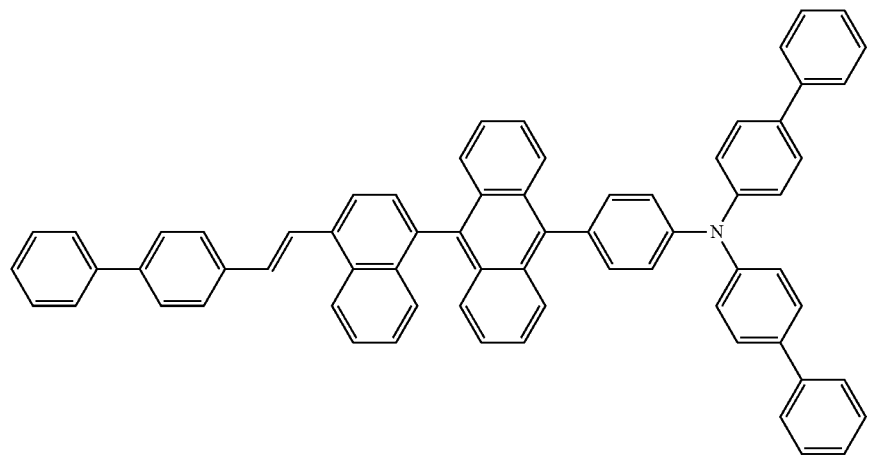
49
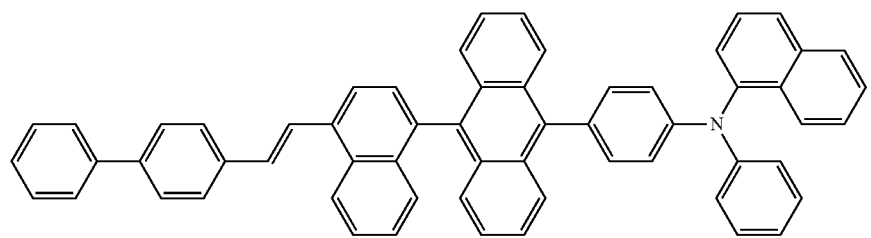
50
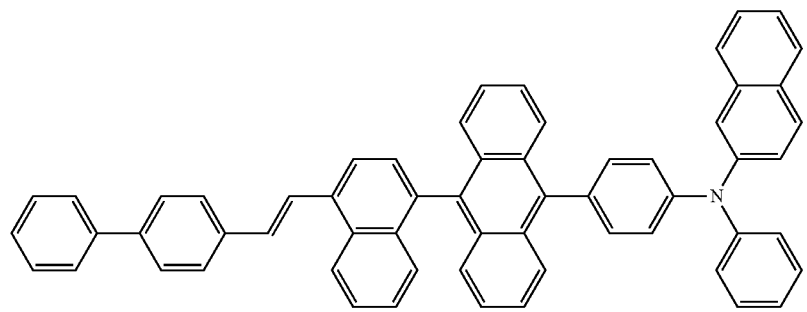
51
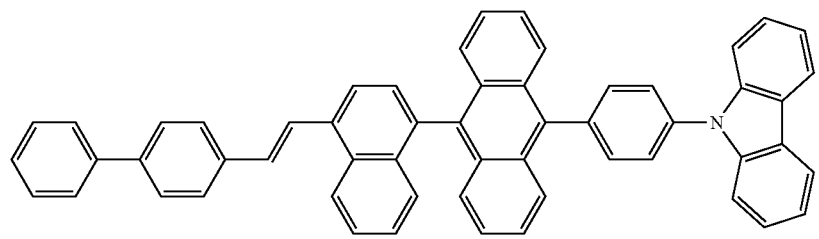
52
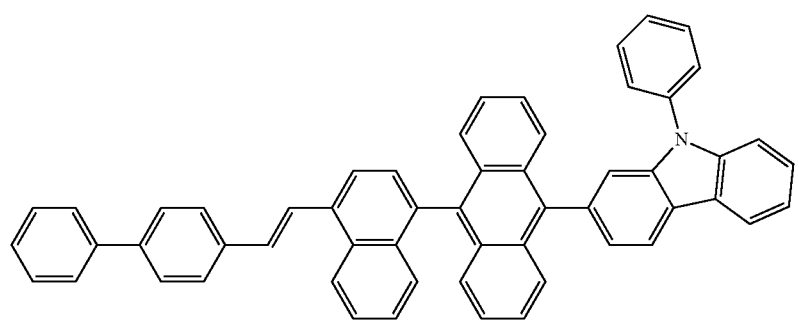

53
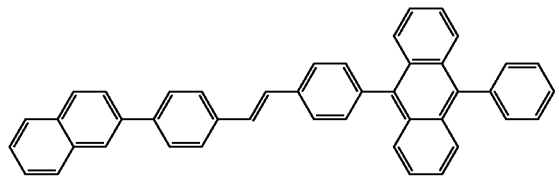
54
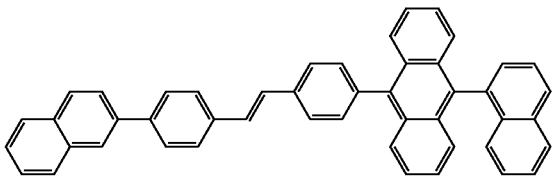
55
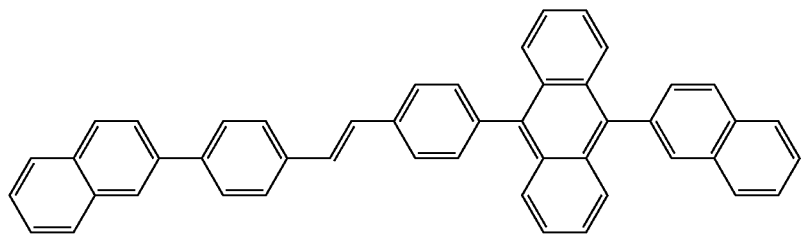 [SMILES: C(=C\c1ccc(-c2c3ccccc3c(-c3ccc4ccccc4c3)c3ccccc23)cc1)/c1ccc(-c2ccc3ccccc3c2)cc1]
56
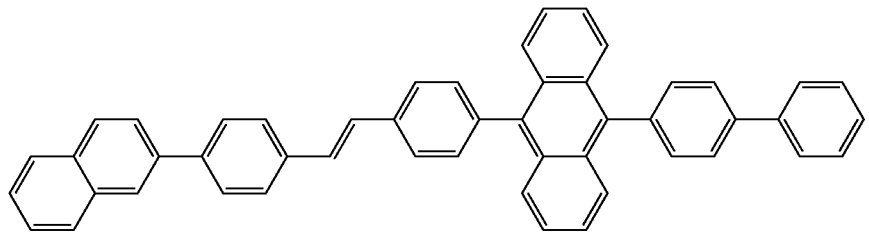
57
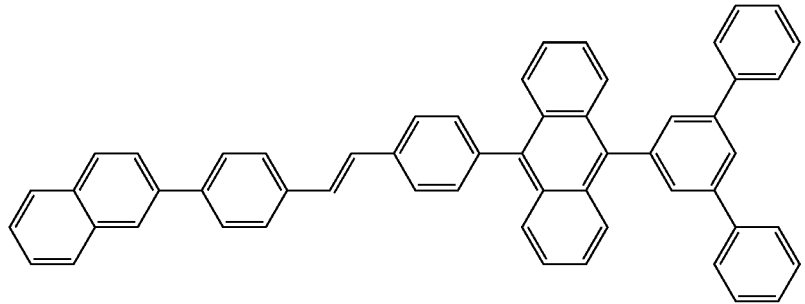
58
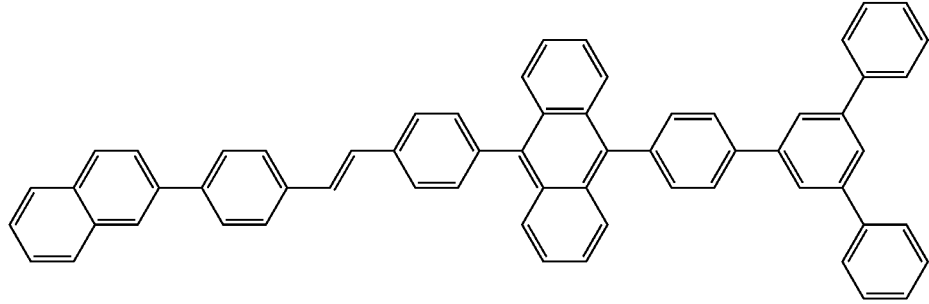
59
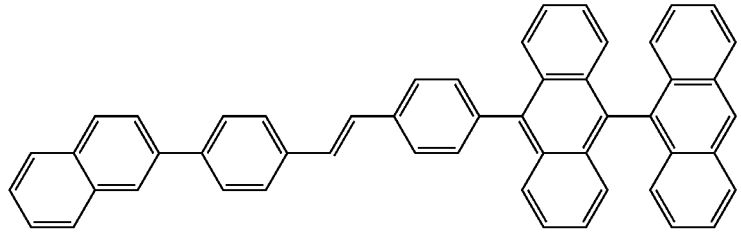

60
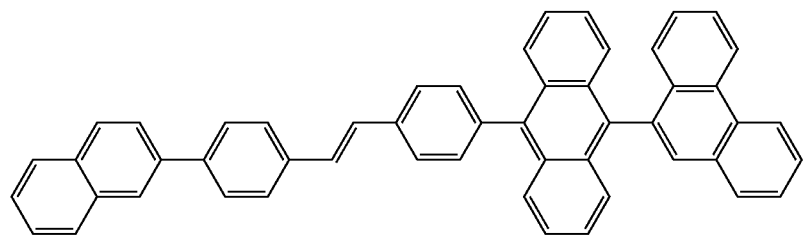
61
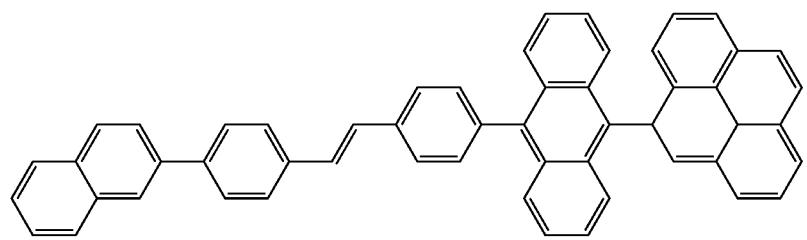
62
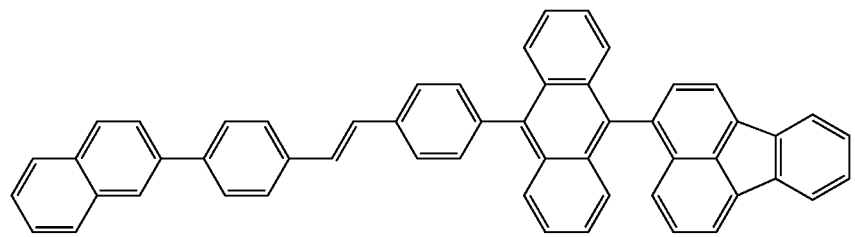
63
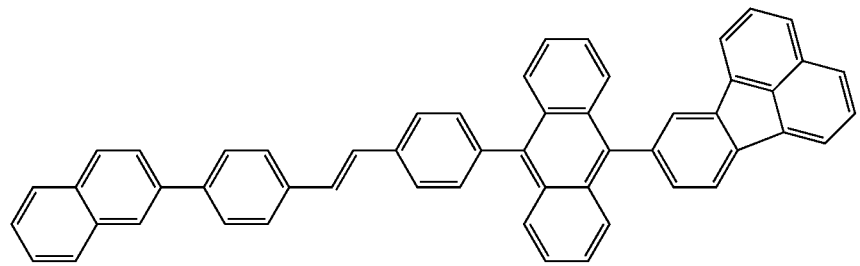
64
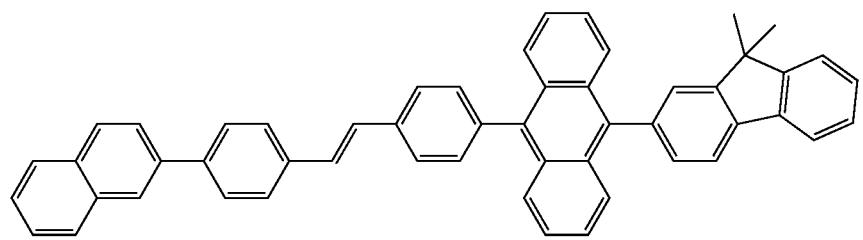
65
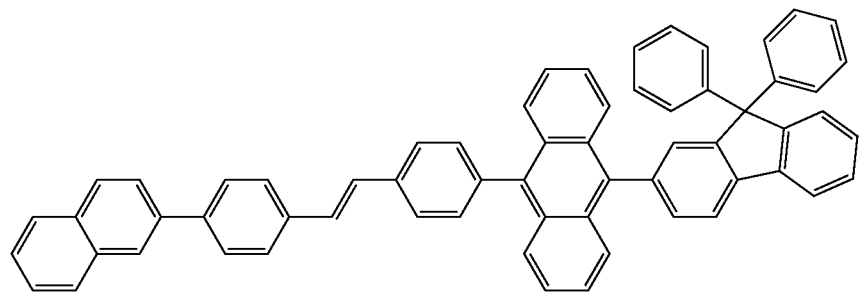

-continued
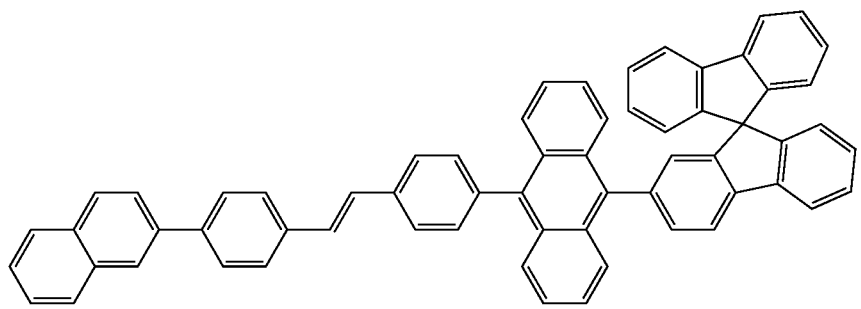
66
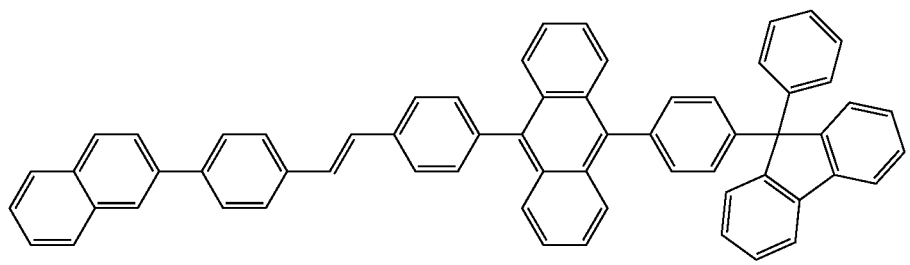
67
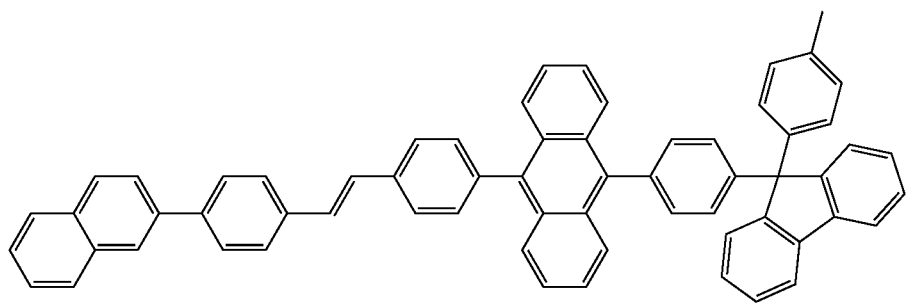
68
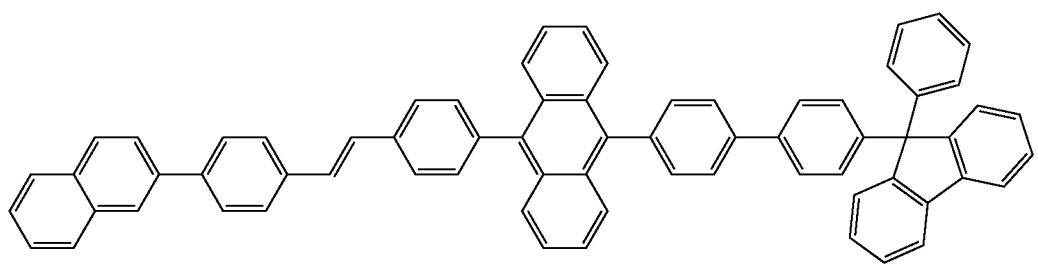
69
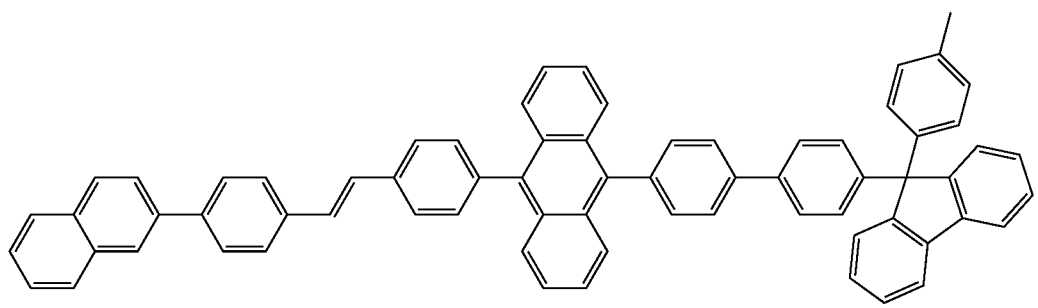
70

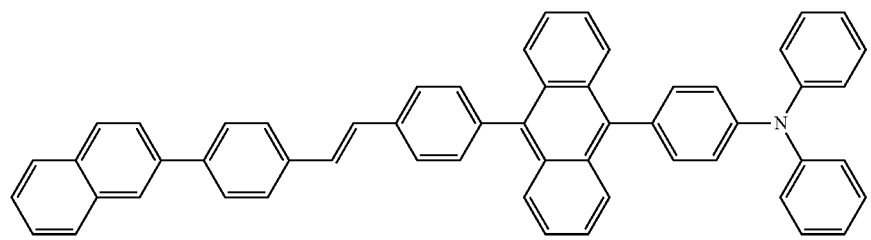
71
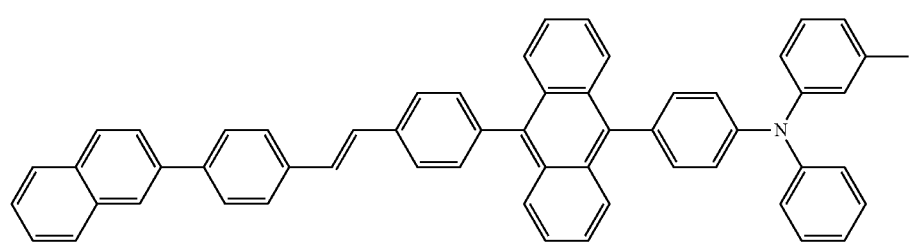
72
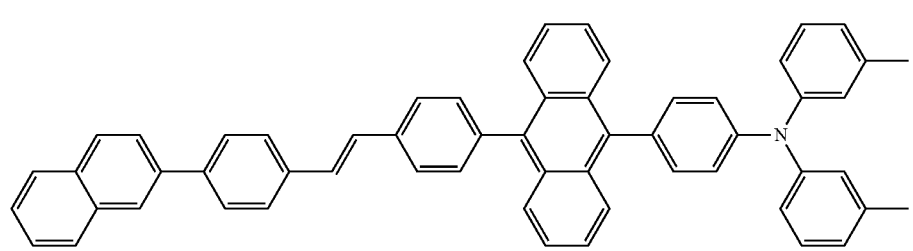
73
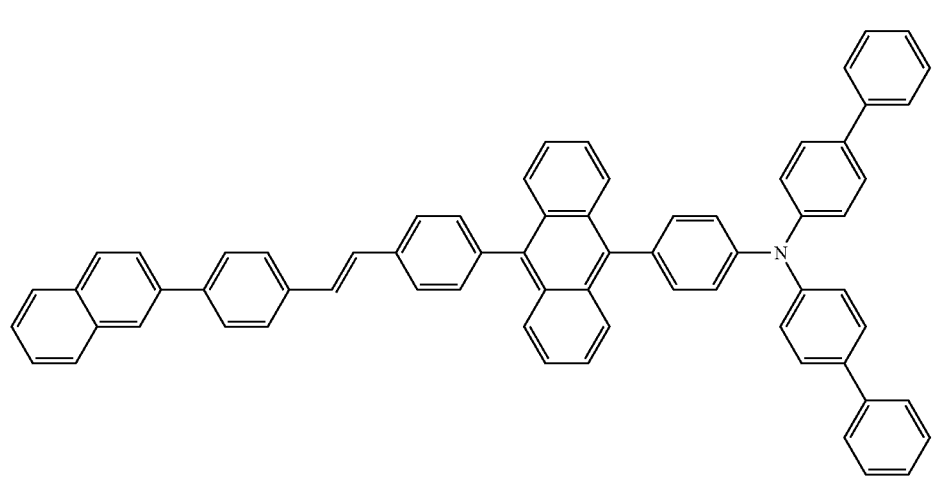
74
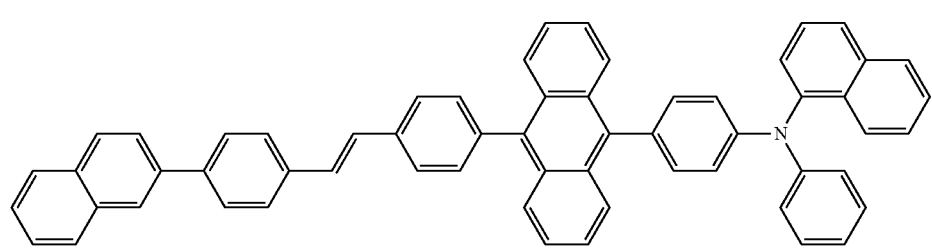
75

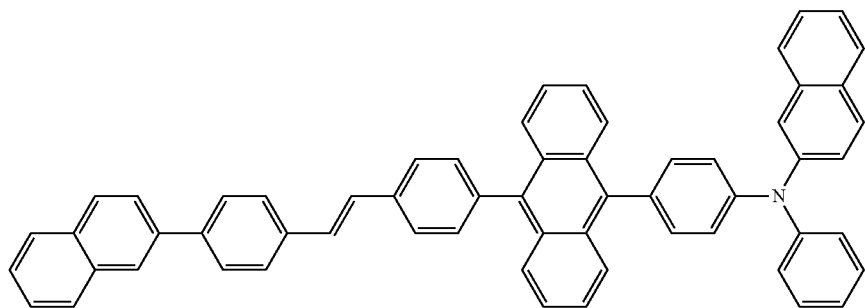
76
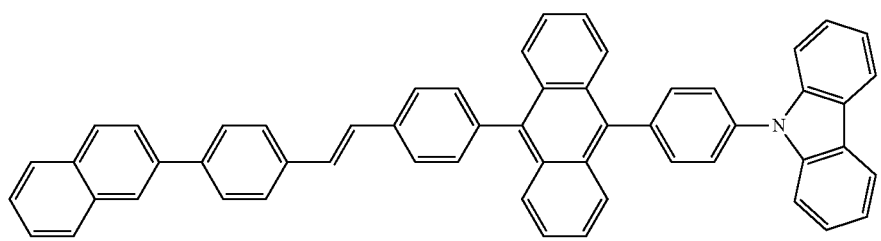
77
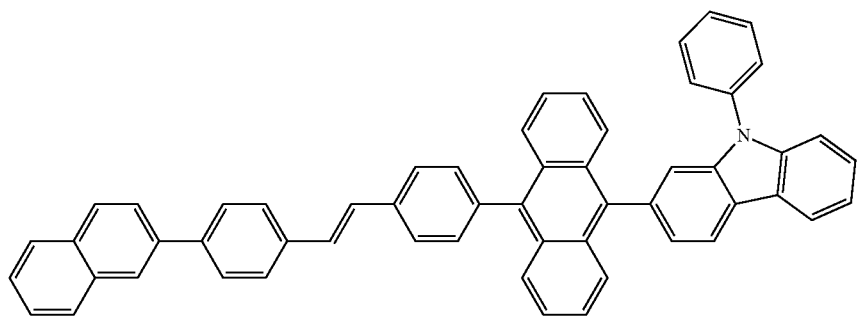
78
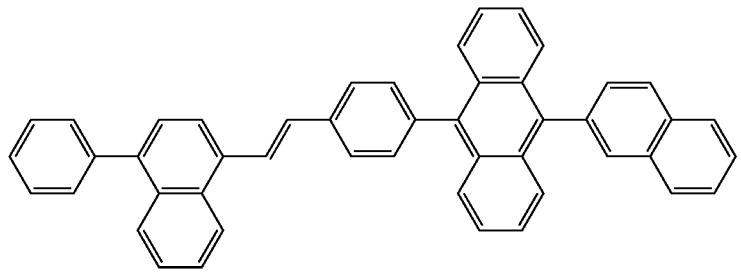
79
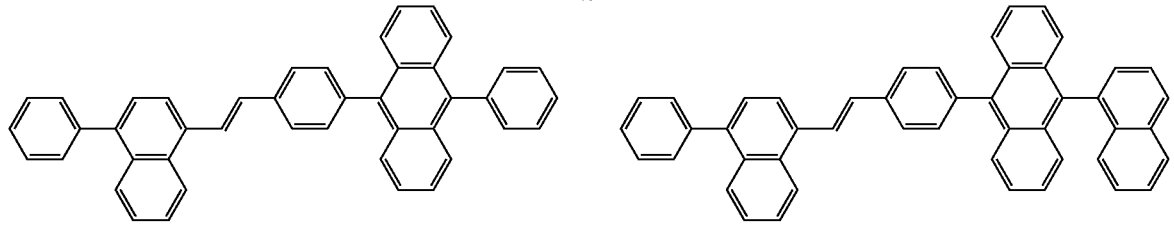
80
81

82
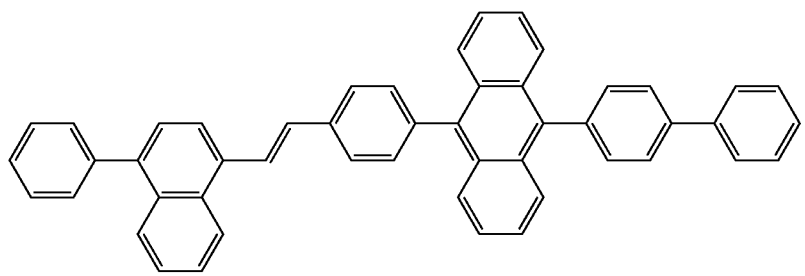
83
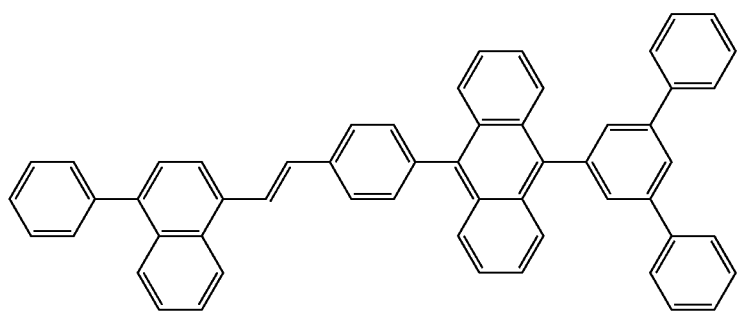
84
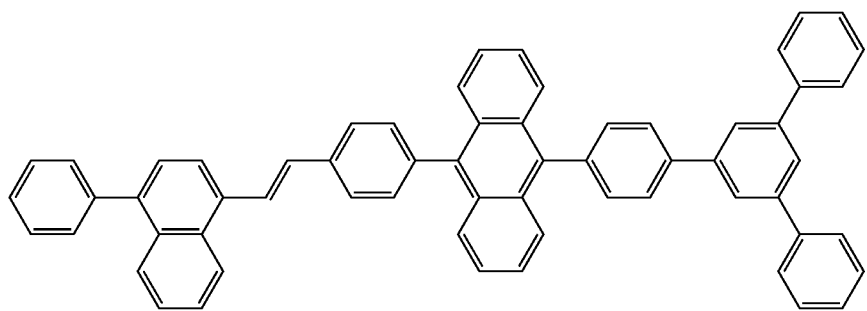
85
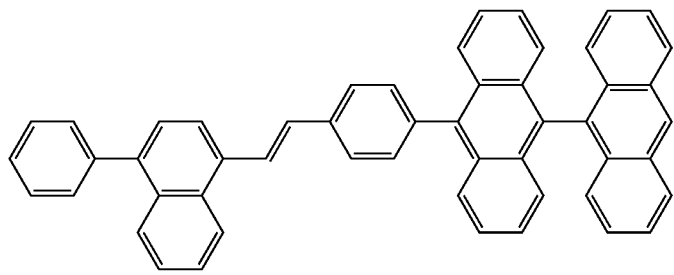 [SMILES: C(=C\c1ccc(-c2ccccc2)c2ccccc12)/c1ccc(-c2c3ccccc3c(-c3c4ccccc4cc4ccccc34)c3ccccc23)cc1]
86
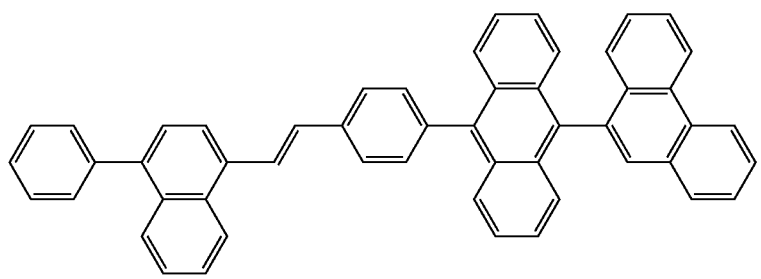

87
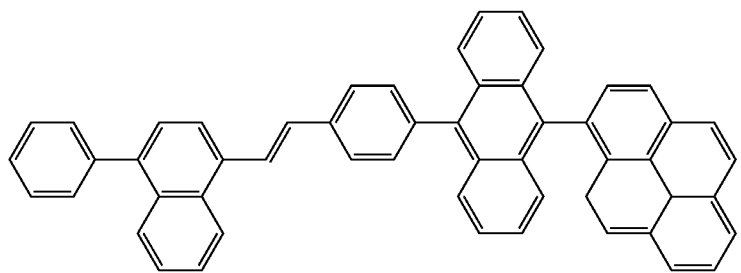
88
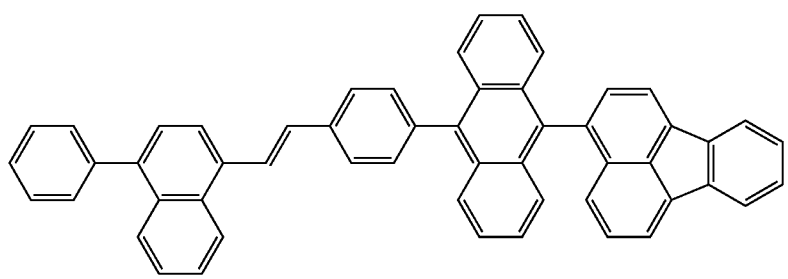
89
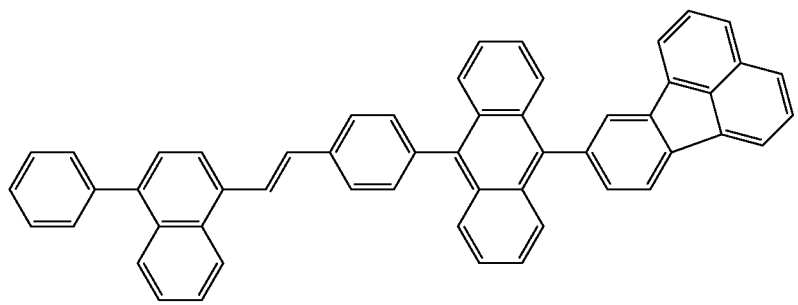
90
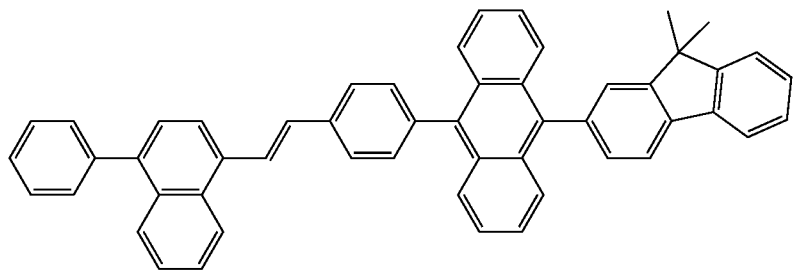
91
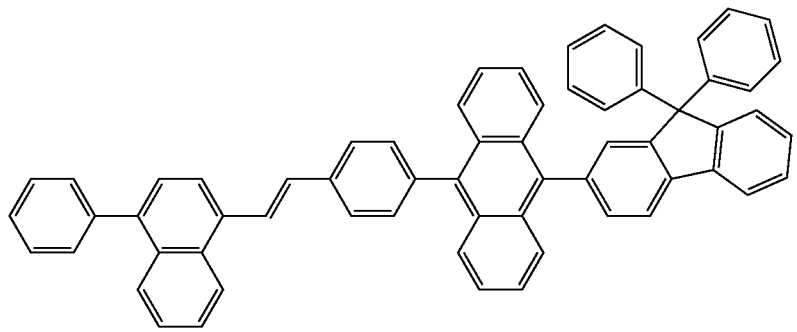

92
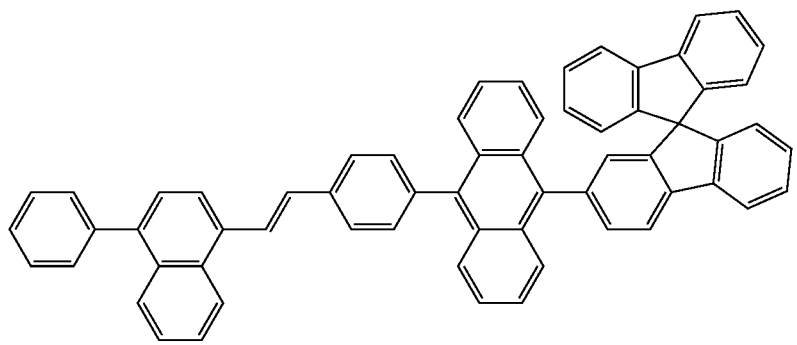
93
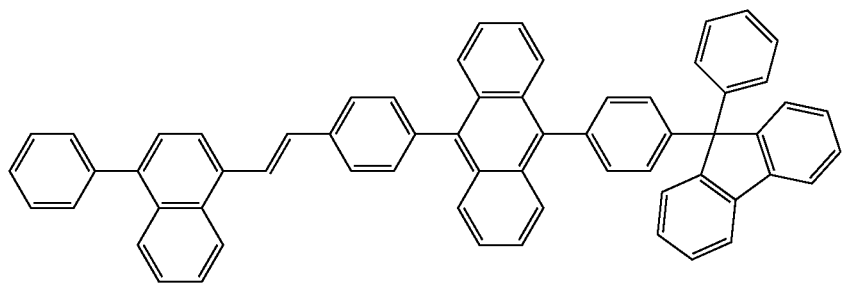
94
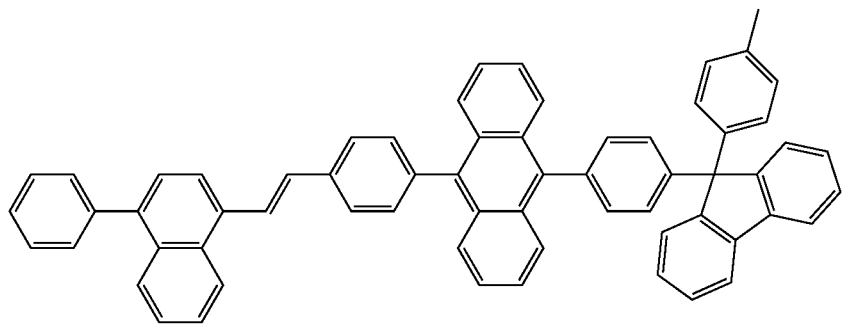
95
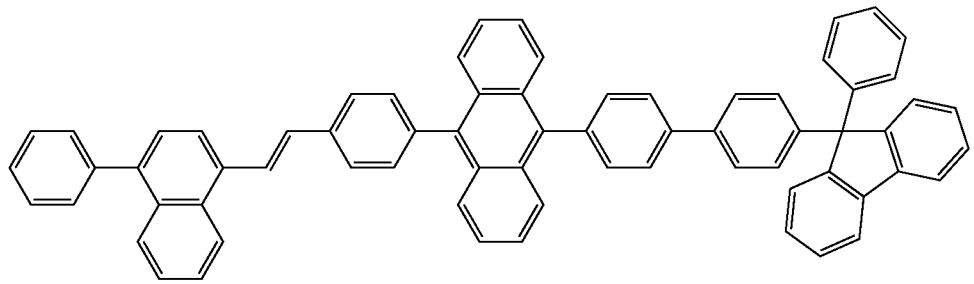
96
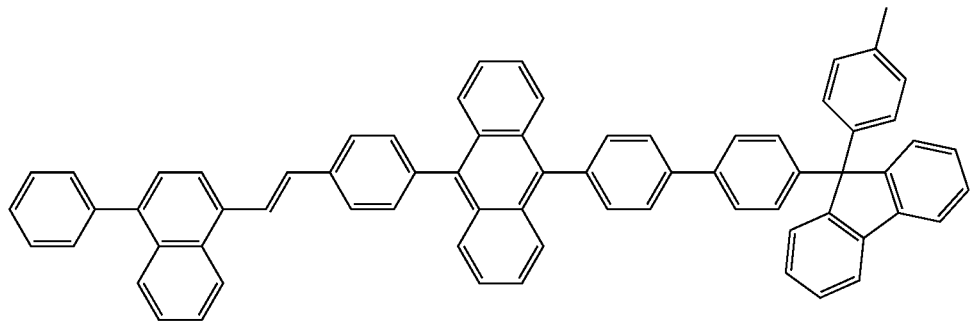

-continued
97
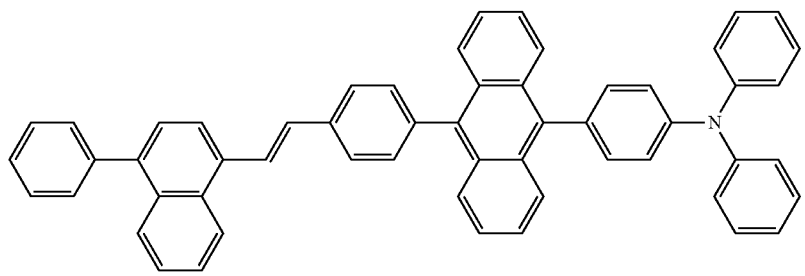
98
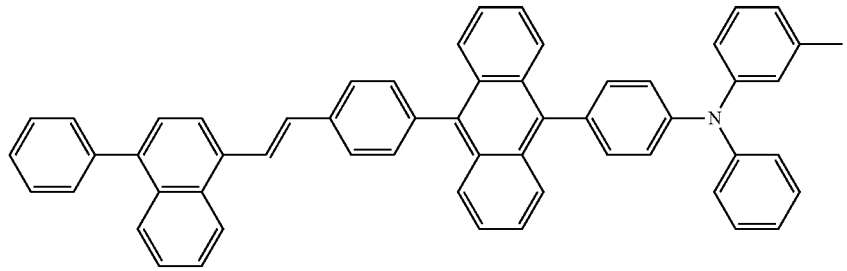
99
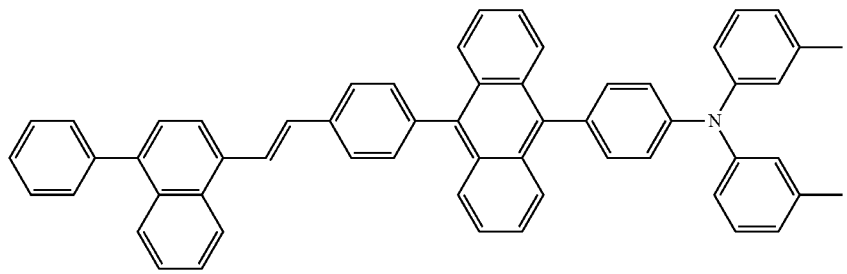
100
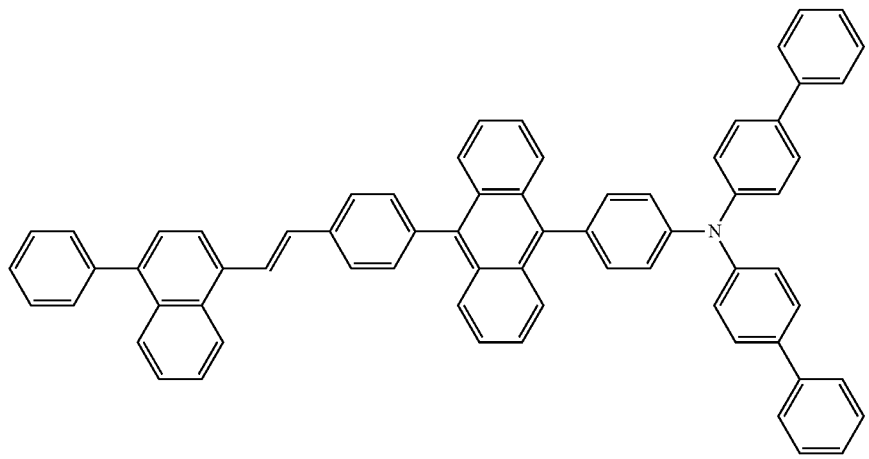
101
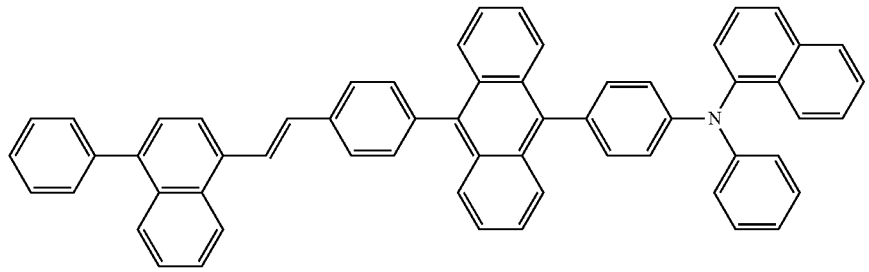

-continued
102
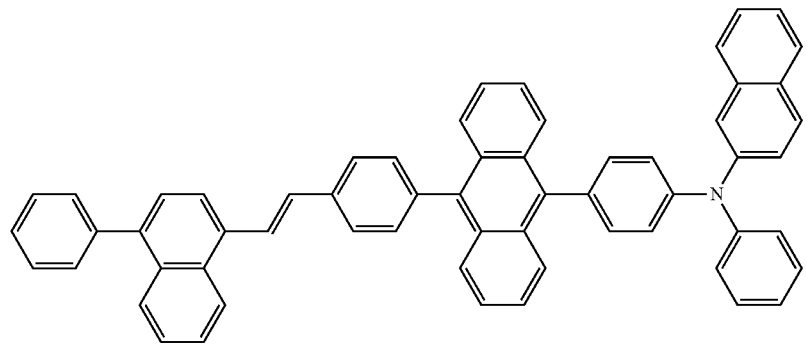
103
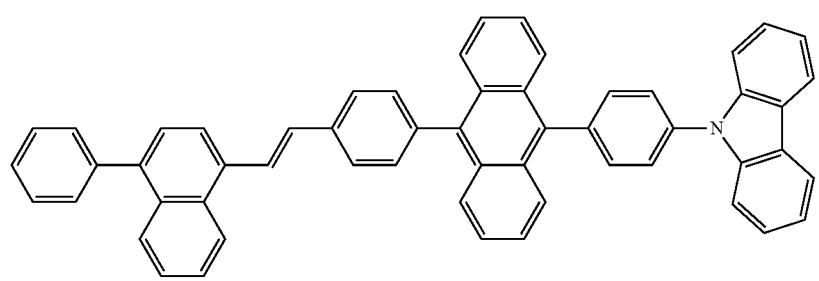
104
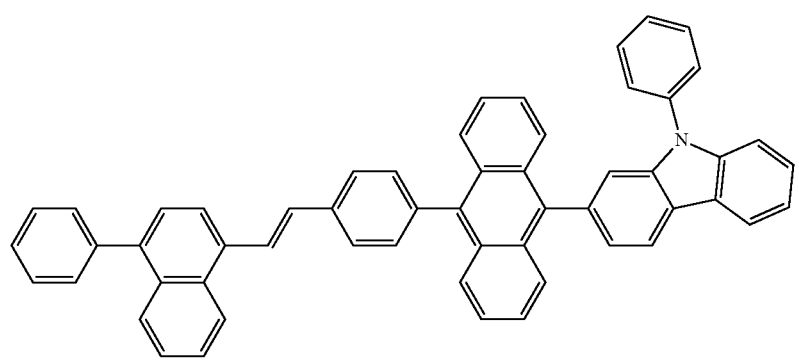
105
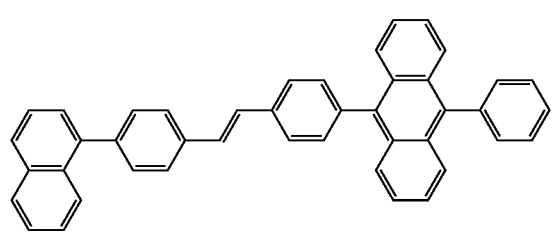
106
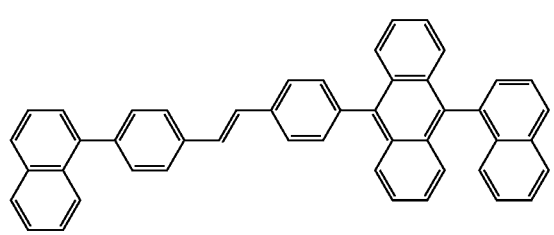
107
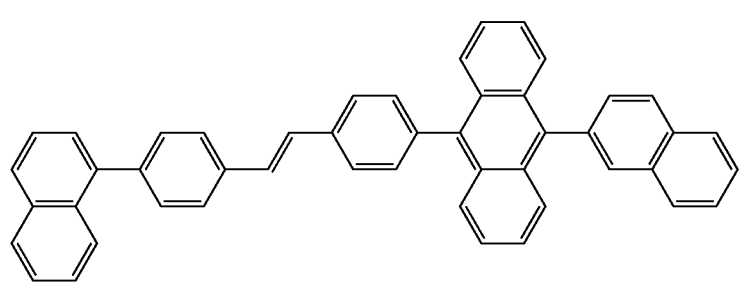

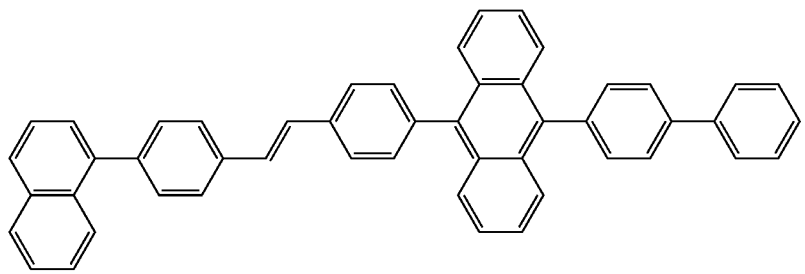 [SMILES: C(=C\c1ccc(-c2c3ccccc3c(-c3ccc(-c4ccccc4)cc3)c3ccccc23)cc1)/c1ccc(-c2cccc3ccccc23)cc1]
108
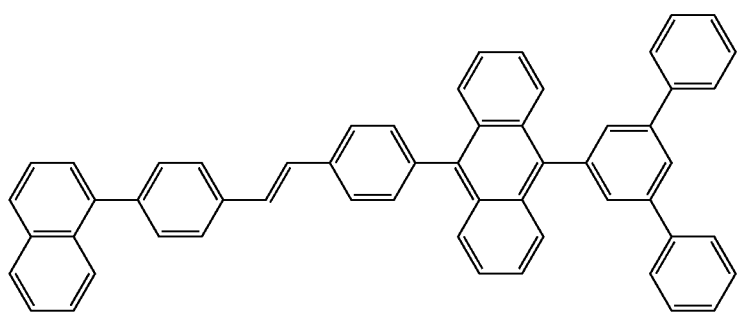
109
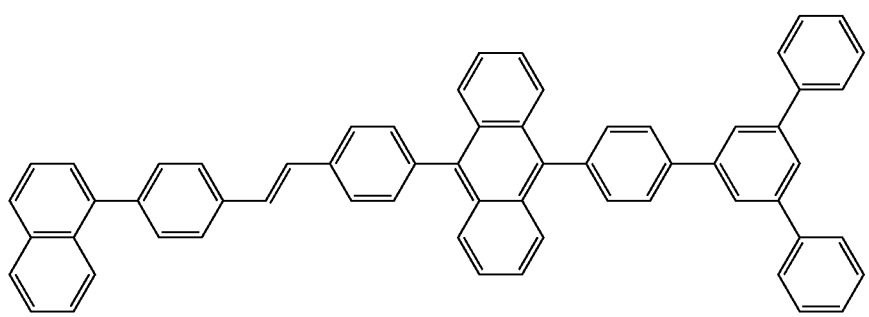
110
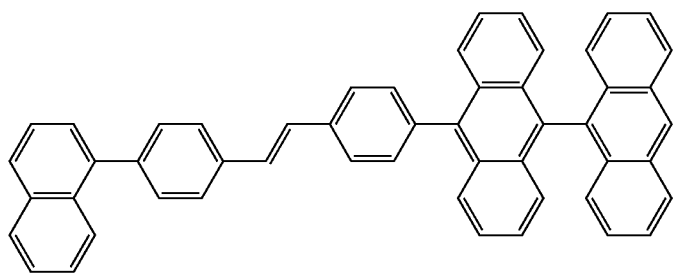
111
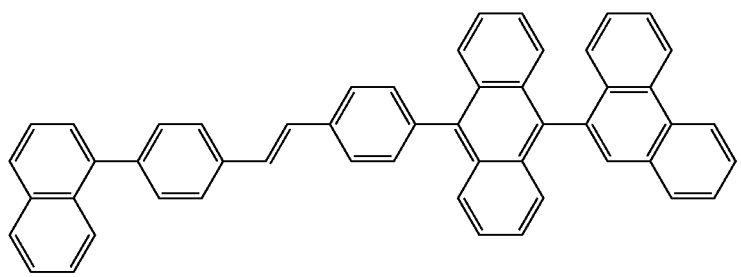
112

-continued
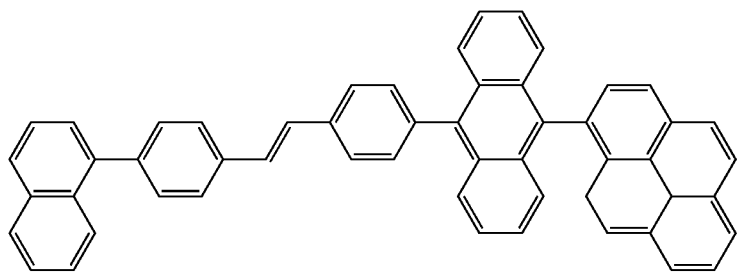
113
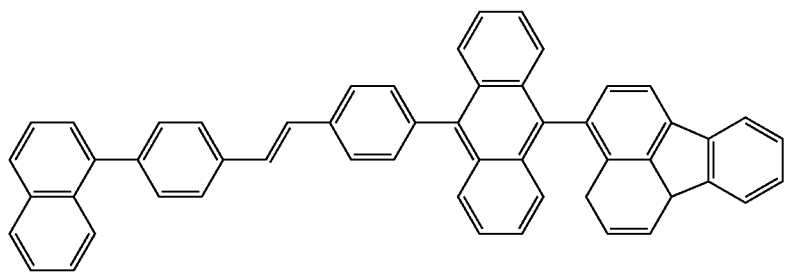
114
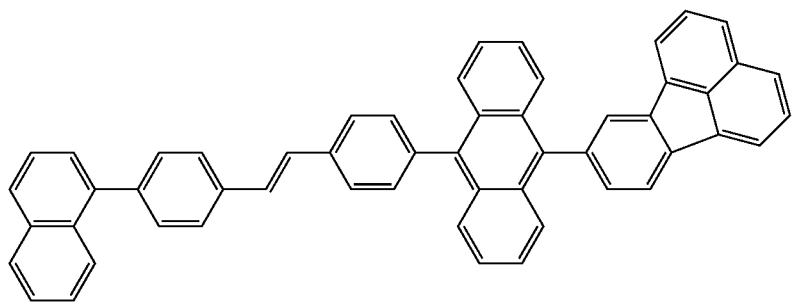
115
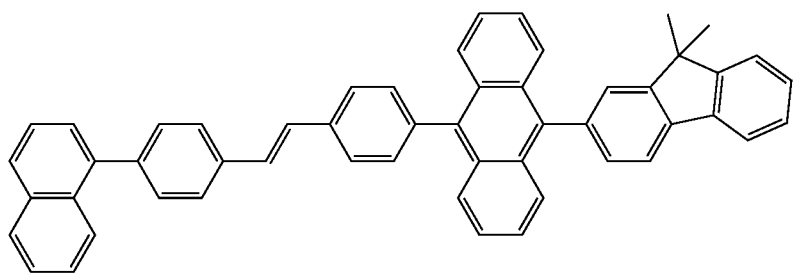
116
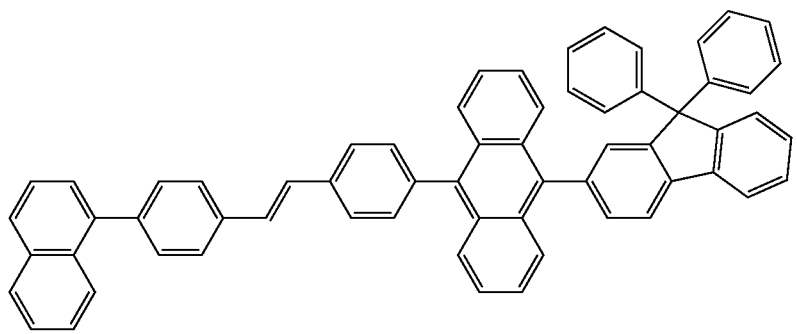
117

-continued
118
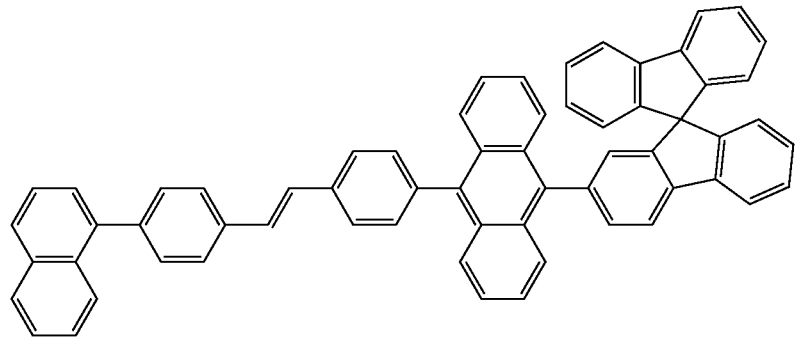
119
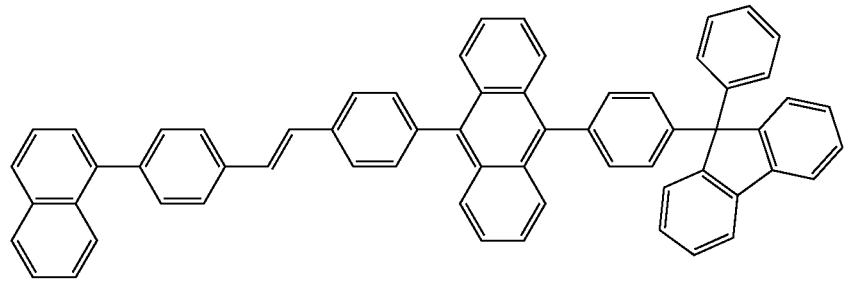
120
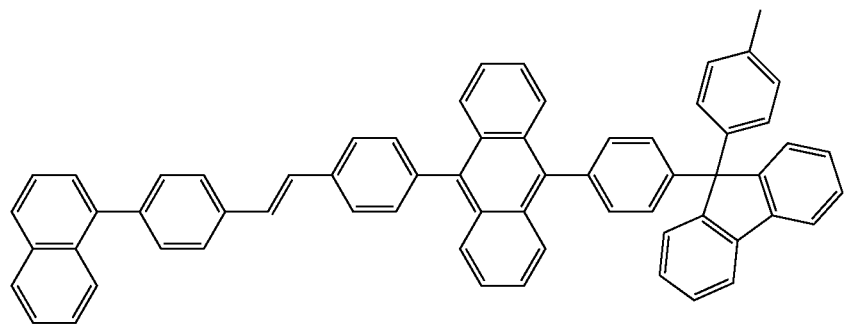
121
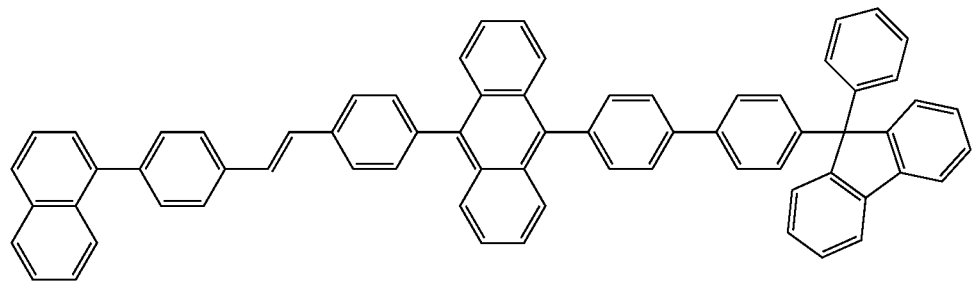
122
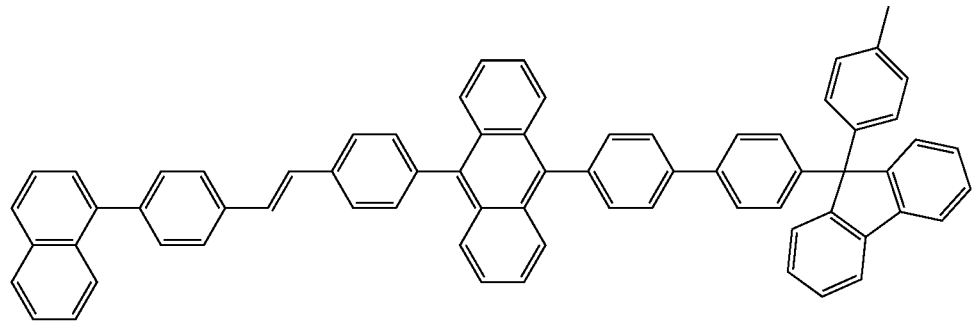

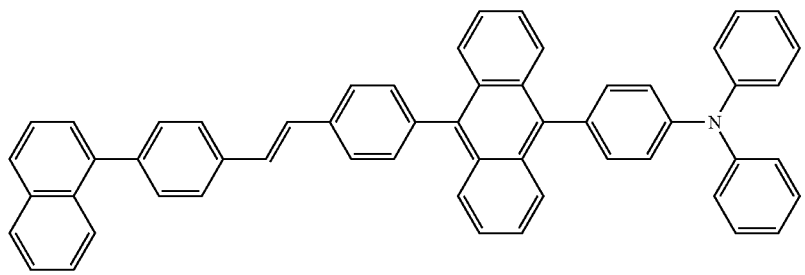
123
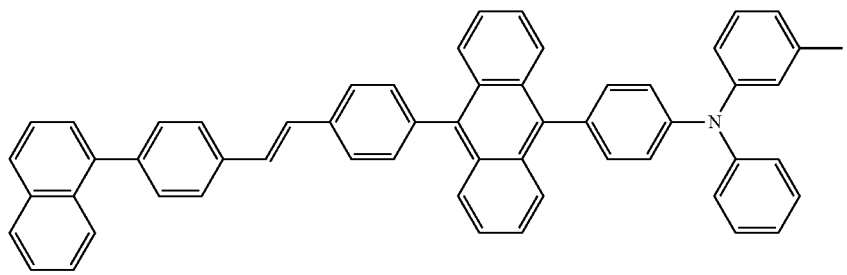
124
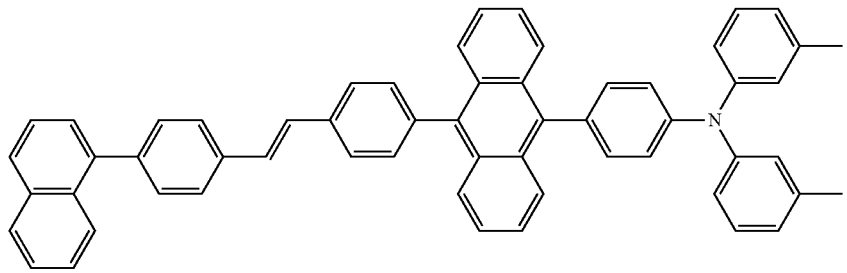
125
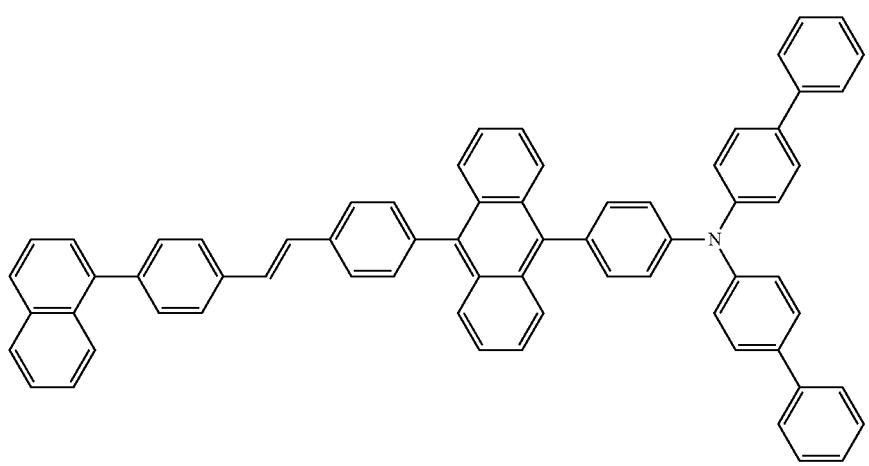
126
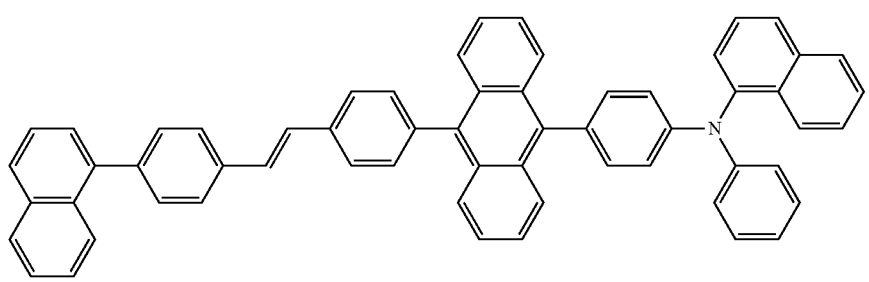
127

-continued
128
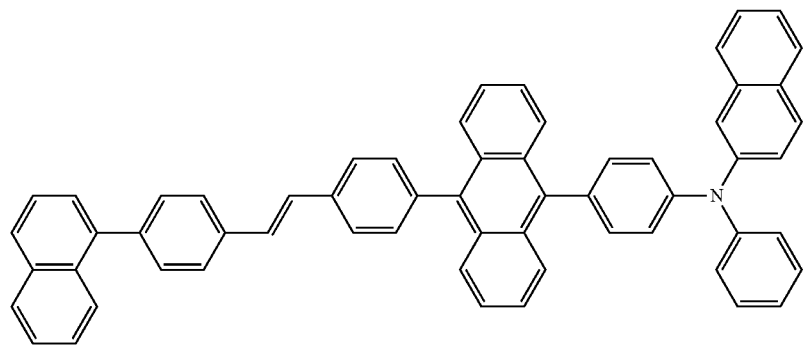
129
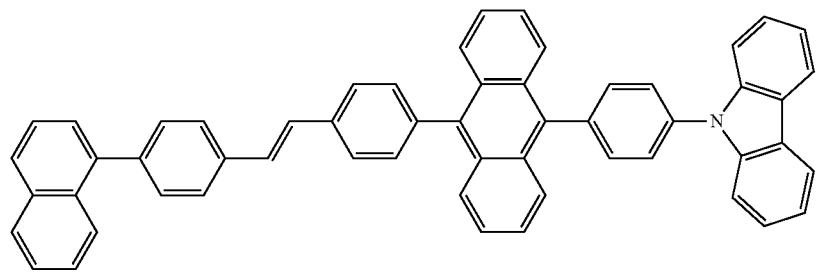
130
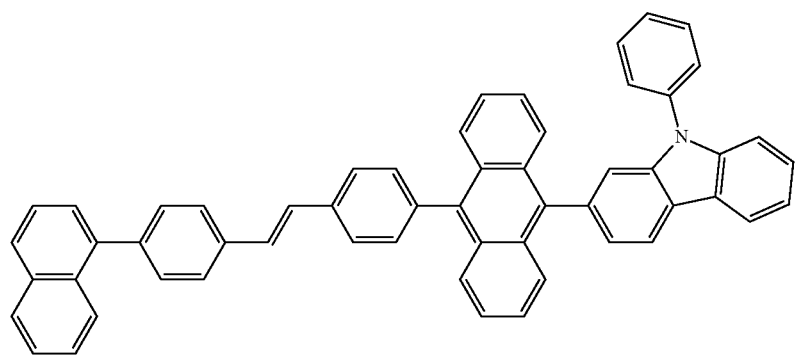
131 132
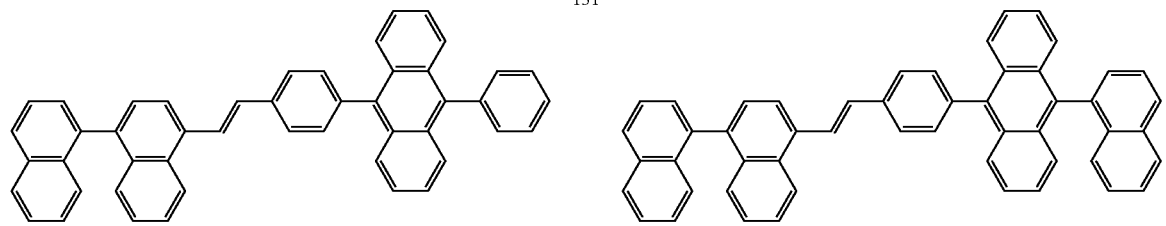
133
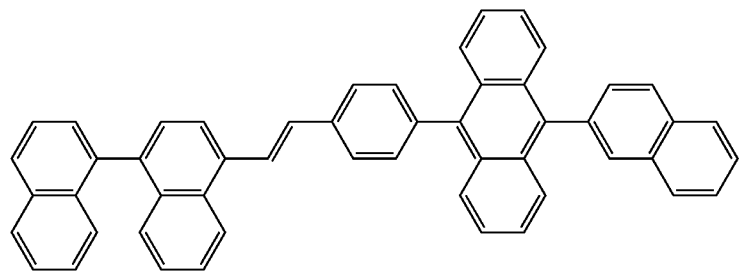

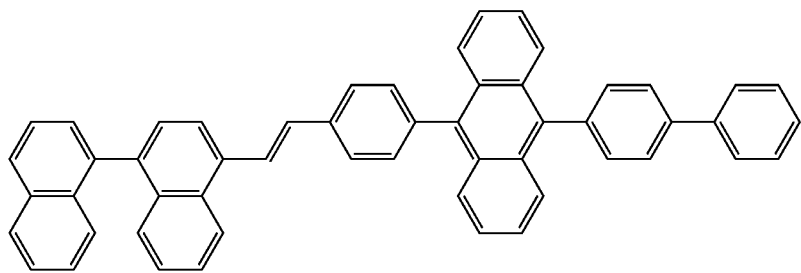
134
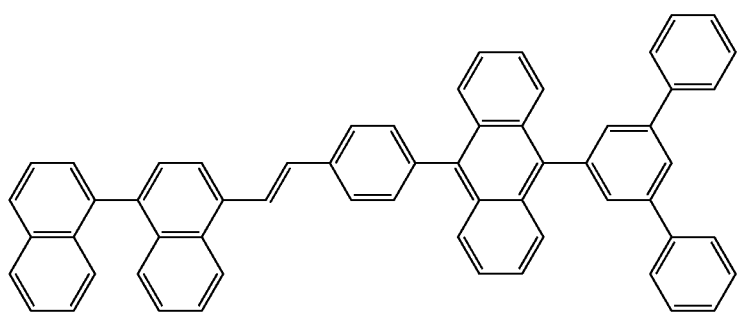
135
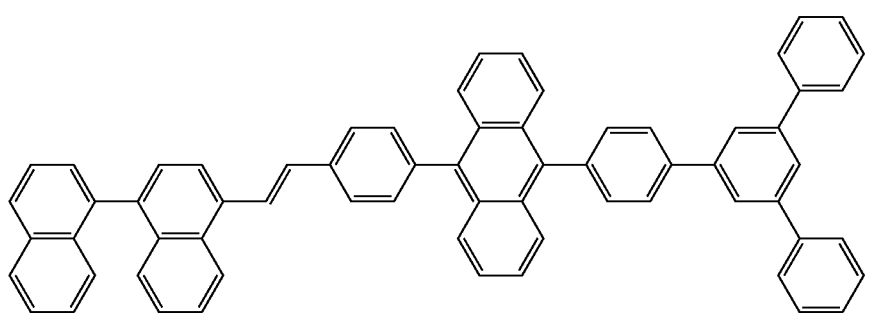
136
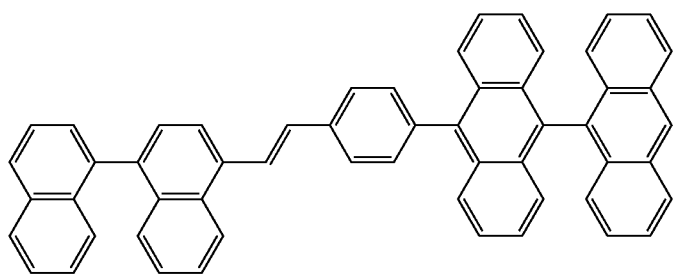 [SMILES: C(=C\c1ccc(-c2c3ccccc3c(-c3c4ccccc4cc4ccccc34)c3ccccc23)c2ccccc12)/c1ccc(-c2cccc3ccccc23)c2ccccc12]
137
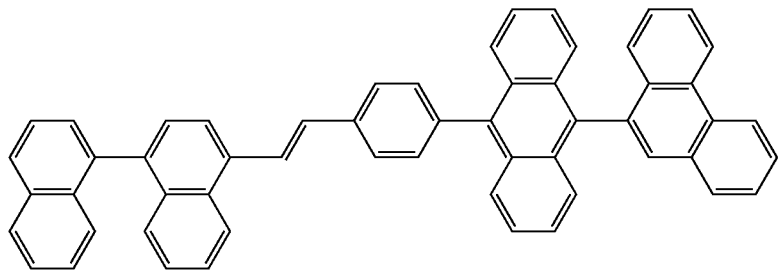
138

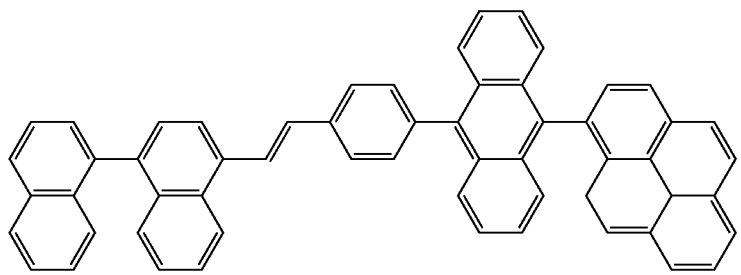
139
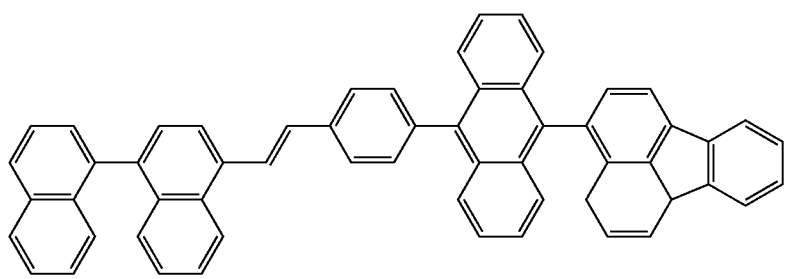
140
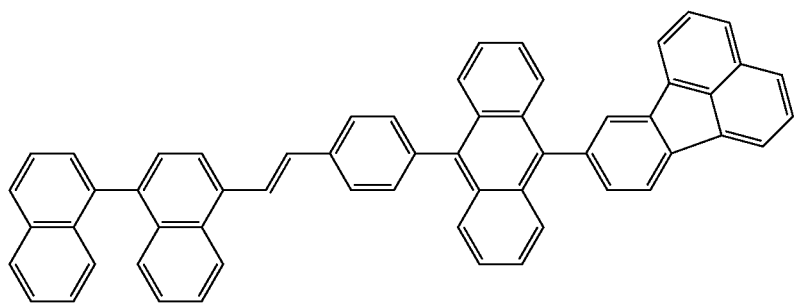
141
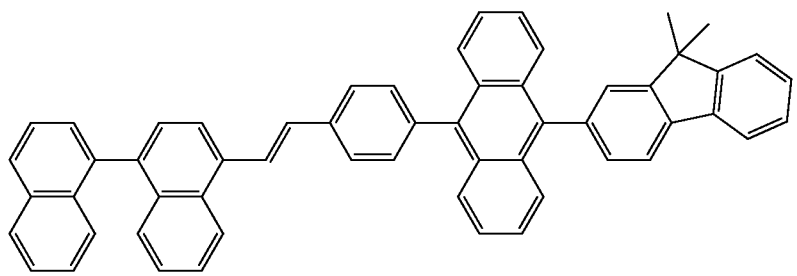
142
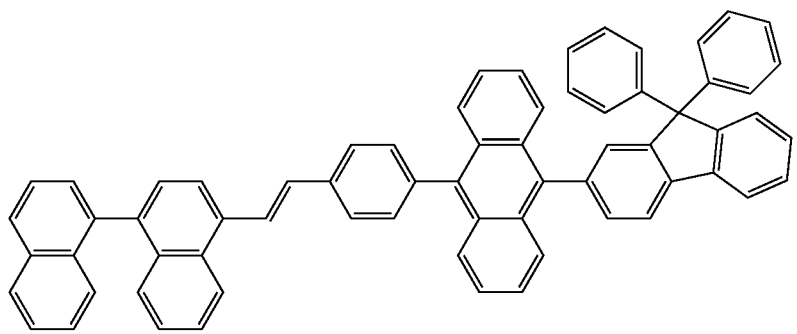
143

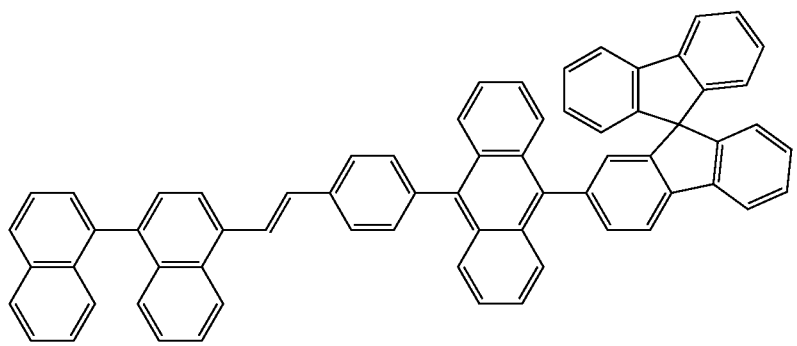
144
145
146
147
148

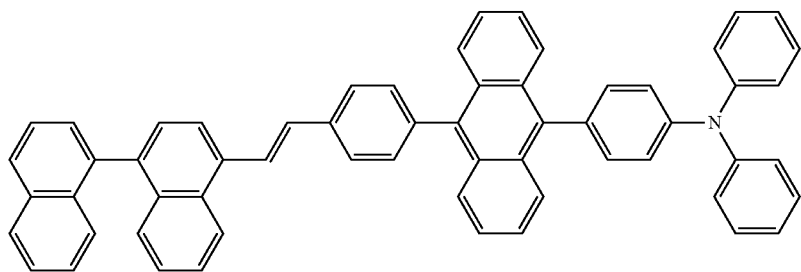
149
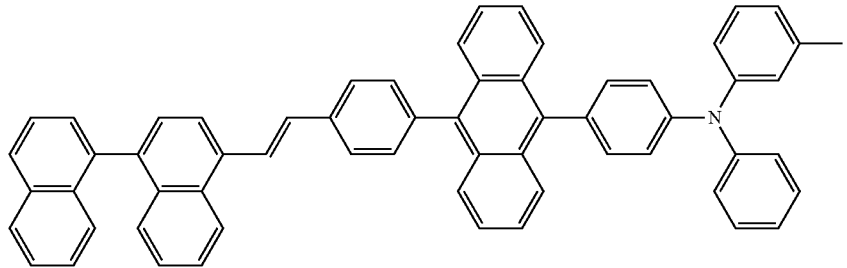
150
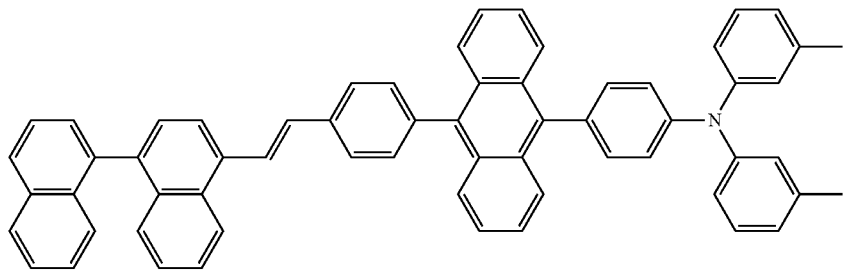
151
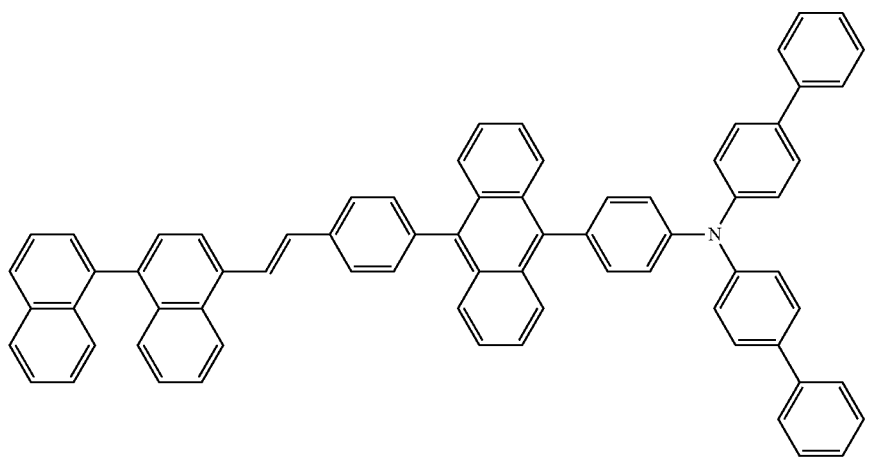
152
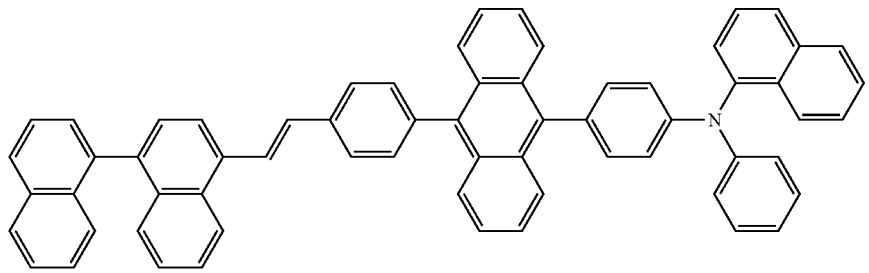
153

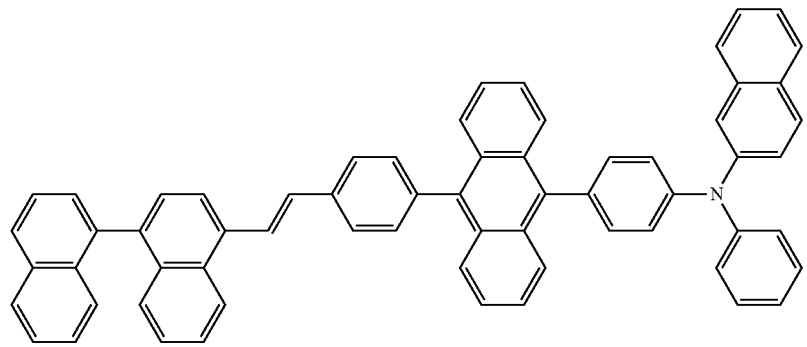
154
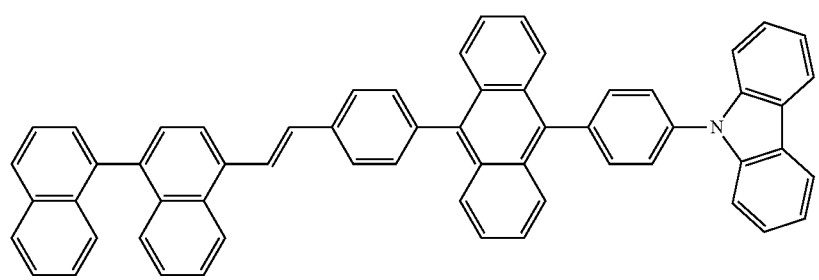
155
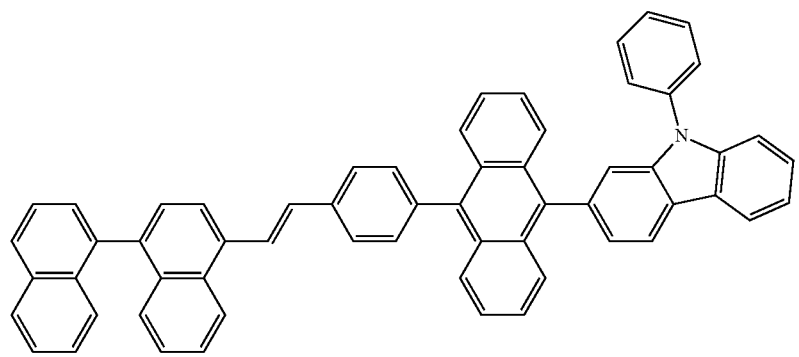
156
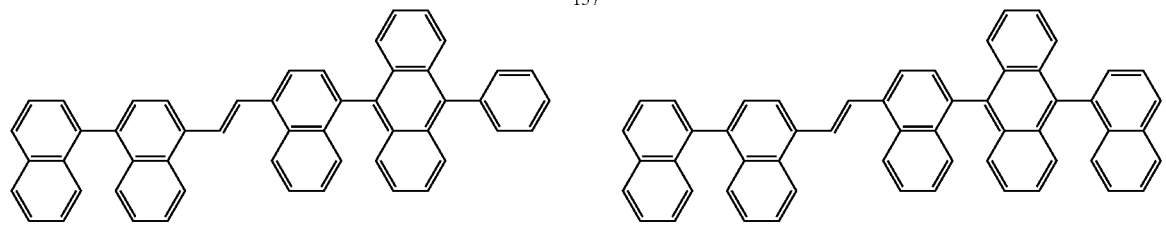
157 158
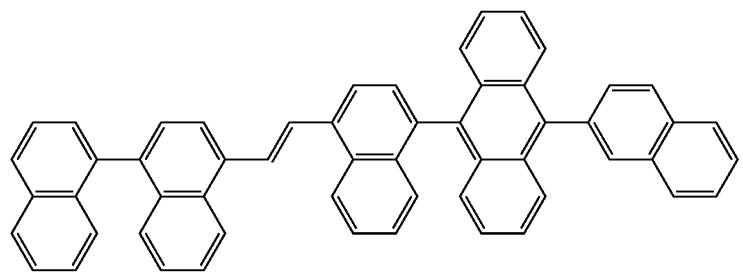
159

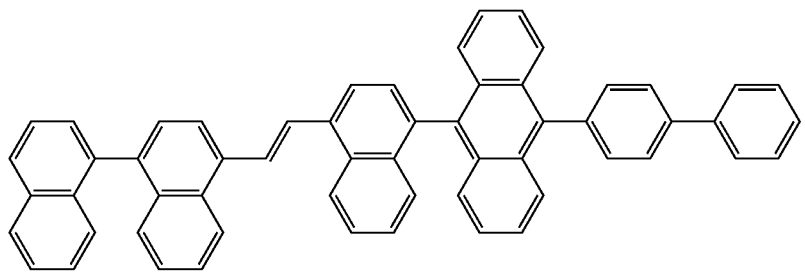

165
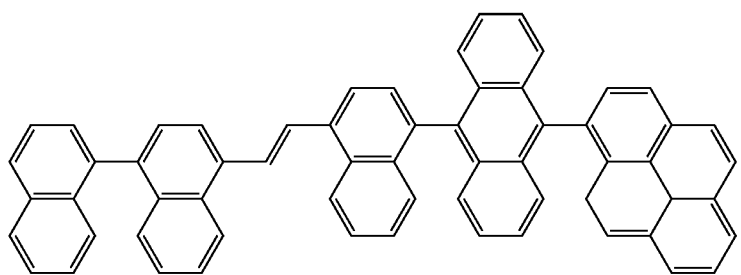
166
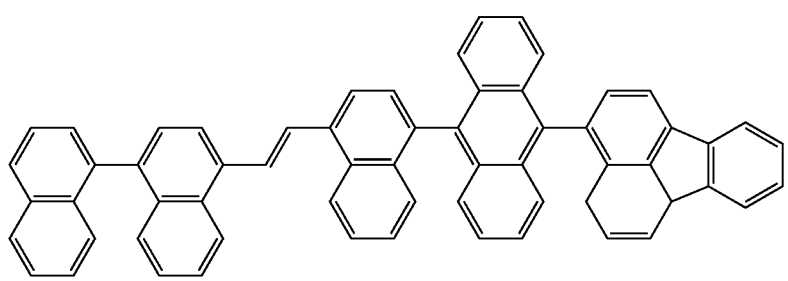
167
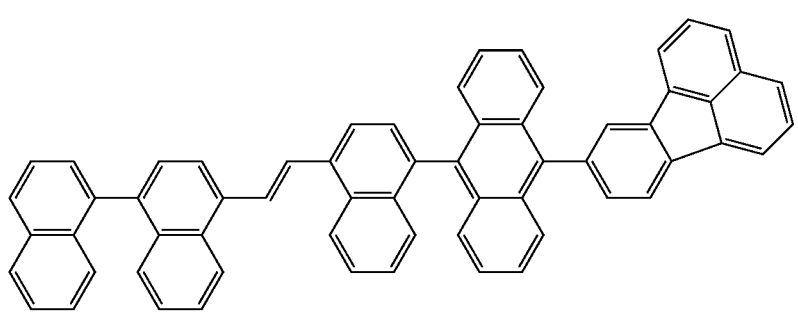
168
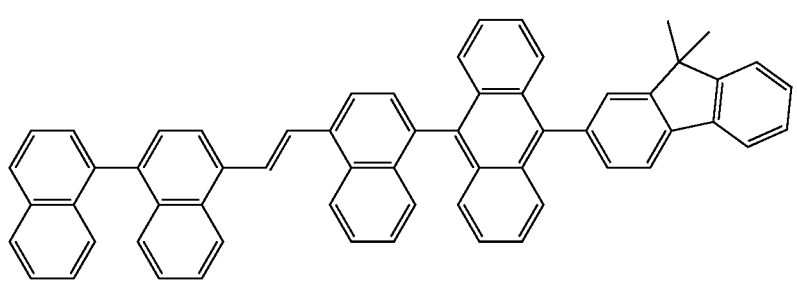
169
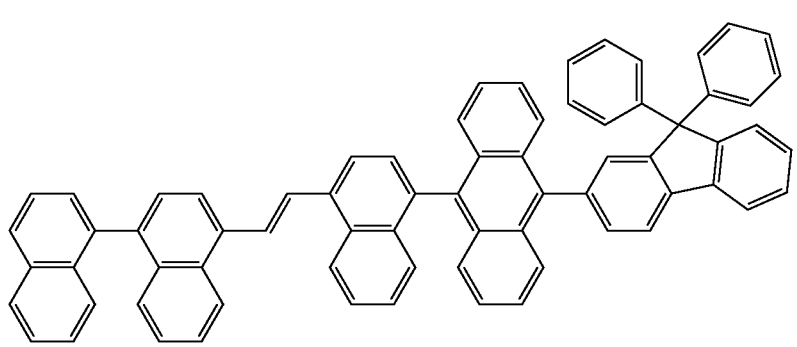

170
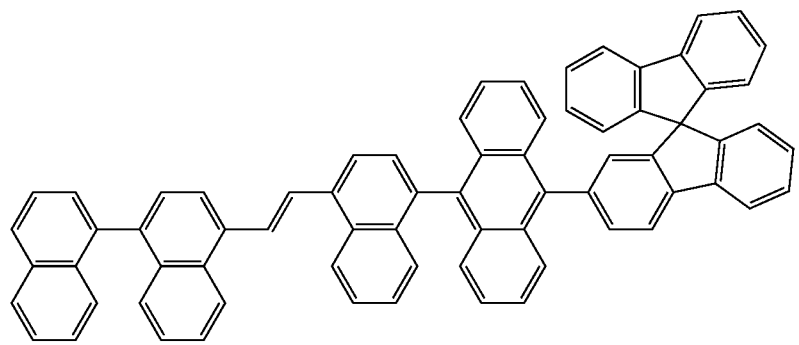
171
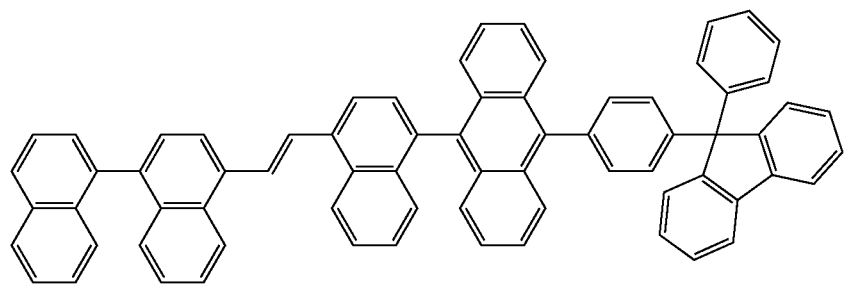
172
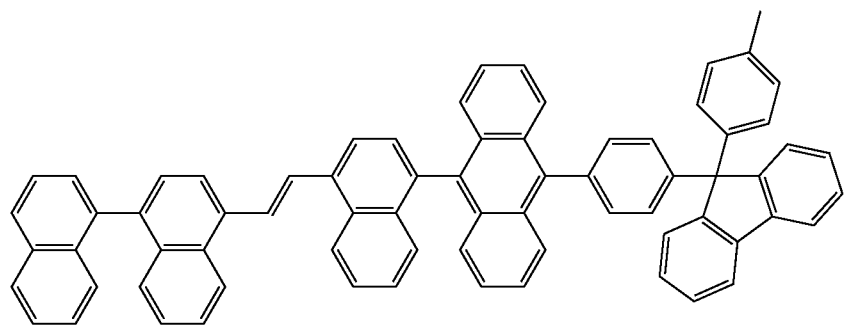
173
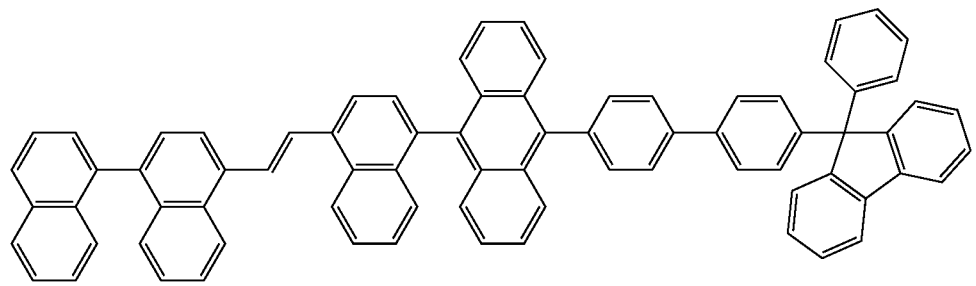
174
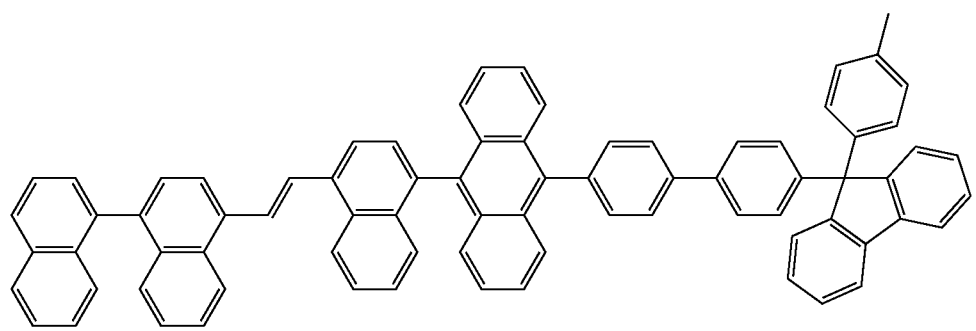

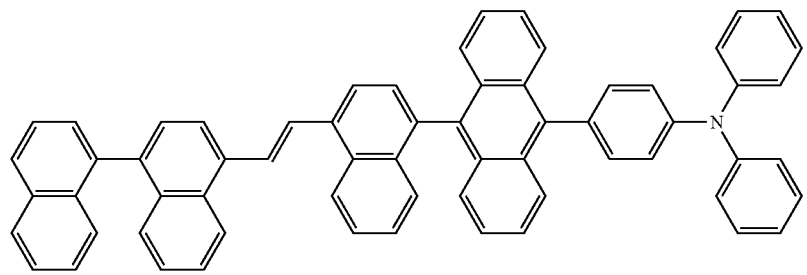

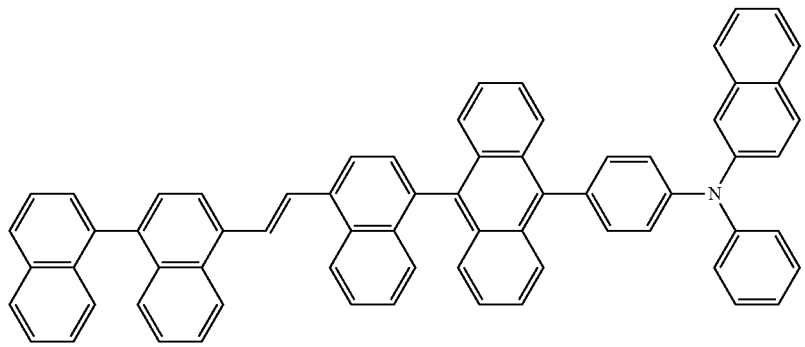

180

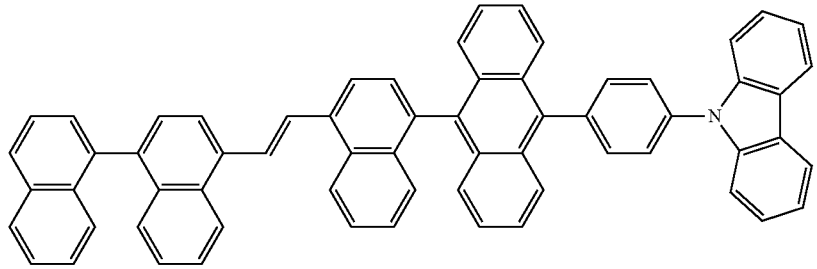

181

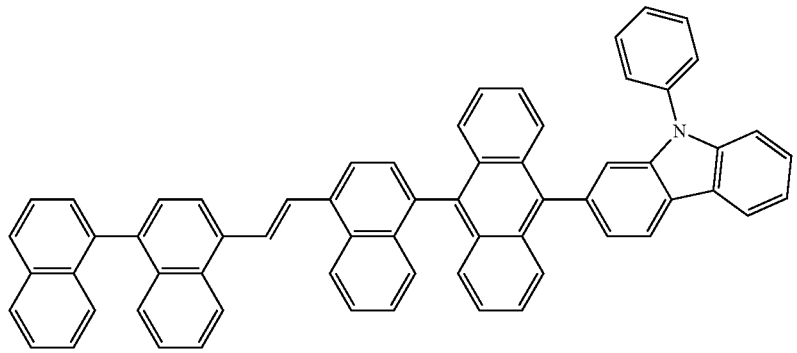

182

The materials of the hole transport layer and hole injection layer in the present invention should have good hole transport performance, which can effectively transport the holes from the anode to the organic light emitting layer. The materials used can include small molecule or polymer organic materials, including but not limited to triaryl amine compounds, benzidine compounds, thiazole compounds, oxazole compounds, imidazole compounds, fluorene compound, phthalocyanine compounds, dipyrazino[2,3-f:2',3'-h]quinoxaline-2,3,6,7,10,11-hexacarbonitrile (HAT-CN), 2,3,5,6-tetrafluoro-7,7,8,8-tetracyano-quinodimethane (F4-TCNQ), polyvinyl carbazole, polythiophene, polyethylene, polystyrene sulfonic acid.

The organic light emitting layer in the present invention can contain, in addition to the invented anthracene vinyl compounds, the following but not limited to the following compounds: naphthalene compounds, pyrene compounds, fluorene compounds, phenanthrene compounds, chrysene compounds, fluoranthene compounds, anthracene compounds, pentacene compounds, perylene compound, bi-aryl vinyl compounds, triphenylamine vinyl compounds, amine compounds, benzimidazole compounds, furan compounds and organic metal chelate compounds.

The organic electron transport material of the organic electronic devices in the present invention should have good electron-transport performance, which can efficiently transport electrons from the cathode to the light emitting layer. These materials can be selected from the following compounds, but not limited to oxazole, thiazoles compounds, triazole compounds, triazine compounds, tri-aza benzene compounds, quinoxaline compounds, di-aza anthracene compounds, silicon-containing heterocyclic compounds, quinoline compounds, phenanthroline compounds, metal chelates, fluoro-substituted benzene compounds.

One electron injection layer can be added to the organic electronic device of the present invention as required. The electron injection layer can effectively inject electrons from the cathode into the organic layer, and could be mainly selected from alkali metals or alkali metal compounds, or selected from alkaline earth metals or alkaline earth metal compounds, including but not limited to the following: lithium, lithium fluoride, lithium oxide, lithium nitride, 8-hydroxyquinolato lithium, cesium, cesium carbonate, 8-hydroxyquinolato cesium, calcium, calcium fluoride, calcium oxide, magnesium, magnesium fluoride, magnesium carbonate, magnesium oxide.

Experimental results show that, the OLEDs in the present invention have advantages of good light-emitting efficiency, excellent color purity and long lifetime.

DETAILED DESCRIPTIONS OF THE PREFERRED EMBODIMENTS

Figure 1:
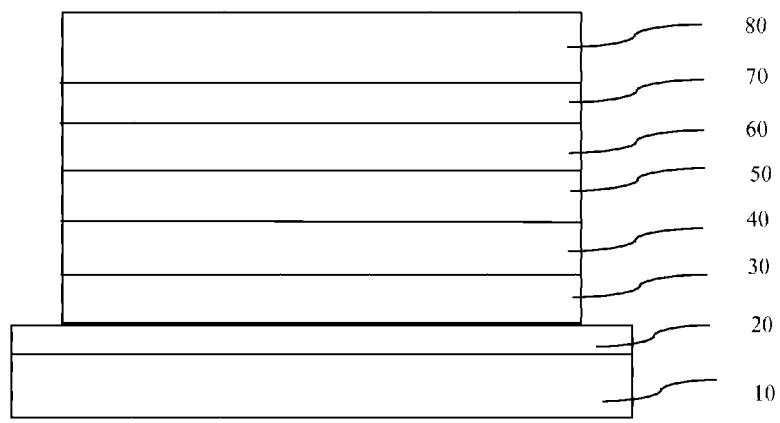
FIG. 1 is a structural drawing of the device, of which, 10 denotes a glass substrate, 20 denotes an anode, 30 denotes a hole injection layer, 40 denotes a hole transport layer, 50 denotes a light emitting layer, 60 denotes an electron transport layer, 70 denotes an electron injection layer, 80 denotes a cathode.

In the following, the present invention is described in details by giving the following examples.

Embodiment 1

Synthesis of Compound 110

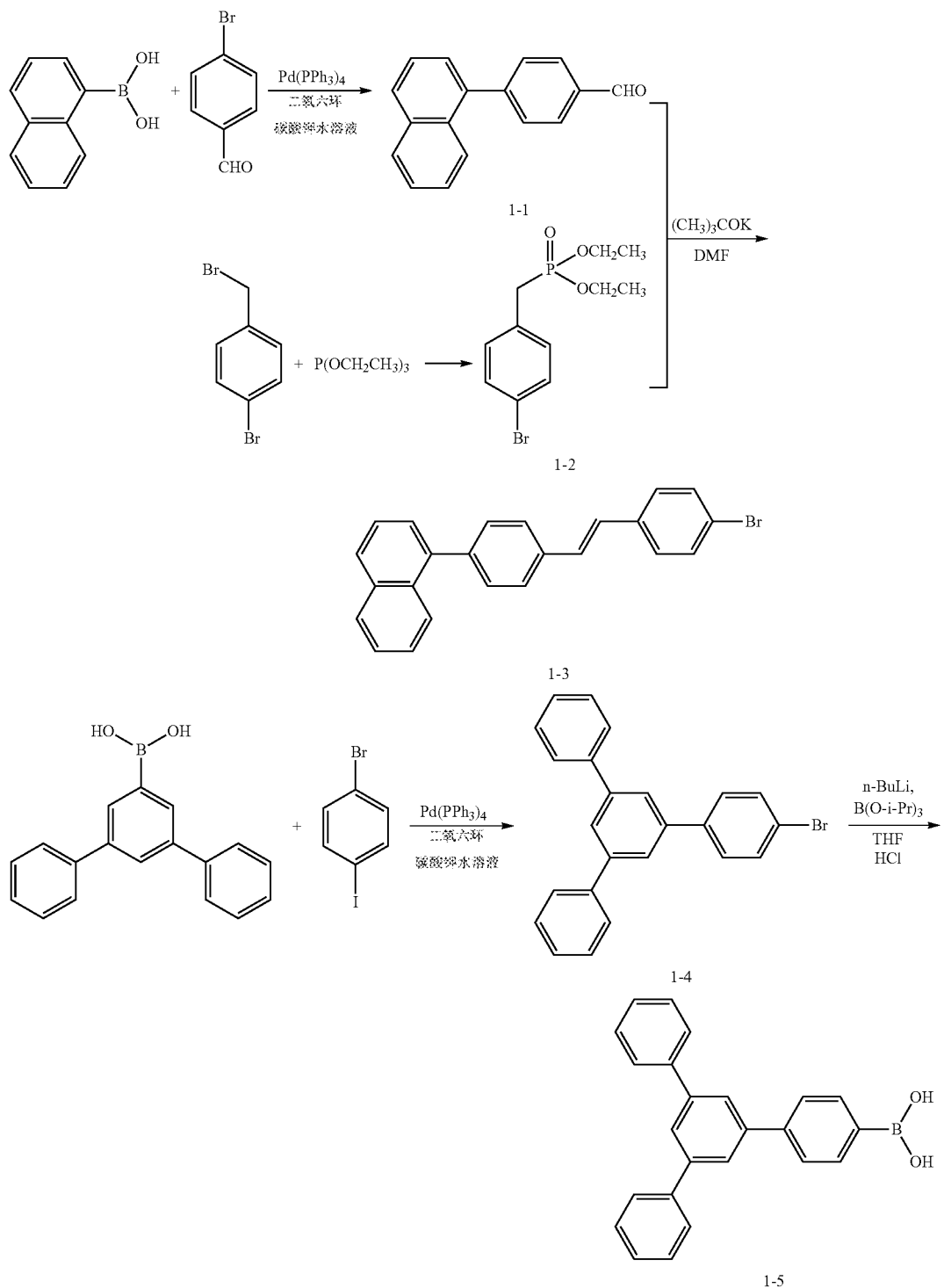

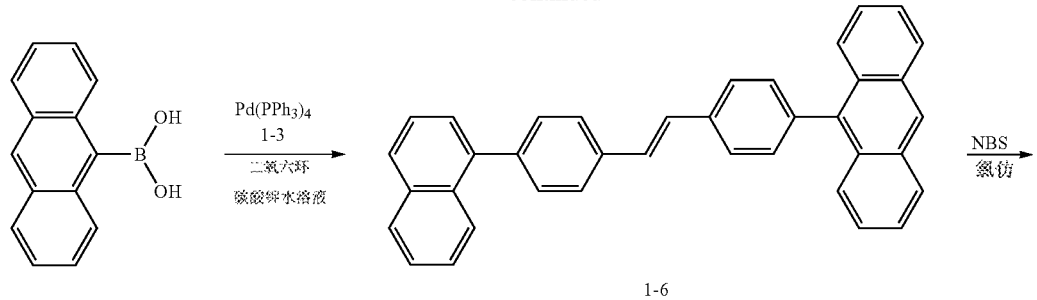

1-6

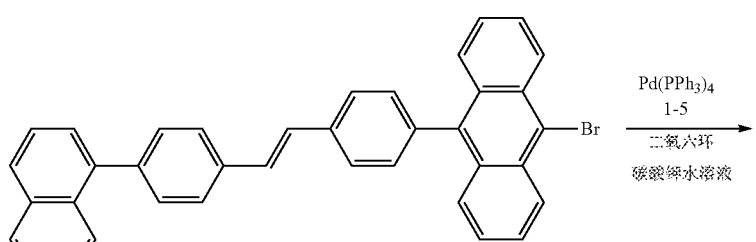

1-7

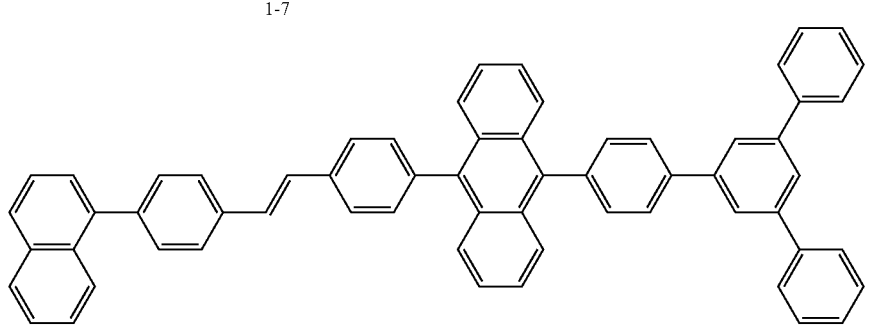

化合物 110

Synthesis of Intermediate 1-1

To a 1 L single-necked flask, was added 25.5 g 1-naphthaleneboronic acid and 25 g bromobenzaldehyde, 400 ml dioxane, 80 ml 2 M potassium carbonate solution, 1.0 g tetrakis(triphenylphosphine)palladium under the protection of nitrogen. The mixture was refluxed for 12 hours, cooled down, and extracted three times with ethyl acetate. The organic phase was dried over anhydrous sodium sulfate, concentrated, and recrystallized from ethanol to yield 29 g solid (92%).

Synthesis of Intermediate 1-3

To a 500 ml single-neck flask, was added 25 g p-bromobenzyl bromide and 49.8 ml triethyl phosphite (1-2). The mixture was refluxed for 2 hours, then the excess triethyl phosphate was removed. 23.4 g intermediate 1-1, 250 ml DMF, and 16.8 g potassium tert-butoxide were added into the flask in an ice bath. The resulting mixture was allowed to warm to the room temperature, and stirred overnight. The reaction mixture was poured into distilled water, filtered, and the precipitate was recrystallized from ethanol to yield 31.8 g product (83%).

Synthesis of Intermediate 1-4

To a 1 L one-neck flask, was added 45 g 3,5-diphenylphenyl boronic acid and 42.5 g 1-bromo-4-iodobenzene, 450 ml dioxane, 150 ml 2M potassium carbonate aqueous solution, and 1.7 g tetrakis(triphenylphosphine)palladium under nitrogen. The mixture was refluxed for 12 hours, cooled down, and extracted three times with ethyl acetate. The organic phase was dried over anhydrous sodium sulfate, concentrated, and the crude product was recrystallized from ethanol to yield 54.6 g product (95%).

Synthesis of Intermediate 1-5

With the protection of nitrogen, 20 g intermediate 1-4 and 300 ml THF were added into a 1 L three-necked flask. To the above solution was added dropwise 21 ml 2.5M n-butyl lithium under −78° C. and kept for 2 hours. Then 16.6 g triisopropyl borate was added and kept for another hour. The mixture was allowed to warm to room temperature and reacted for another 12 hours. The reaction mixture was neutralized with 2N dilute hydrochloric acid, and extracted three times with ethyl acetate. The resulting organic phase was dried over anhydrous sodium sulfate, concentrated, and the crude product was recrystallized from ethyl acetate and n-hexane to yield 14 g product (78%).

Synthesis of Intermediate 1-6

To a 500 ml single-neck flask, was added 20 g intermediate 1-3, 14 g 9-anthraceneboronic acid, 350 ml dioxane, 70 ml potassium carbonate solution, and 0.6 g tetrakis(triphenylphosphine)palladium under nitrogen. The mixture was refluxed for 12 hours, cooled down, and extracted three times with ethyl acetate. The organic phase was dried over anhydrous sodium sulfate, and concentrated. The crude product was stirred in boiling THF, cooled down, filtered, and dried to yield 20 g product (80%).

Synthesis of Intermediate 1-7

To a 500 ml single-neck flask, was added 20 g intermediate 1-6, 10.4 g NBS and 400 ml chloroform. The mixture was stirred at 25° for 12 hours, then concentrated, and recrystallized from THF and ethanol to give 17 g product (73.3%).

Synthesis of Compound 110

Figure 2:
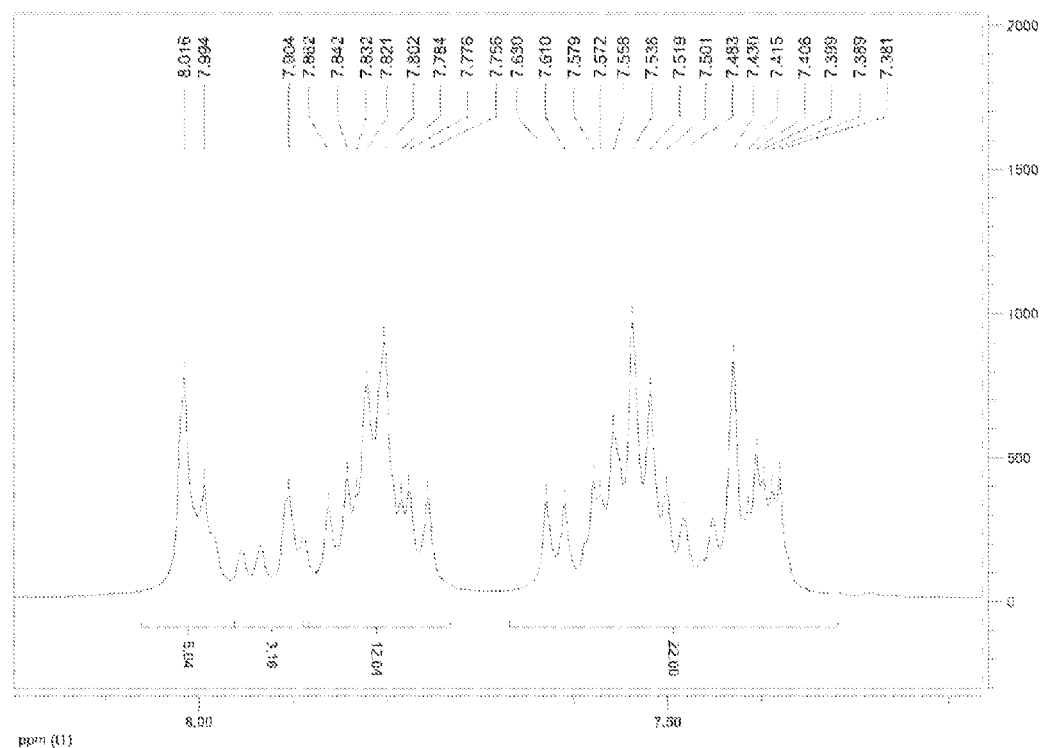
FIG. 2 is the $^1$H NMR spectrum of compound 110.

To a 250 ml single-neck flask, was added 5.5 g intermediate 1-5, 7.3 g intermediate 1-7, 75 ml dioxane, 20 ml 2M potassium carbonate aqueous solution, 0.15 g tetrakis(triphenylphosphine)palladium under nitrogen. The mixture was refluxed for 12 hours, cooled down, and extracted three times with ethyl acetate. The organic phase was dried over anhydrous sodium sulfate, and concentrated. The crude product was stirred in boiling THF, cooled down, filtered, and dried to give 7.7 g product (75.5%). $^1$H NMR (400 MHz, CD$_2$Cl$_2$), δ: 7.99-8.02 (m, 5H), 7.88-7.95 (m, 3H), 7.76-7.86 (m, 12H), 7.38-7.63 (m, 22H); MALDI-TOF-MS m/z found 786.5, C$_{62}$H$_{42}$ [M$^+$] requires 786.3. The $^1$H NMR of compound 110 is shown in FIG. 2.

Embodiment 2

Synthesis of Compound 122

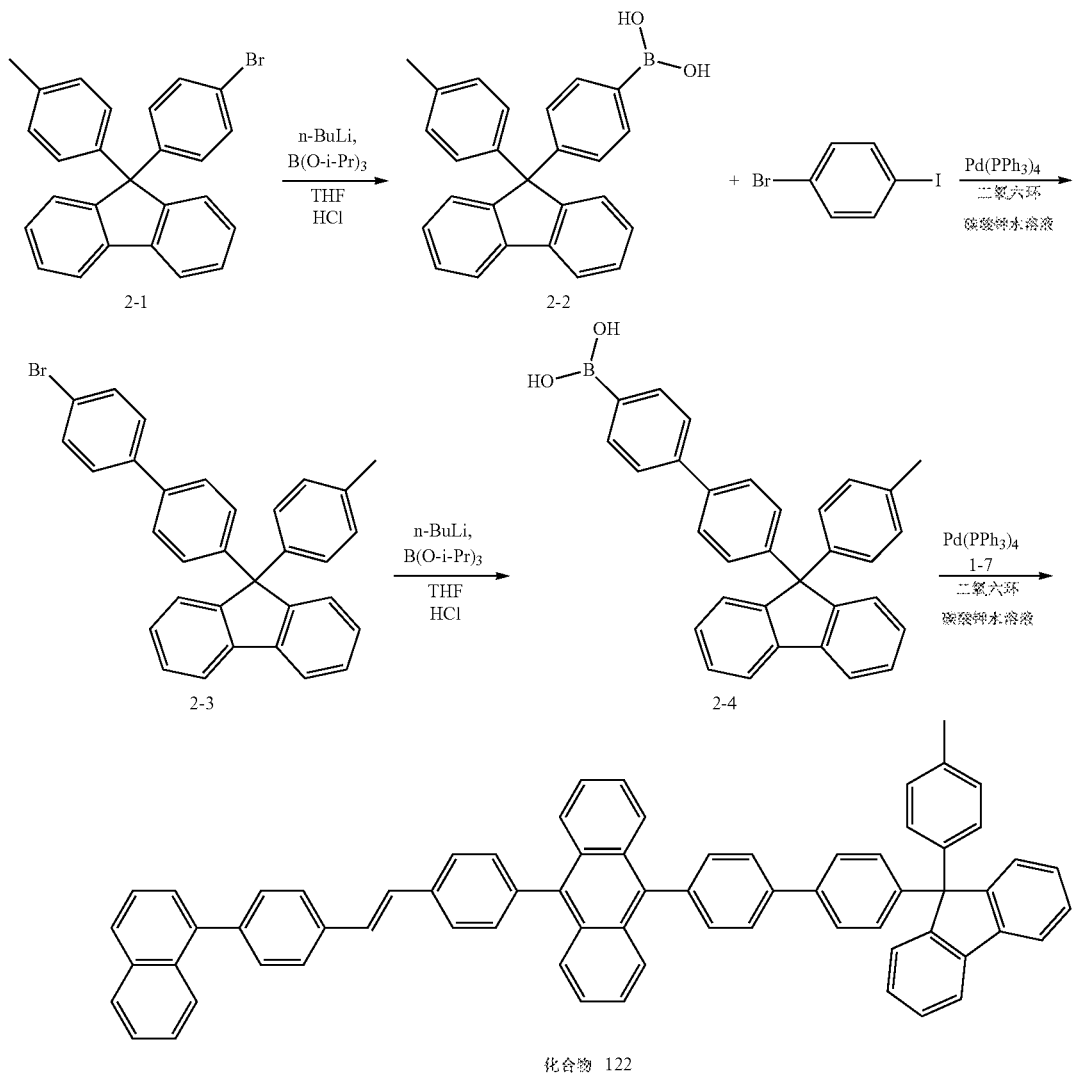

化合物 122

Synthesis of Intermediate 2-2

With the protection of nitrogen, 36.3 g intermediate (2-1) and 400 ml THF were added into a 1 L three-necked flask, which was cooled down to −78° C. followed by adding dropwise 50 ml 2.5M n-butyl lithium and kept stirring for 2 hours. Then 30 g triisopropyl borate was added and the mixture was kept stirring at low temperature for another 1 hour before allowed to warm to room temperature and stirred for another 12 hours. 2N dilute hydrochloric acid was added to neutralize the reaction mixture, which was then extracted three times with ethyl acetate. The organic phase was dried over anhydrous sodium sulfate, concentrated, and recrystallized from ethyl acetate and n-hexane to yield 27 g product (90%).

Synthesis of Intermediate 2-3

To a 500 ml one-neck flask, was added 25 g intermediate 2-2, 14.5 g 1-bromo-4-iodobenzene, 300 ml dioxane, 60 ml 2M potassium carbonate aqueous solution, 0.6 g tetrakis(triphenylphosphine)palladium under nitrogen. The mixture was refluxed for 12 hours, cooled down, and extracted three times with ethyl acetate. The organic phase was dried over anhydrous sodium sulfate, and concentrated. The crude product was washed in refluxing THF, cooled down, filtered, and dried to yield 22 g product (70%).

Synthesis of Intermediate 2-4

With the protection of nitrogen gas, 15.5 g intermediate 2-3 and 300 ml THF was added into a 250 ml three-necked flask, which was cooled down to −78° C. followed by adding dropwise 17 ml 2.5M n-butyl lithium and kept stirring for 2 hours. Then 10.2 g triisopropyl borate was added and the mixture was kept stirring at low temperature for another 1 hour before allowed to warm to room temperature and stirred for another 12 hours. 2N dilute hydrochloric acid was added to neutralize the reaction mixture, which was then extracted three times with ethyl acetate. The organic phase was dried over anhydrous sodium sulfate, concentrated, and the crude product recrystallized from ethyl acetate and n-hexane to yield 14 g product (90%).

Synthesis of Compound 122

To a 250 ml single-neck flask was added 7 g intermediate 2-5, 8 g intermediate 1-7, 120 ml dioxane, 24 ml 2M potassium carbonate aqueous solution, 0.16 g tetrakis(triphenylphosphine)palladium under nitrogen. The mixture was refluxed for 12 hours, cooled down, and extracted three times with ethyl acetate. The organic phase was dried over anhydrous sodium sulfate and concentrated. The crude product was washed in refluxing THF, cooled down, filtered and dried to yield 10 g product (79%). $^1$H NMR (400 MHz, CD$_2$Cl$_2$,) δ: 7.98-8.00 (d, J=8.4 Hz, 2H), 7.94-7.96 (d, J=7.6 Hz, 2H), 7.89-7.91 (d, J=8.0 Hz, 2H), 7.76-7.86 (m, 12H), 7.65-7.67 (d, J=8.4 Hz, 2H), 7.48-7.58 (m, 11H), 7.32-7.43 (m, 11H), 7.09-7.17 (m, 6H) 2.32 (s, 3H). The calculated value of MALDI-TOF-MS m/s C$_{70}$H$_{48}$:888.4; measured value [M$^+$]: 888.7.

Embodiment 3

An illustrative preparation process of blue OLED adopting the organic electronic material in the present invention is given as below.

Firstly, the transparent glass substrate 10 (with conductive ITO as anode 20 above) was washed with detergent solution, deionized water, ethanol, acetone, deionized water in sequence, then treated with oxygen plasma for 30 seconds, and then treated with CF$_x$ plasma.

A 5 nm-thick film of MoO$_3$ was evaporated on top of ITO, which is used as the hole injection layer 30.

A 50 nm-thick film of P1 was evaporated as the hole transport layer 40.

A 20 nm-thick film of compound 110 was evaporated above the hole transport layer as the light emitting layer 50.

A 40 nm-thick film of P2 was evaporated above the light emitting layer as the electron transport layer 60.

Finally, a 1.2 nm-thick LiF film was evaporated as the electron injection layer 70, and a 150 nm-thick Al film was evaporated as the device cathode 80.

The device could achieve blue emission with luminance of 980 cd/m$^2$, current efficiency of 4.3 cd/A, power efficiency of 2.1 lm/W at a driving voltage of 7 V.

The said structural formula of the chemicals used in the device

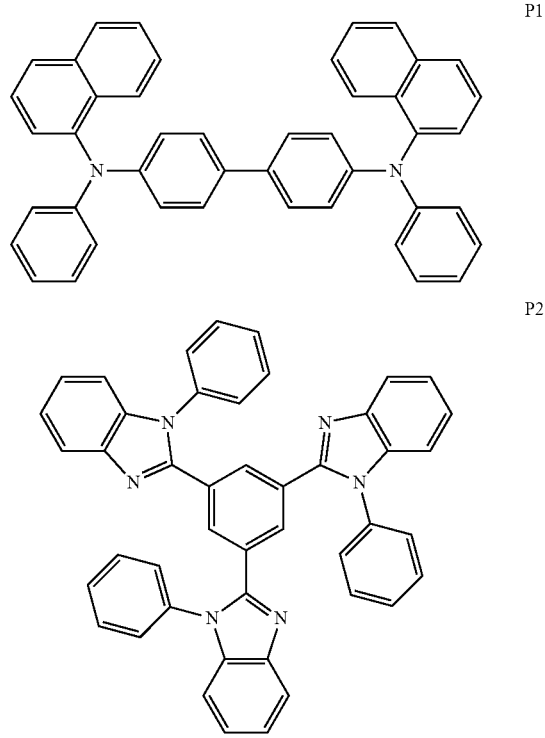

Embodiment 4 (the Device Fabrication Procedures were the Same as that in Embodiment 3)

OLED was made using compound 122 instead of compound 110.

The device could achieve blue emission with luminance of 470 cd/m$^2$, current efficiency of 4.6 cd/A, and power efficiency of 1.95 lm/W at a driving voltage of 7 V.

Comparison Example 1

The device fabrication procedures were the same as that in Embodiment 3. OLED was made using the following compound P3 instead of compound 110 for comparison.

The device could achieve blue emission with luminance of 289 cd/m$^2$, current efficiency of 2.4 cd/A, and power efficiency of 1.1 lm/W at a driving voltage of 7 V.

The embodiments 3 and 4 are two specific applications of the material in the present invention. The OLED devices using the invented material can achieve blue emission with higher brightness and efficiency that in the comparison example. Therefore, the stable material in the present invention is proved to give high efficiency and high color purity in electroluminescent devices.

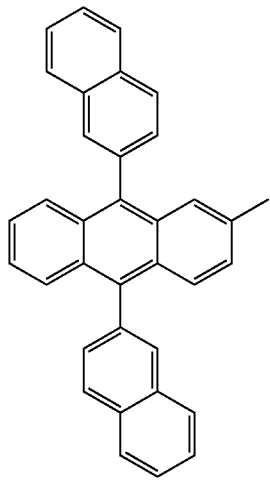

What is claimed is:

1. An organic electronic material having a structure of formula I:

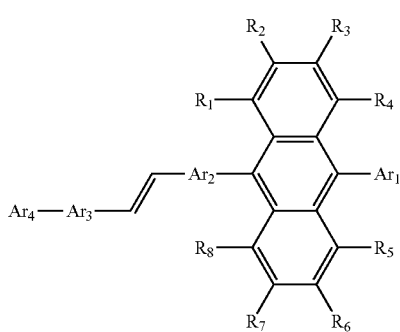

(I)

wherein,
$R_1$-$R_8$ independently represent hydrogen, halogen, cyano, nitro, C1-C8 alkyl, C1-C8 alkoxy, C2-C8 substituted or unsubstituted alkenyl, C2-C8 substituted or unsubstituted alkynyl, C1-C4 alkyl substituted or unsubstituted phenyl, or C1-C4 alkyl substituted or unsubstituted naphthyl; and $Ar_1$-$Ar_4$ independently represent C1-C4 alkyl or C6-C30 aryl substituted phenyl, C1-C4 alkyl or C6-C30 aryl substituted naphthyl, phenyl, naphthyl, C6-C30 N-aryl or C1-C4 alkyl-substituted carbazolyl, dibenzothiophenyl, dibenzofuranyl, anthryl, phenanthryl, pyrenyl, perylenyl, fluoranthenyl, (9,9-di-alkyl) fluorenyl, (9,9-dialkyl-substituted or unsubstituted aryl) fluorenyl, or 9,9-spiro-fluorenyl.

2. The organic electronic material according to claim 1, wherein:
$R_1$-$R_8$ independently represent hydrogen, halogen, C1-C4 alkyl, C1-C4 alkyl substituted or unsubstituted phenyl, or C1-C4 alkyl substituted or unsubstituted naphthyl; and $Ar_1$-$Ar_4$ independently represent phenyl, tolyl, t-butyl phenyl, naphthyl, methyl naphthalene, biphenyl, diphenyl phenyl, naphthyl phenyl, diphenyl-biphenyl, biaryl amine phenyl, N-phenyl-carbazolyl, (9,9-di-alkyl) fluorenyl, (9,9-dialkyl-substituted or unsubstituted phenyl) fluorenyl, or 9,9-spiro-fluorenyl.

3. The organic electronic material according to claim 2, wherein,
$R_1$, $R_4$, $R_5$, and $R_8$ are hydrogen, $R_2$, $R_3$, $R_6$, and $R_7$ independently represent hydrogen, fluorine, methyl, ethyl, propyl, isopropyl, tert-butyl, phenyl, or naphthyl; and $Ar_1$-$Ar_4$ independently represent phenyl, tolyl, naphthyl, methyl naphthyl, biphenyl, diphenyl phenyl, naphthyl phenyl, diphenyl-biphenyl, (9,9-di-alkyl) fluorenyl, (9,9-dimethyl-substituted or unsubstituted phenyl) fluorenyl, or 9,9-spiro-fluorenyl.

4. The organic electronic material according to claim 3, wherein:
$Ar_2$, $Ar_3$, and $Ar_4$ independently represent phenyl, naphthyl, or biphenyl, and $Ar_1$ is phenyl, naphthyl, biphenyl, diphenyl phenyl, naphthyl phenyl, diphenyl-biphenyl, (9,9-di-alkyl) fluorenyl, (9-tolyl, 9'-phenyl) fluorenyl, or 9,9-spiro-fluorenyl.

5. The organic electronic material according to claim 4, wherein:
$R_2$, $R_3$, $R_6$, and $R_7$ are hydrogen, and
$Ar_2$, $Ar_3$, and $Ar_4$ independently represent phenyl or naphthyl.

6. An organic electronic material having a structure of one of the following structures:

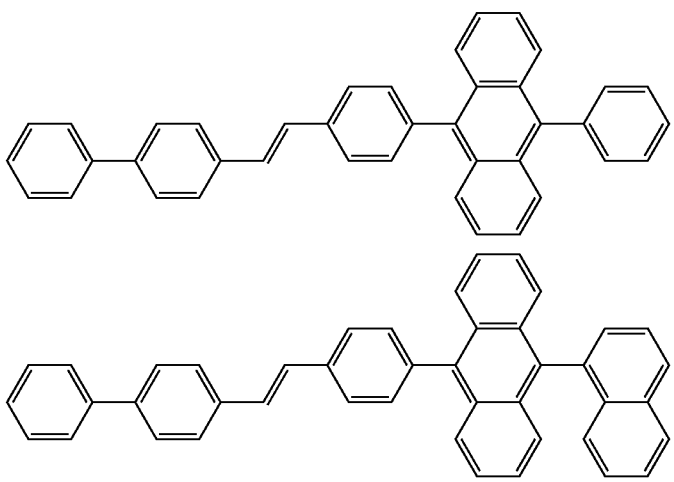

-continued
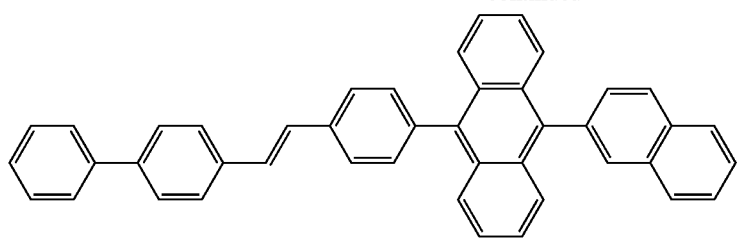
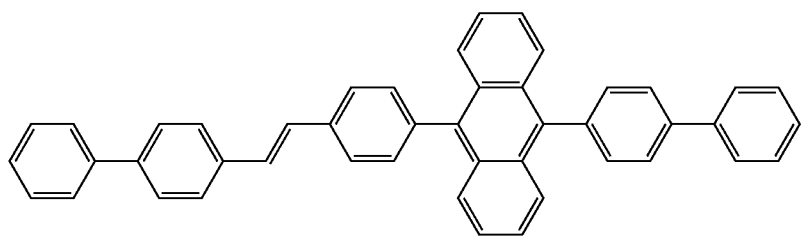
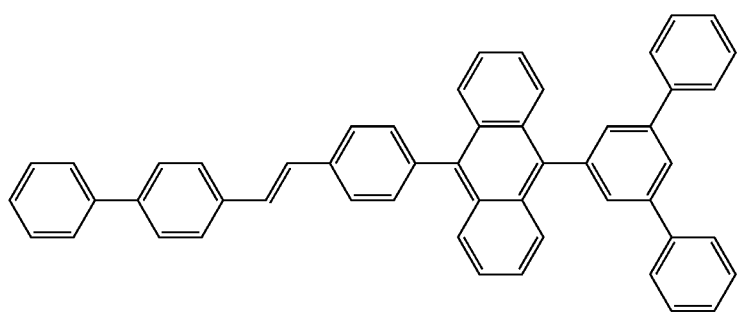
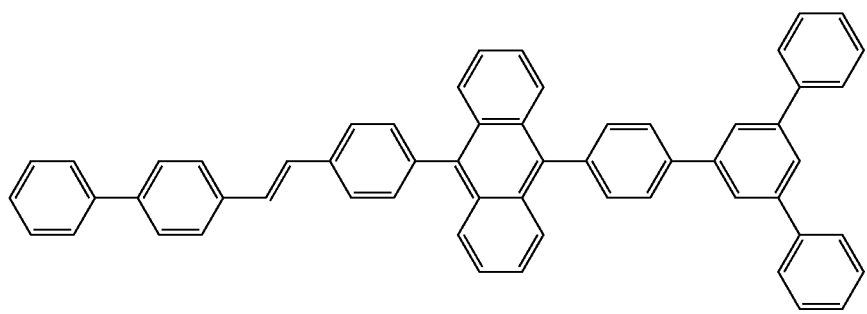
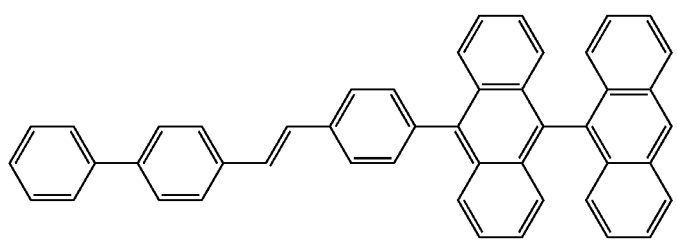
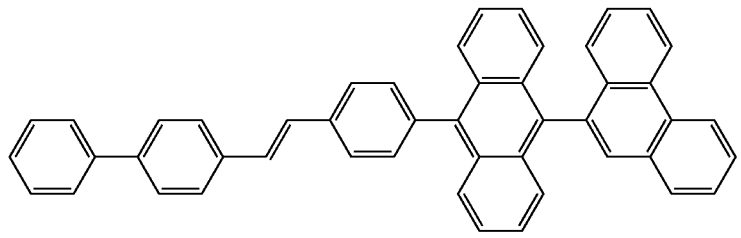

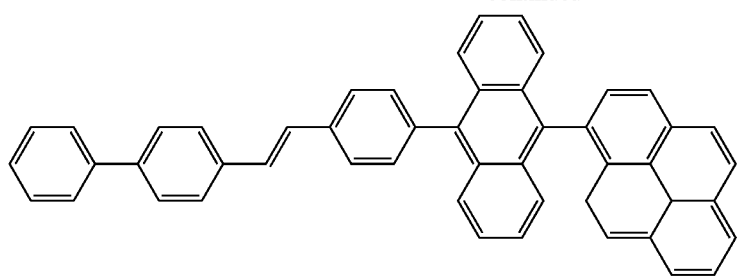
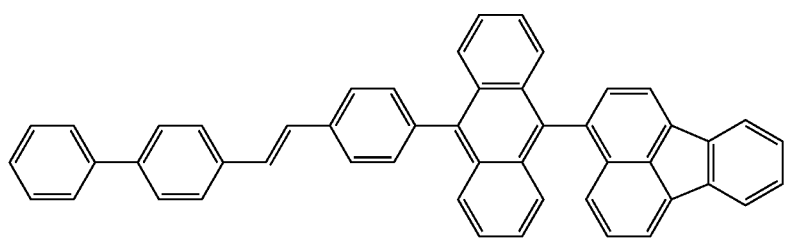
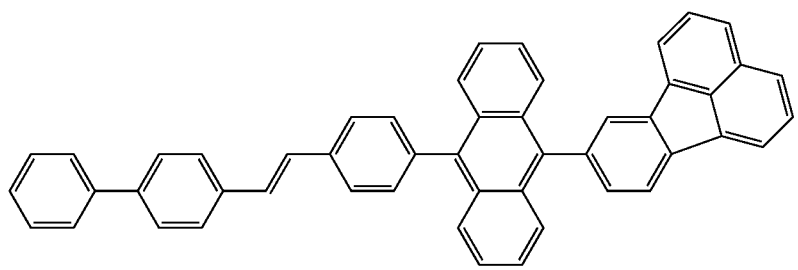
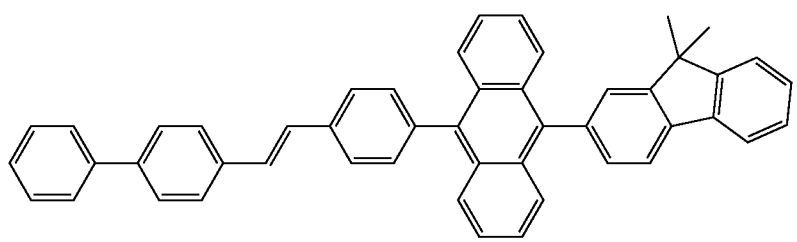
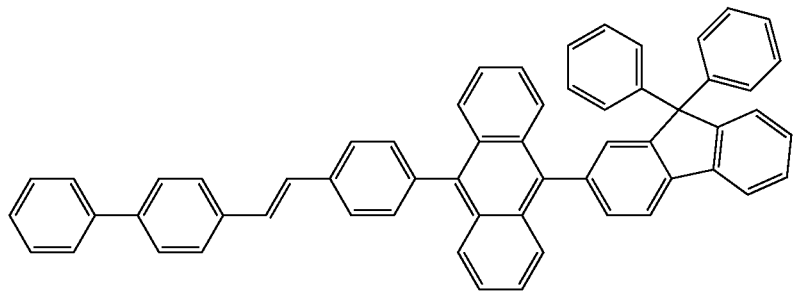
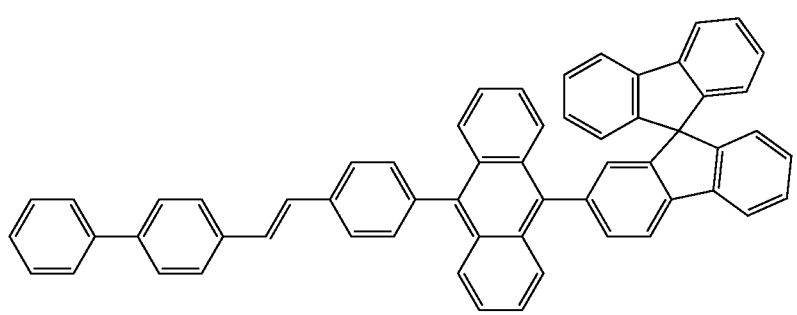

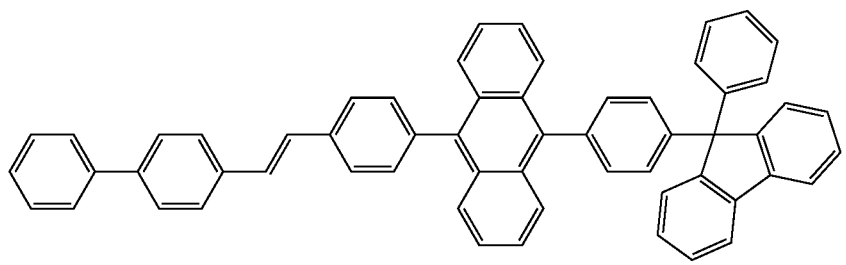
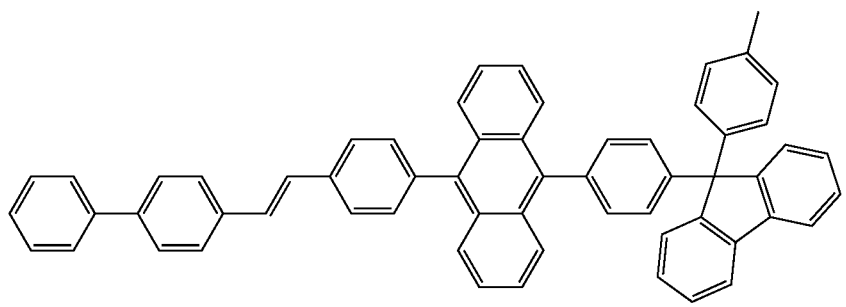
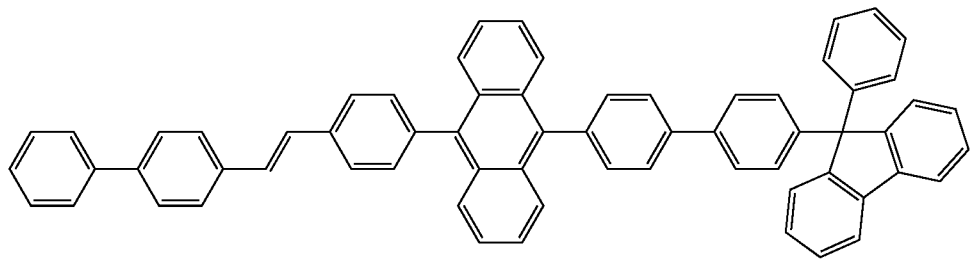
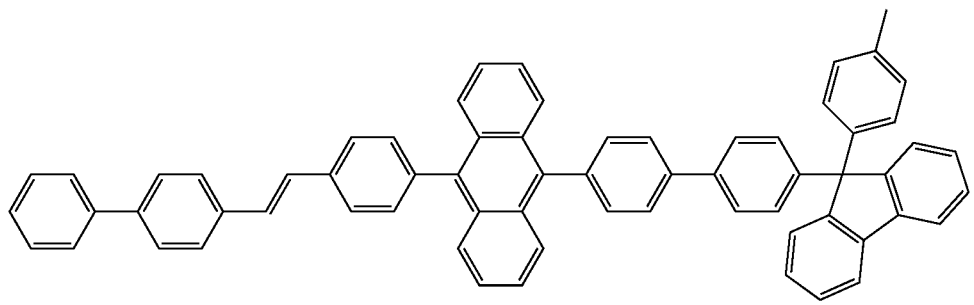
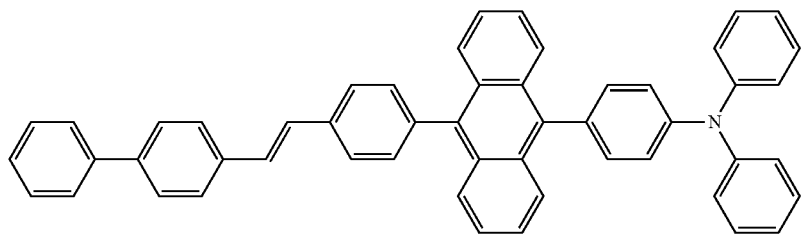
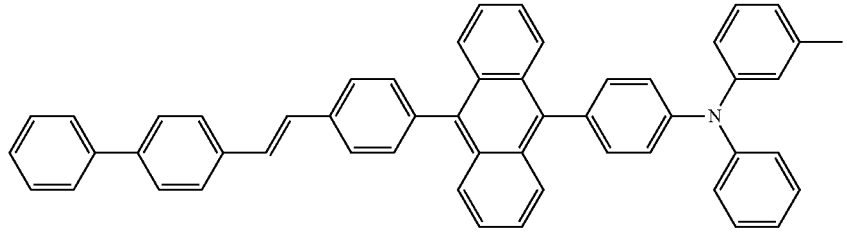

-continued
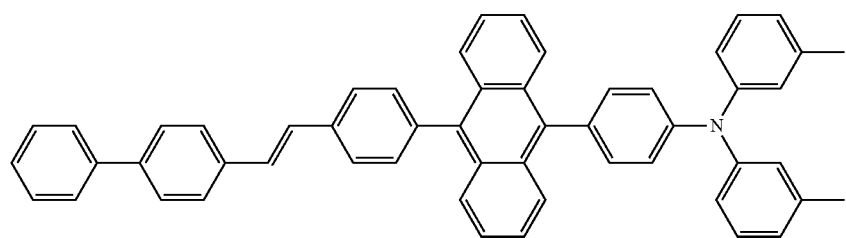
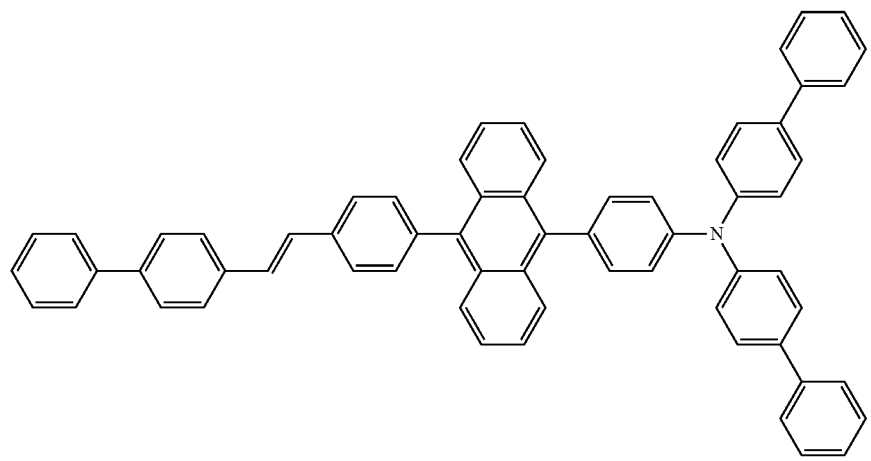
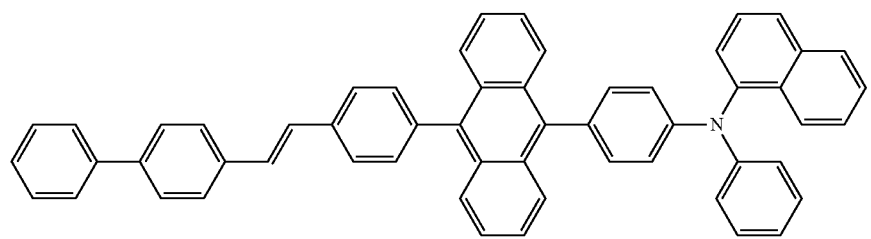
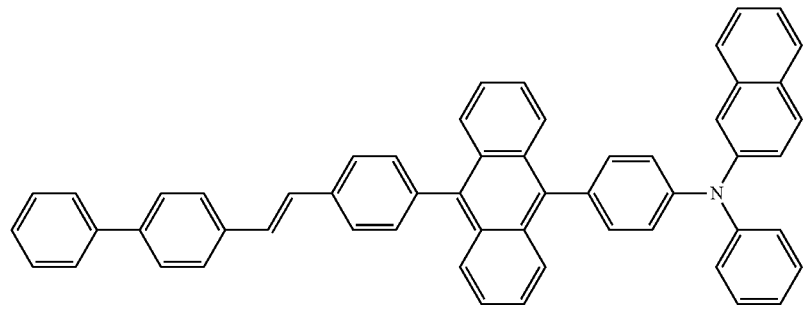
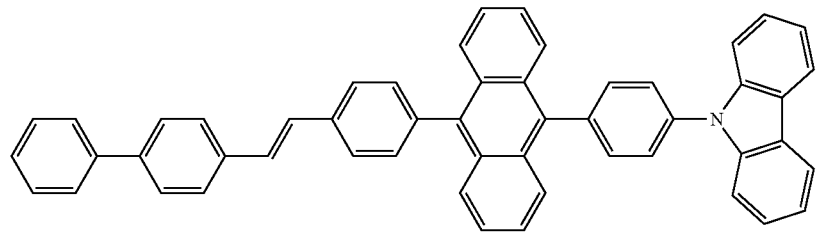

-continued
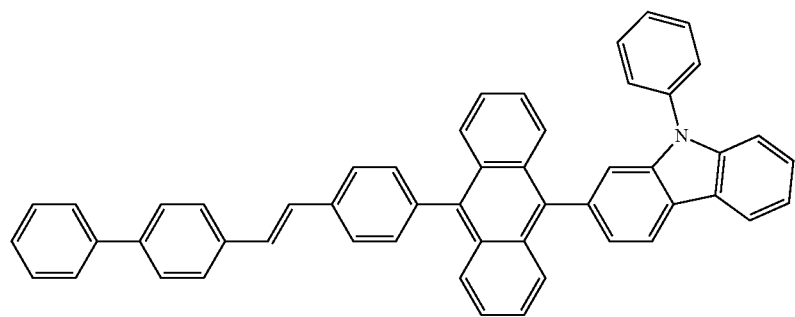
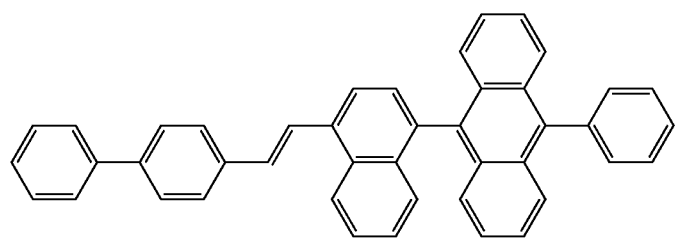
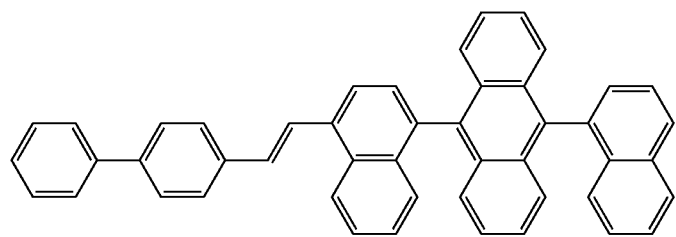
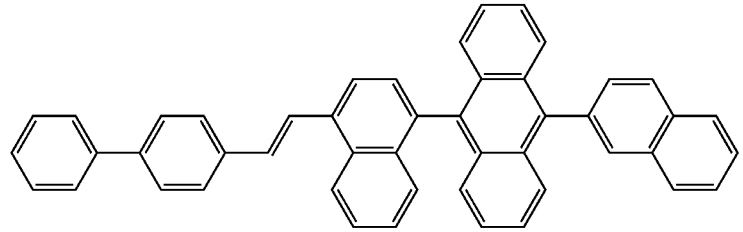
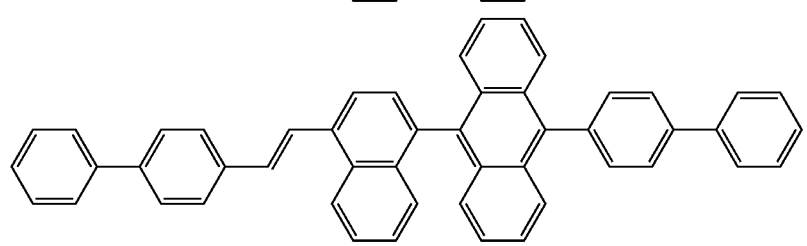
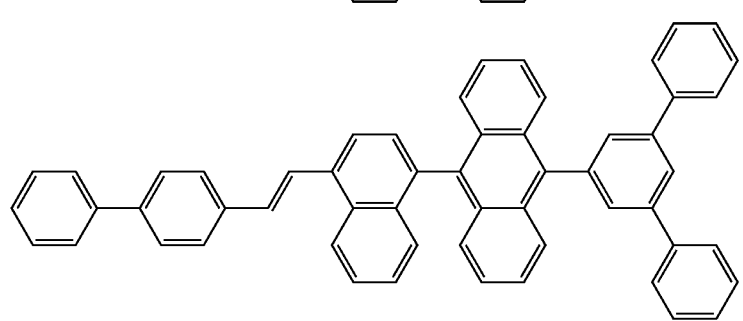

-continued
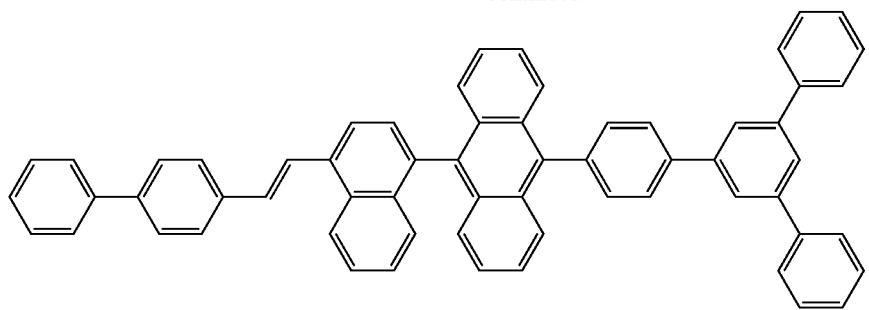
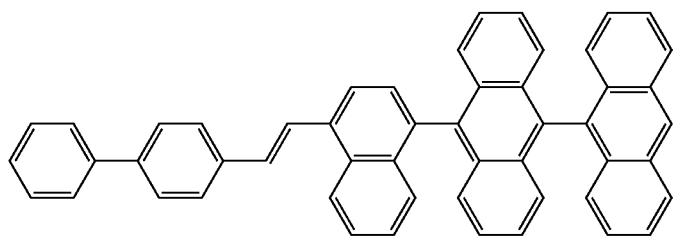
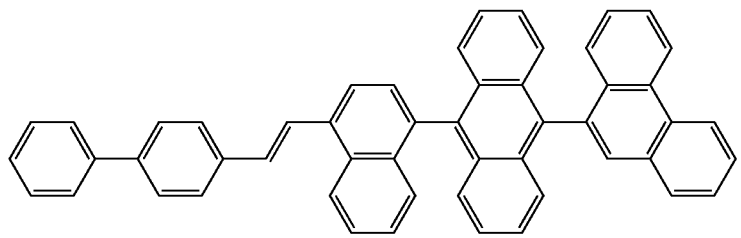
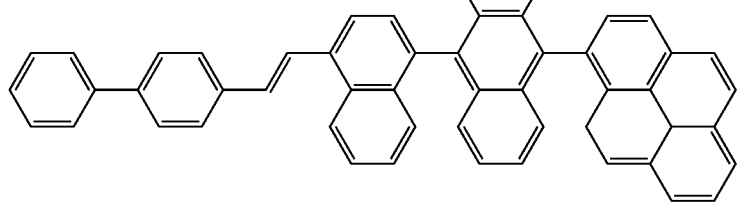
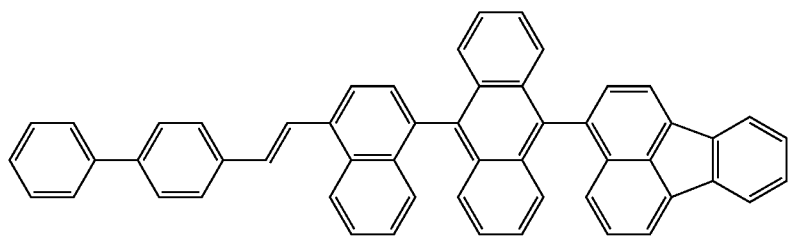
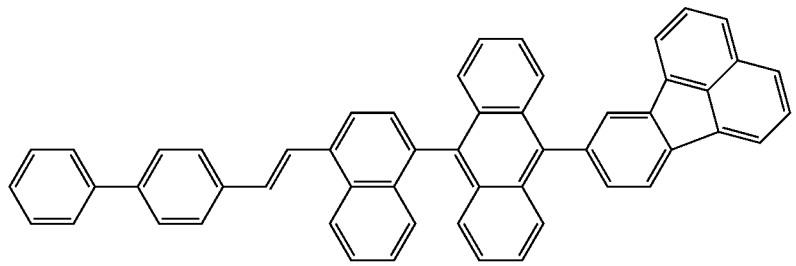

-continued
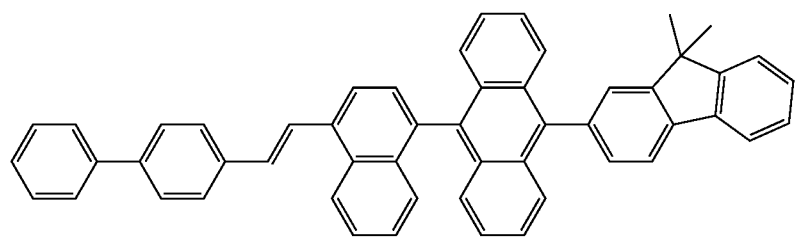
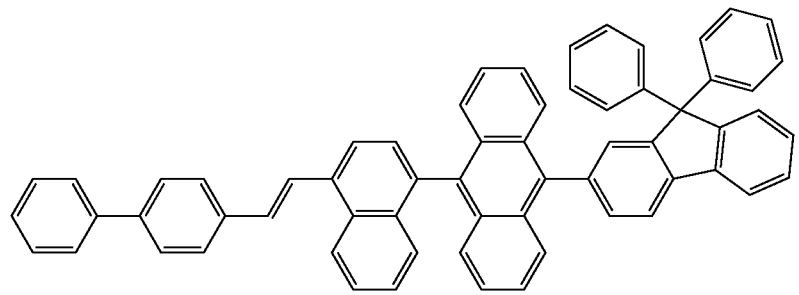
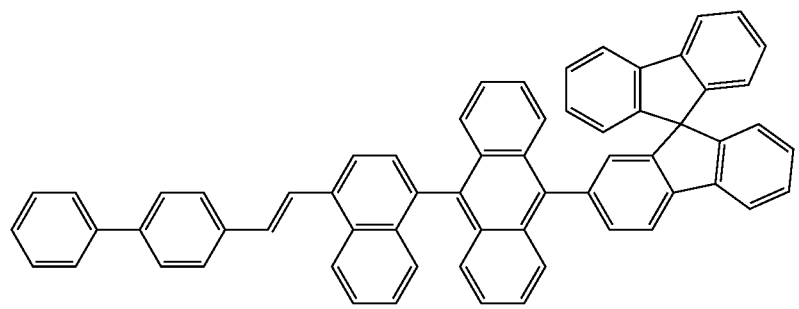
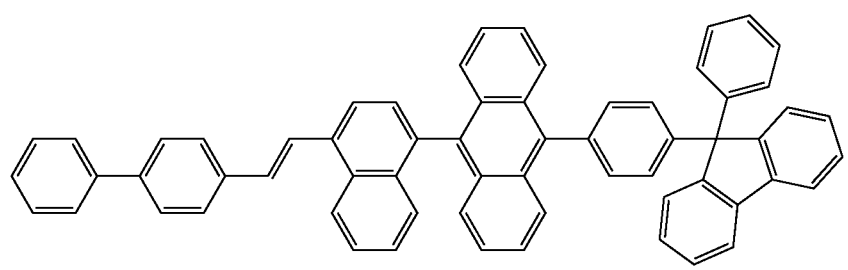
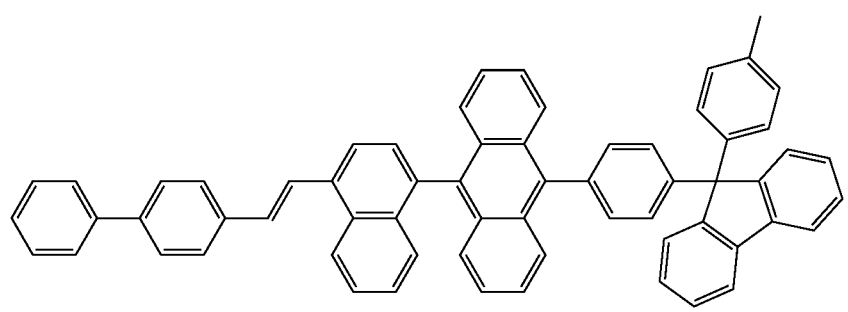
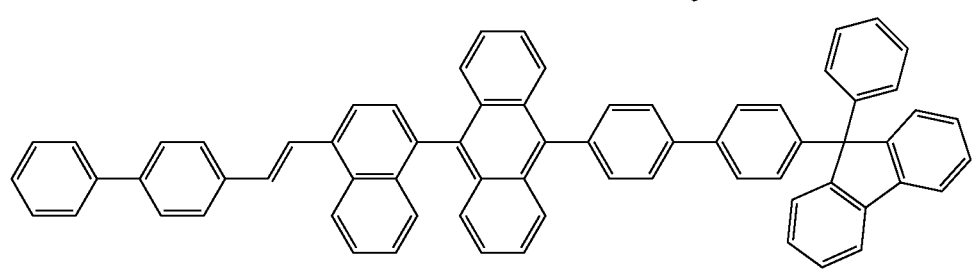

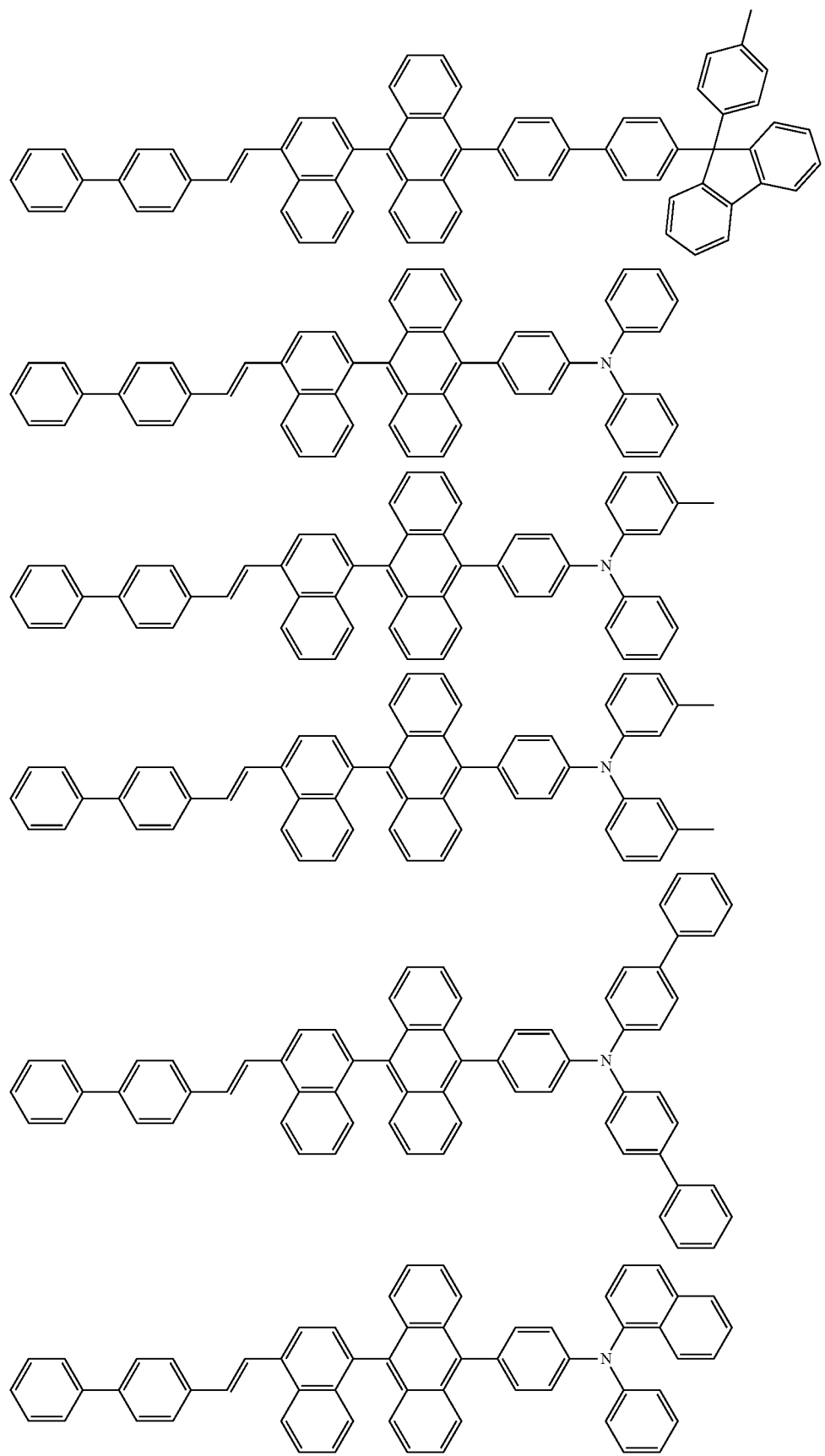

-continued
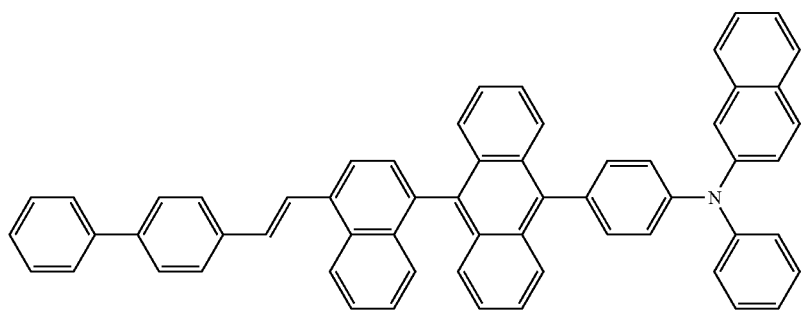
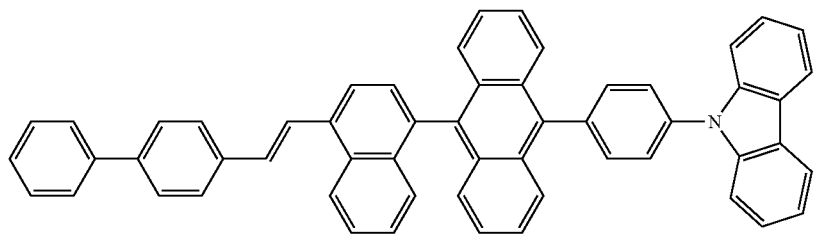
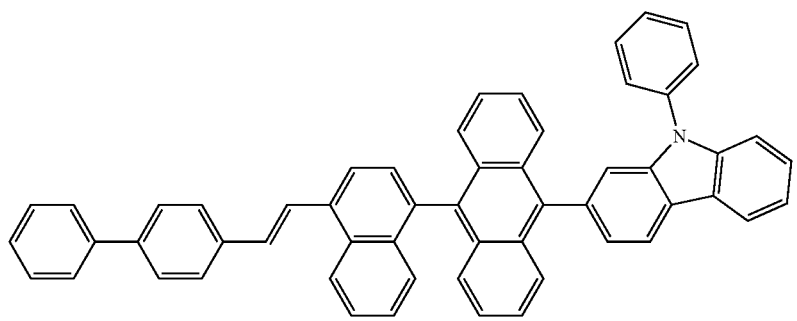
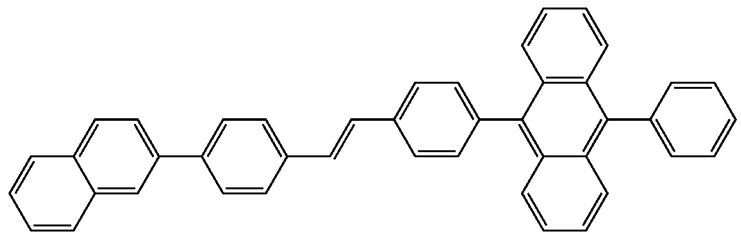
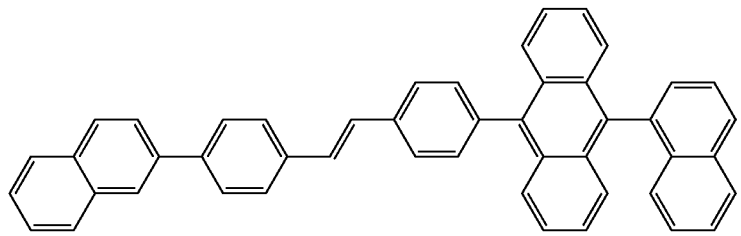
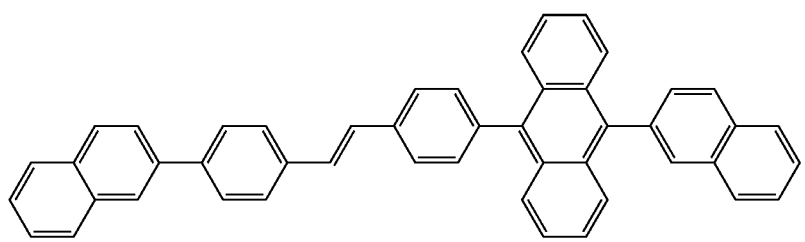

-continued
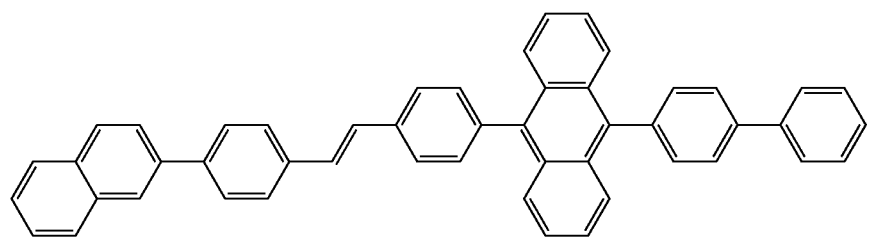
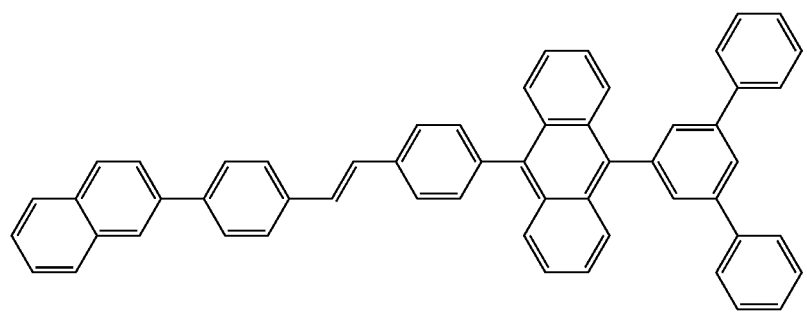
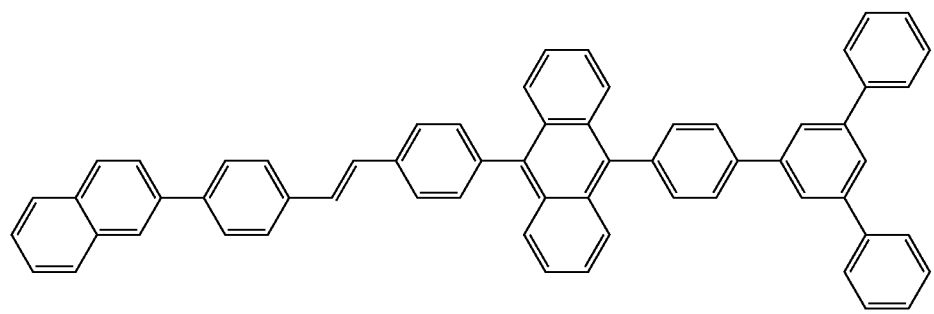
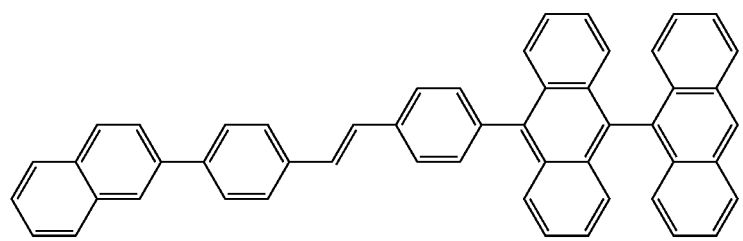
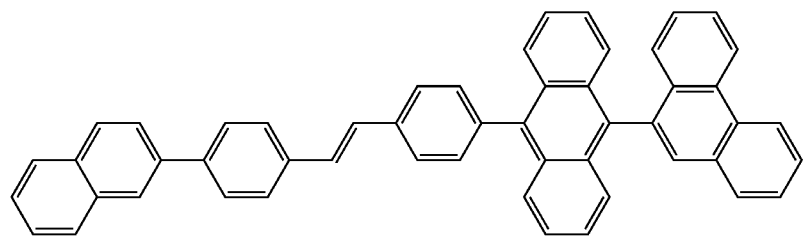
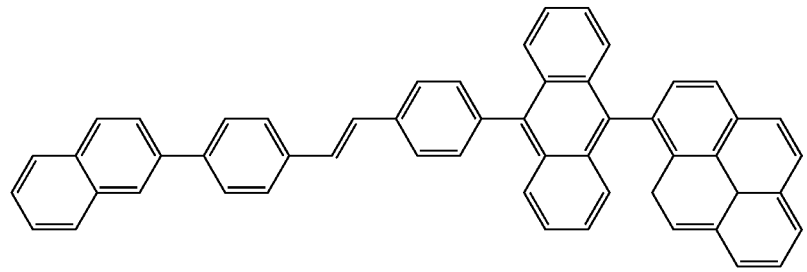

-continued
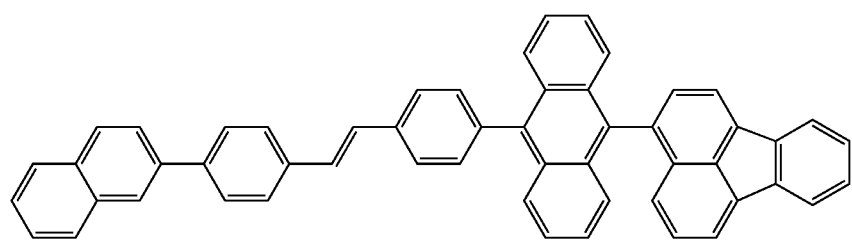
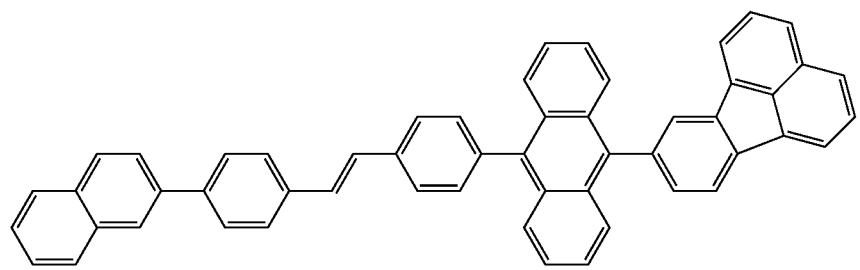
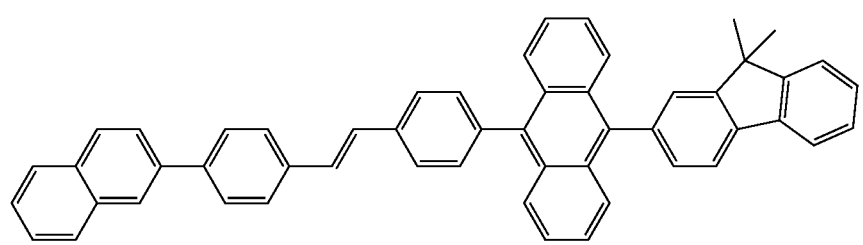
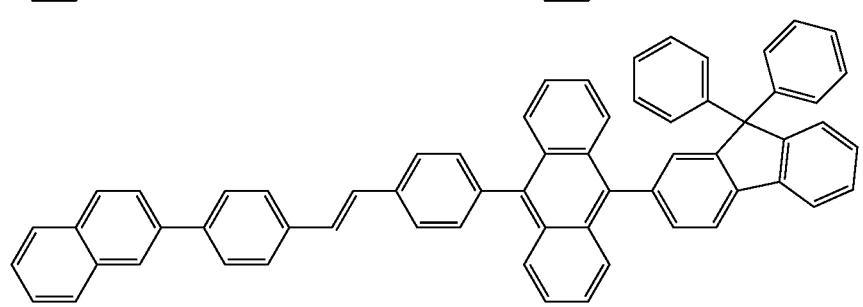
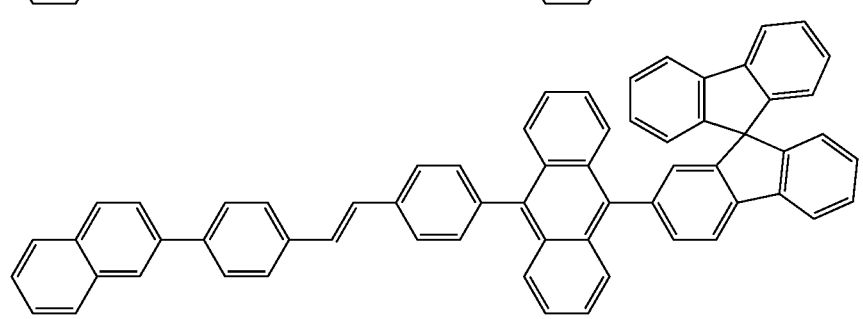
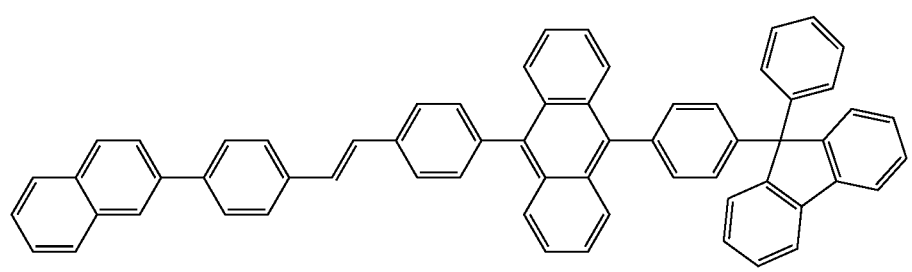

-continued
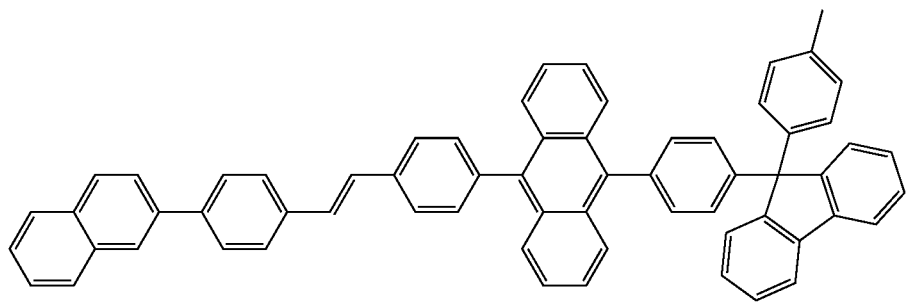
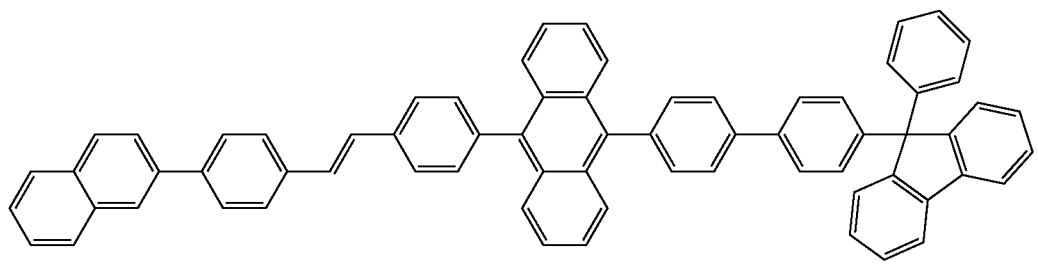
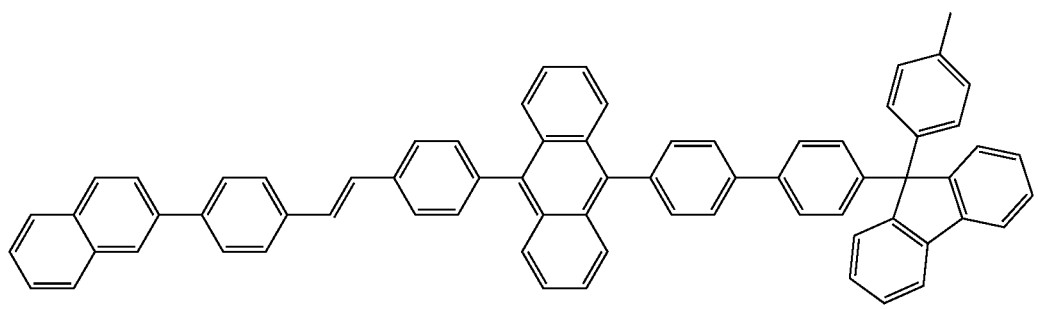
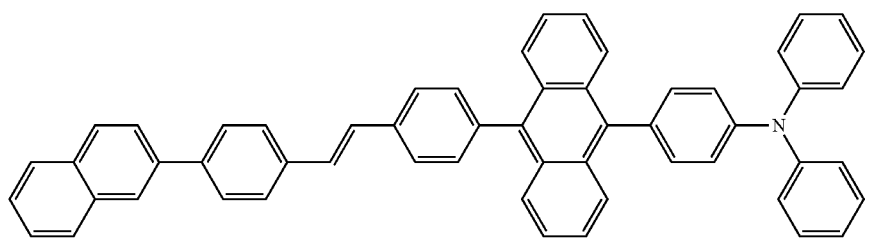
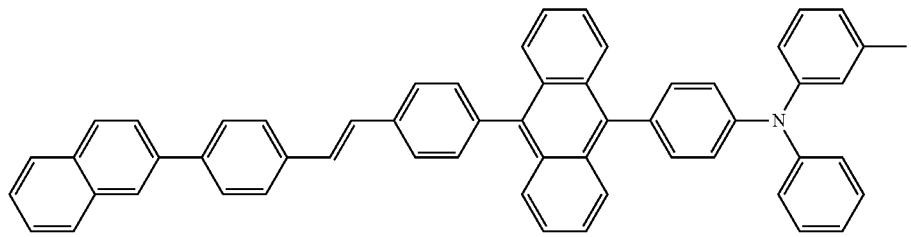
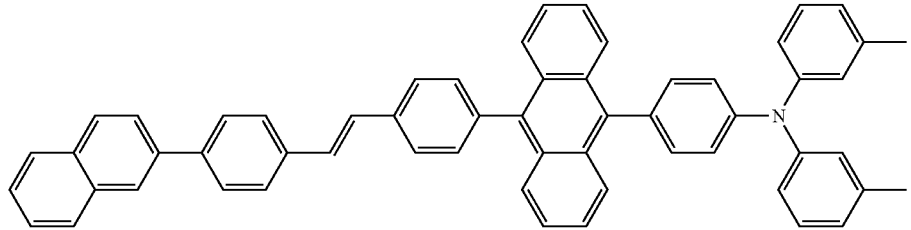

-continued
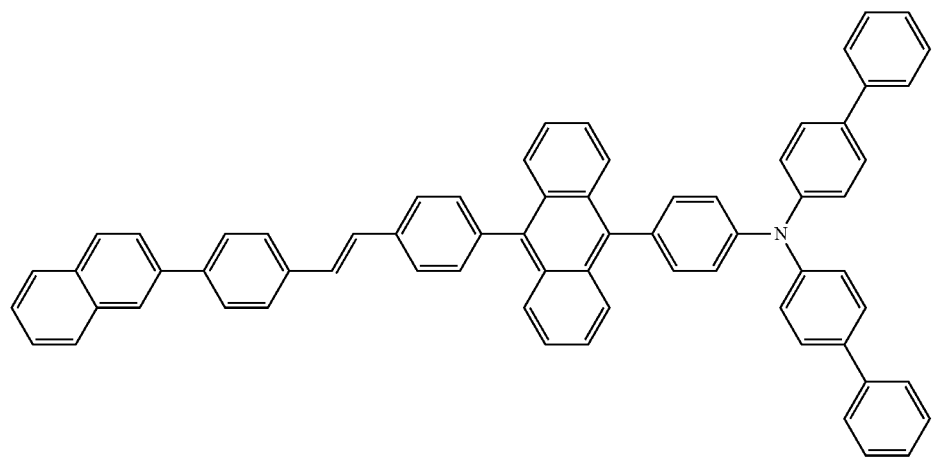
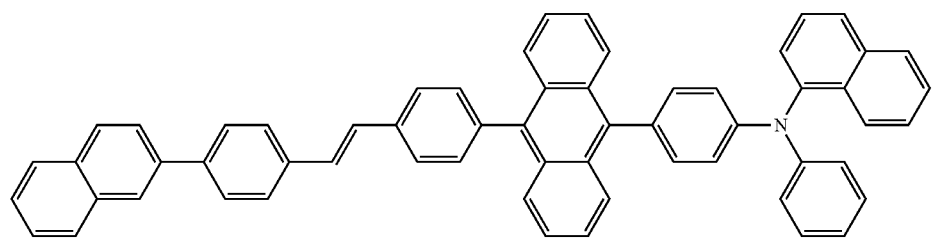
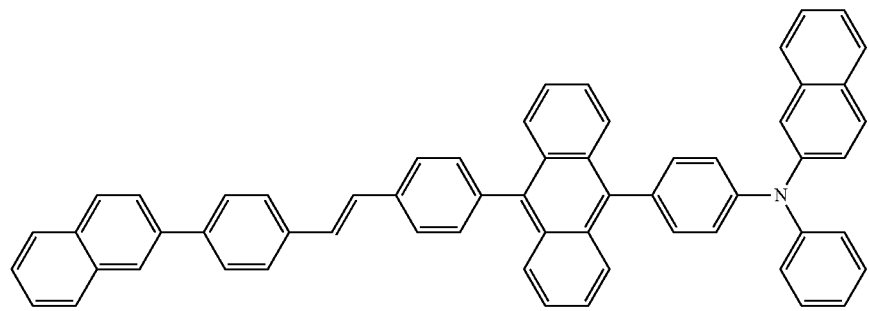
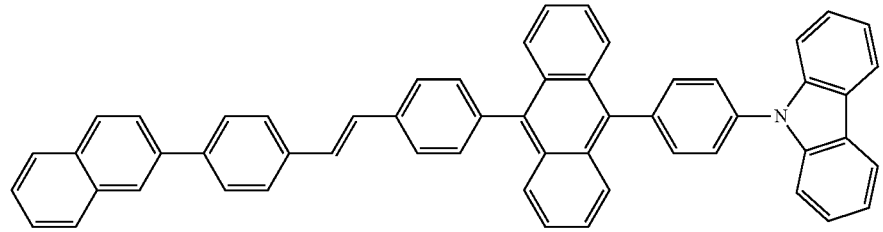
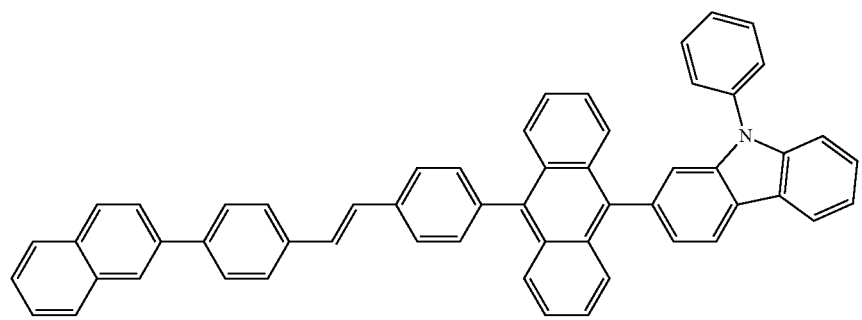

-continued
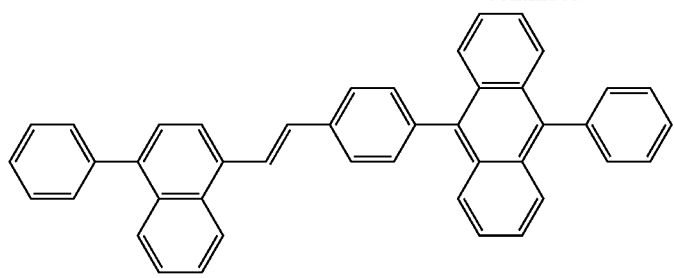
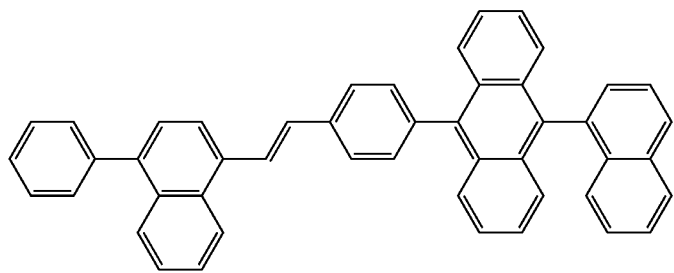
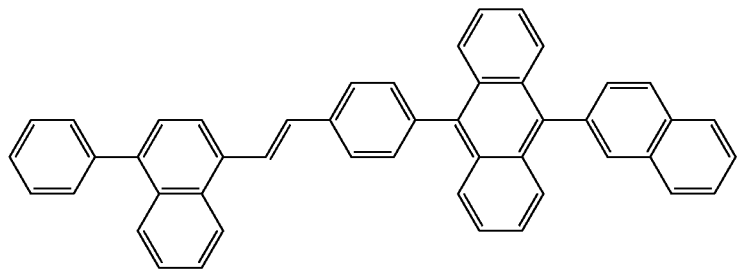
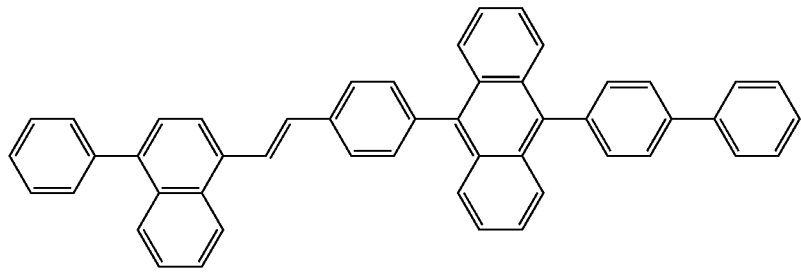
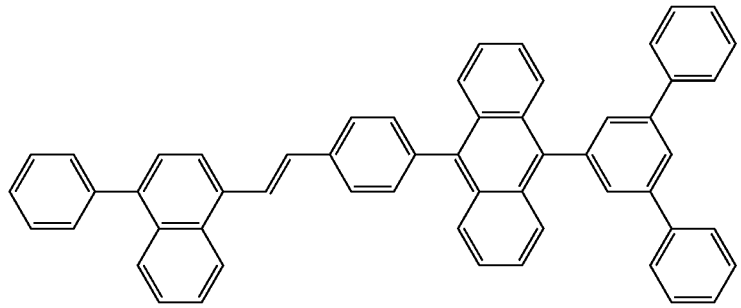
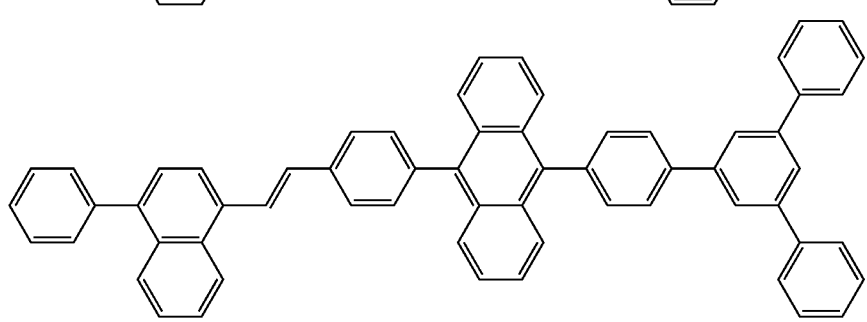

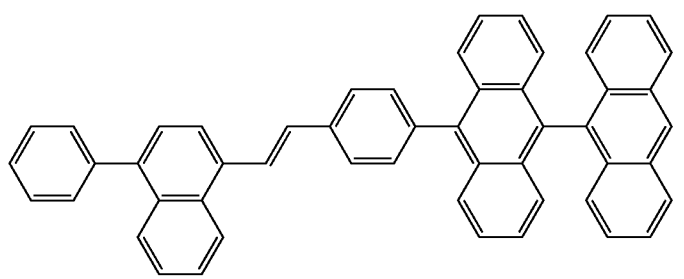
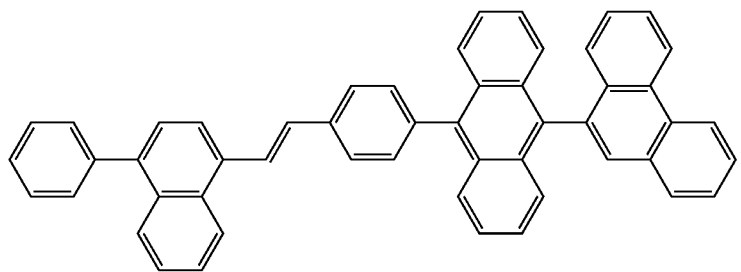
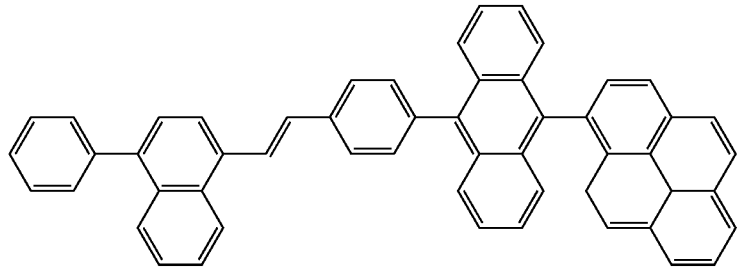
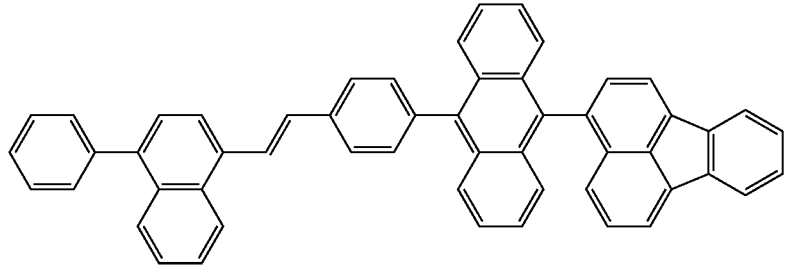
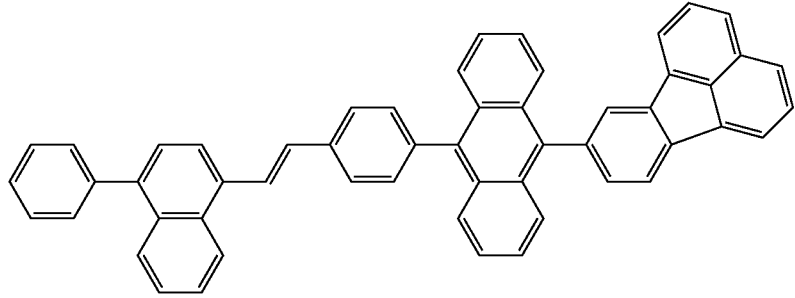
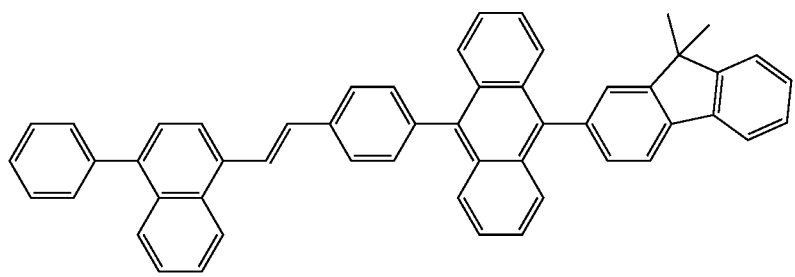

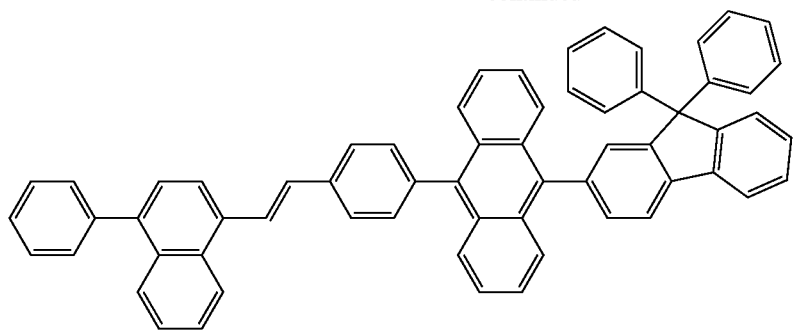
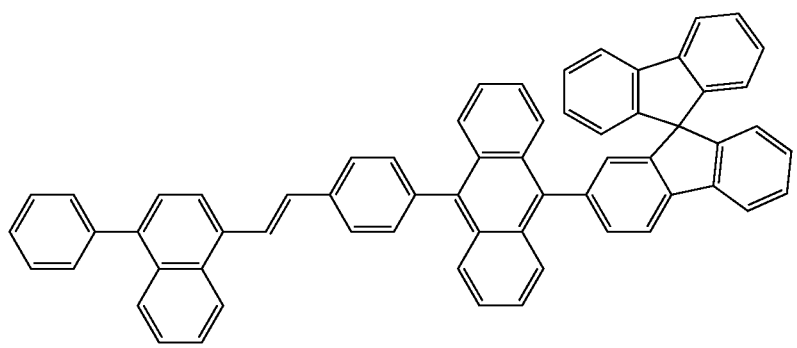
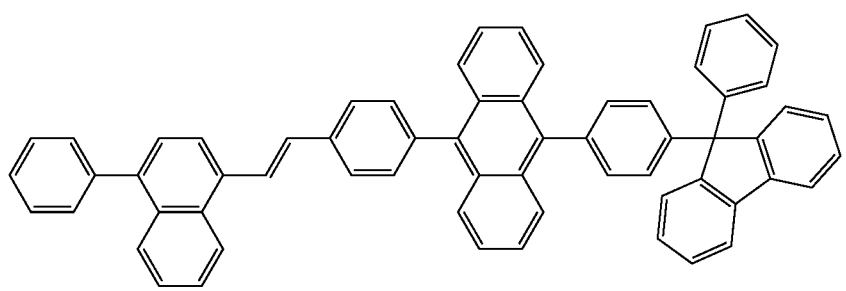
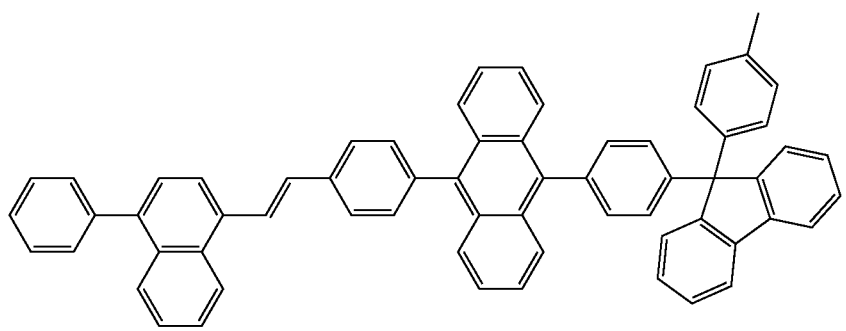
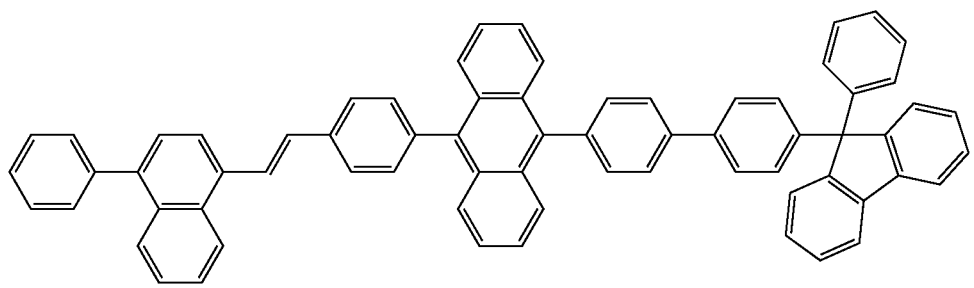

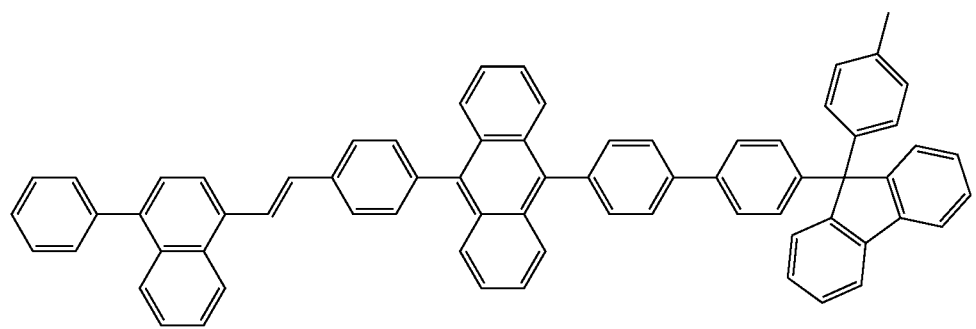
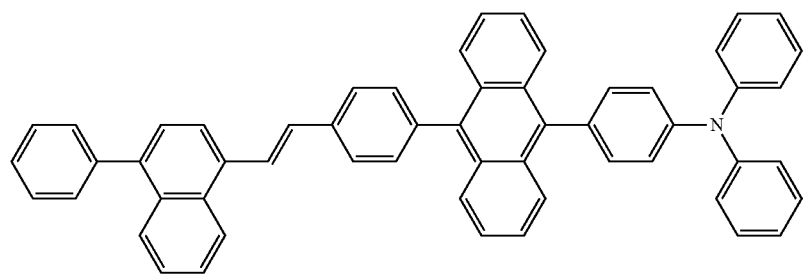
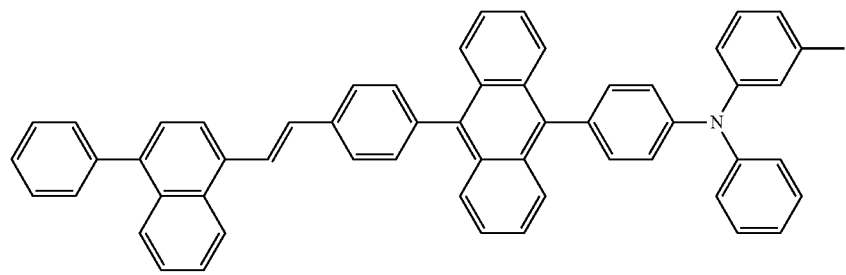
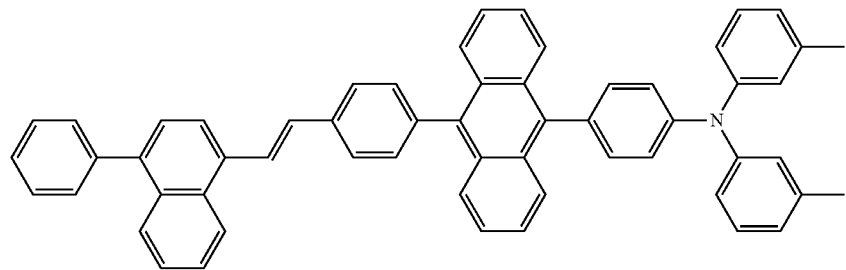
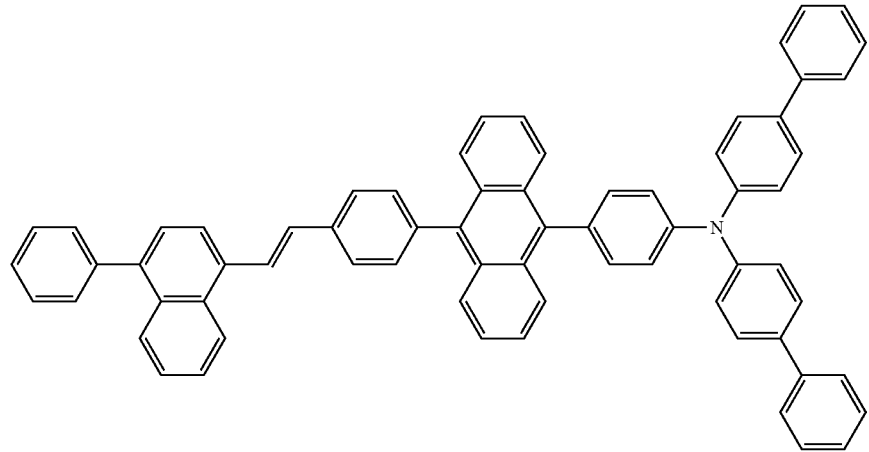

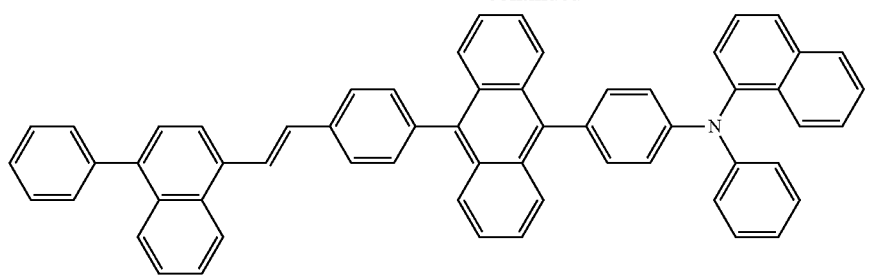
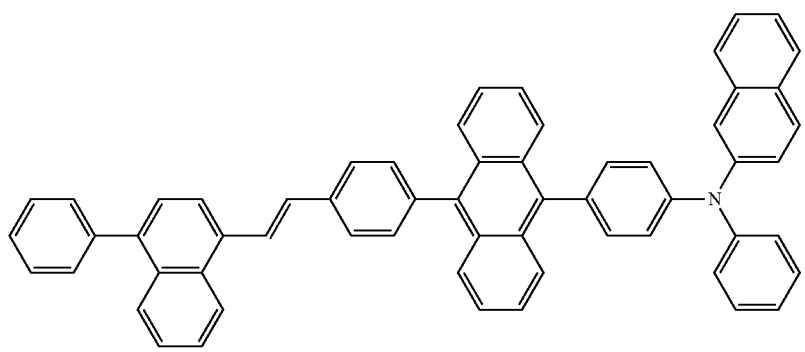
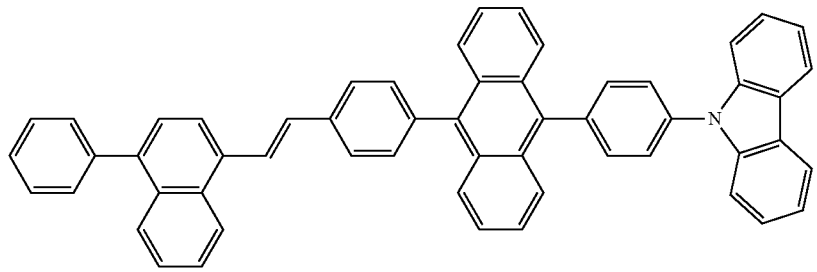
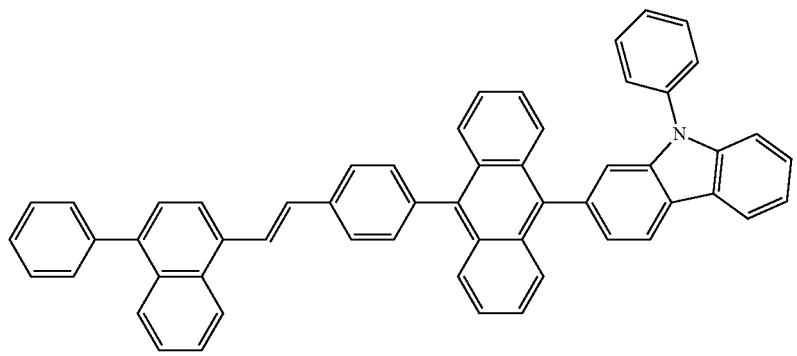
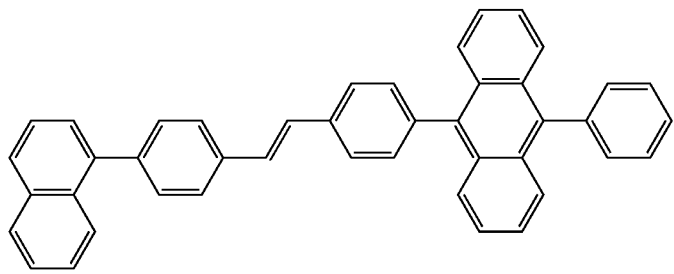

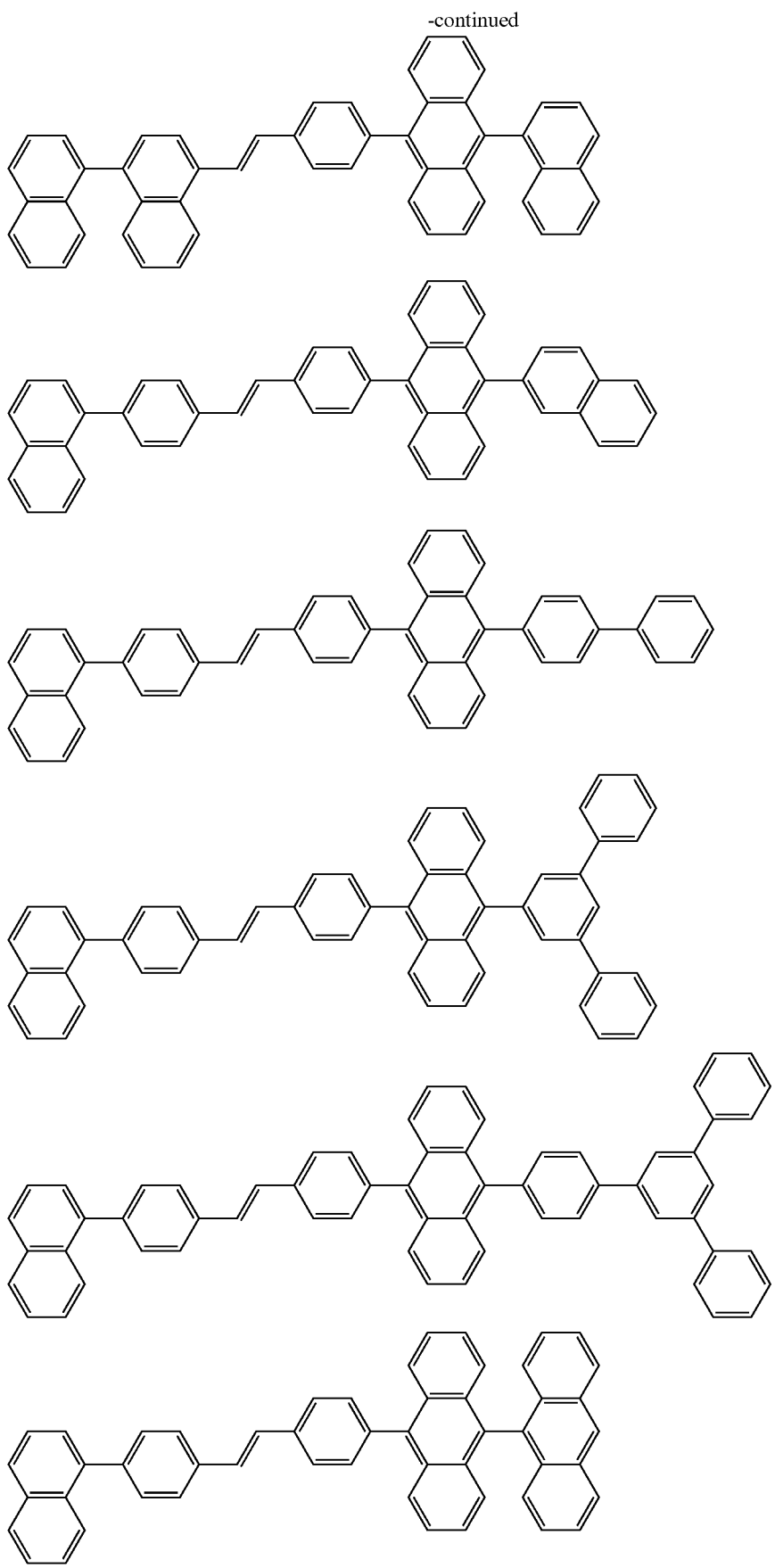

-continued
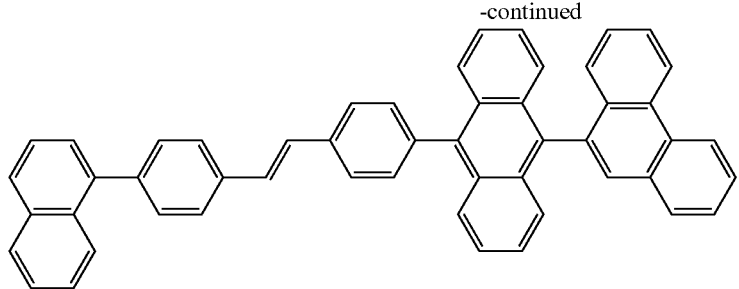
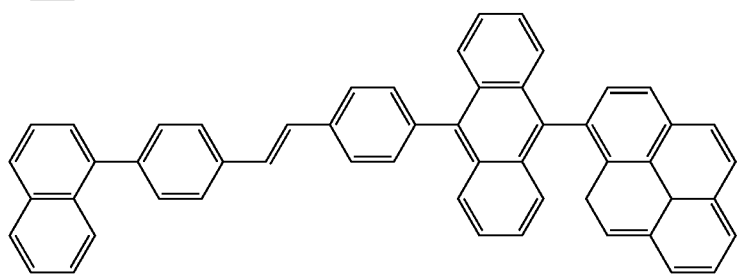
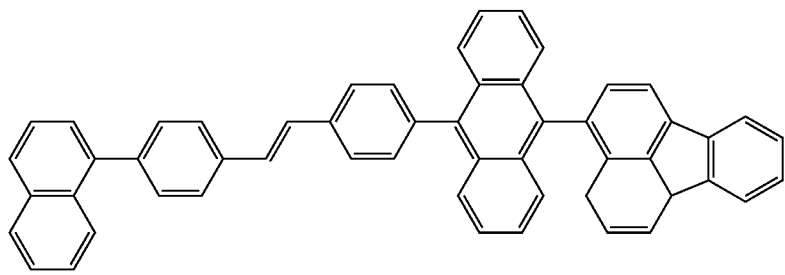
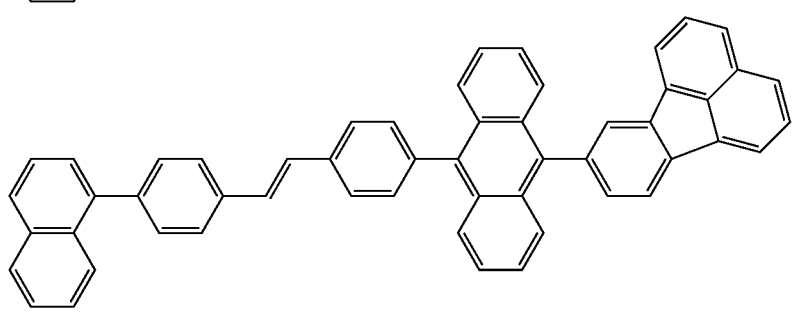
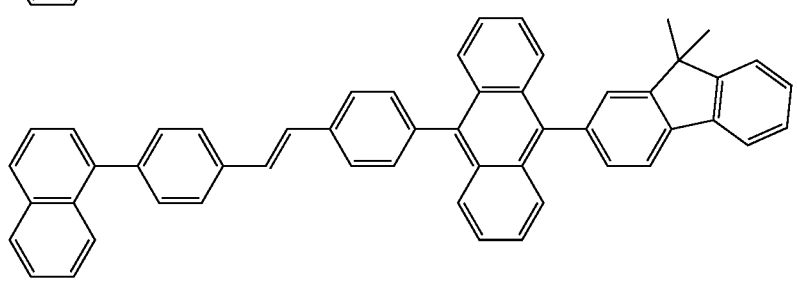
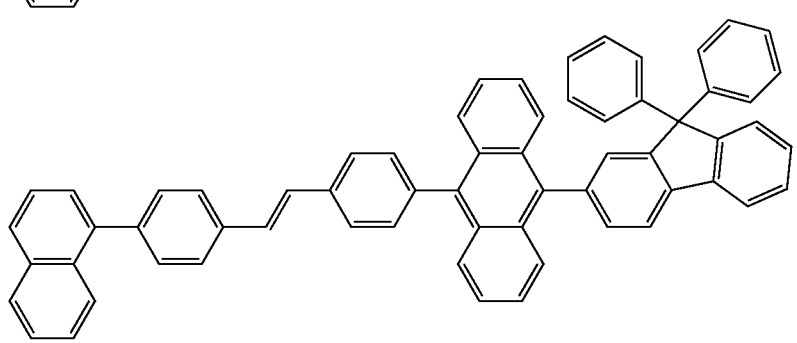

-continued
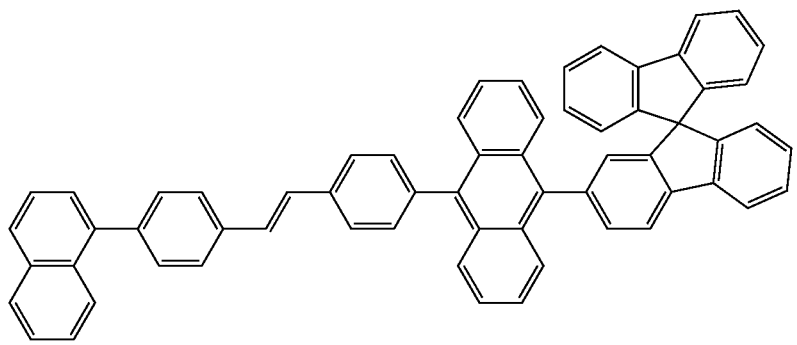
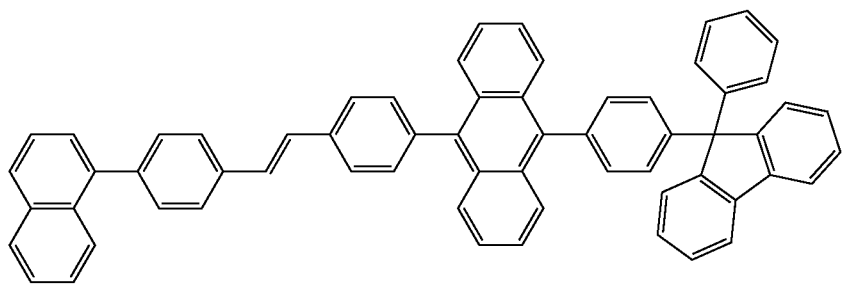
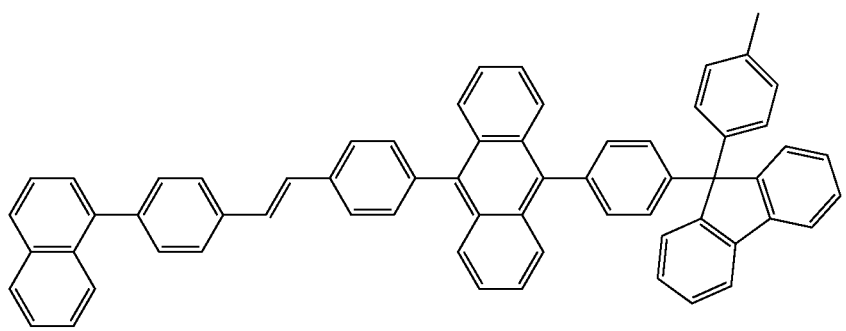
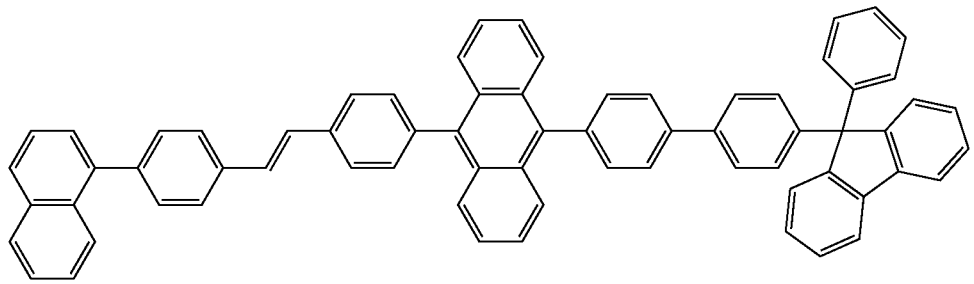
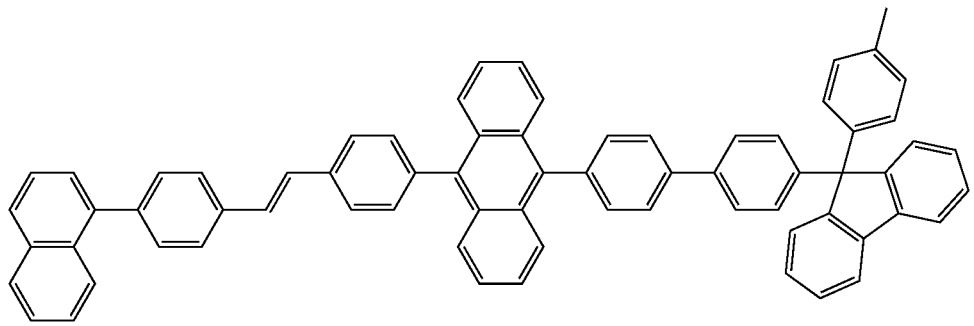

-continued
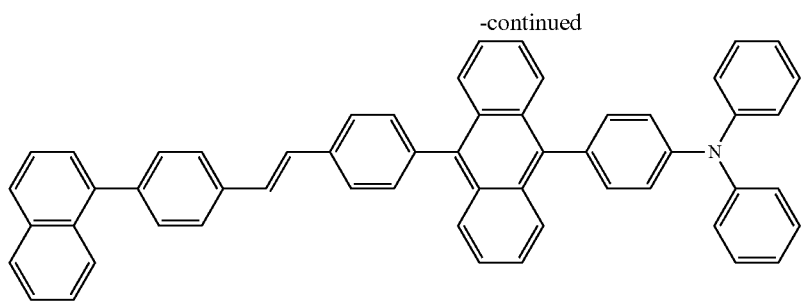
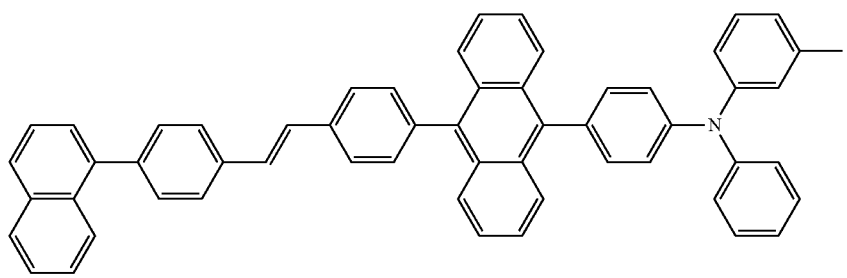
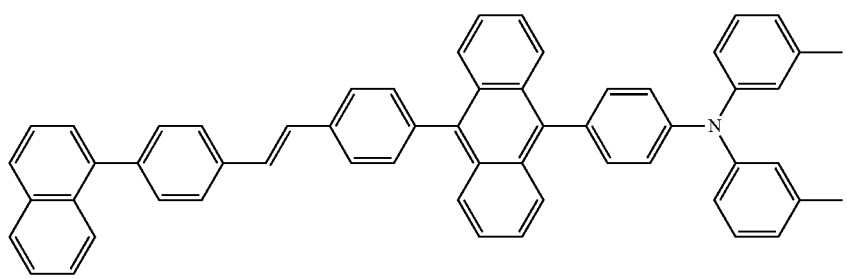
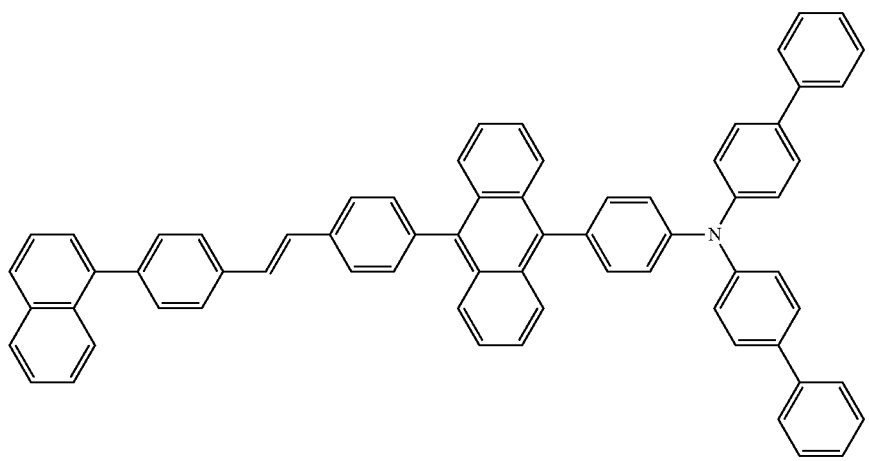
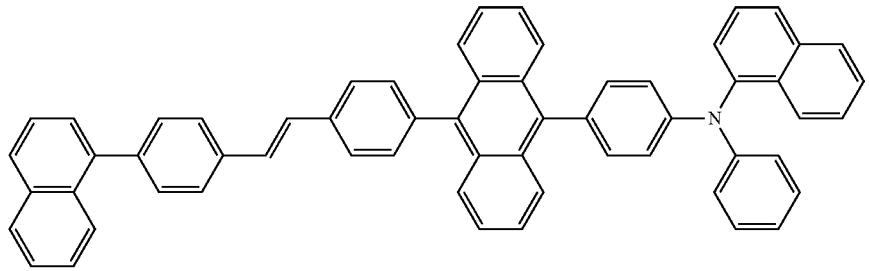

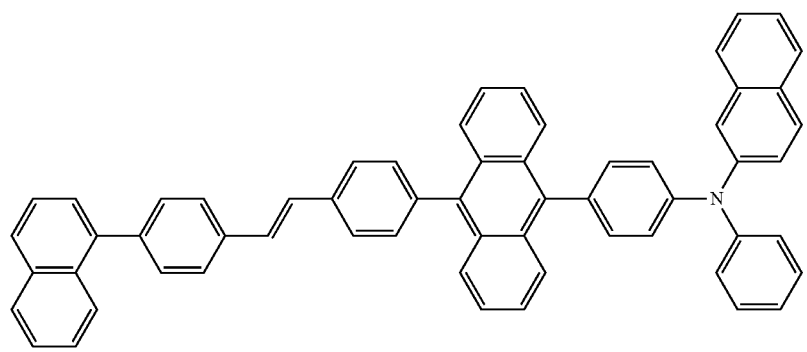
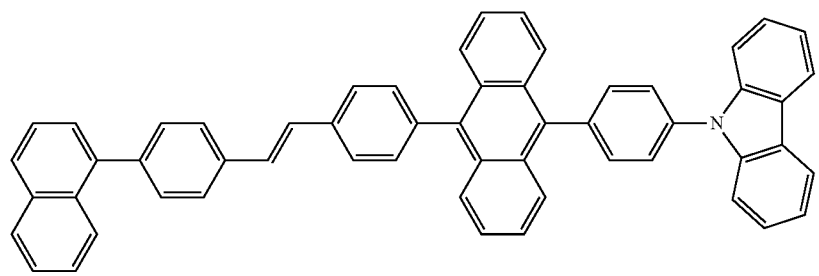
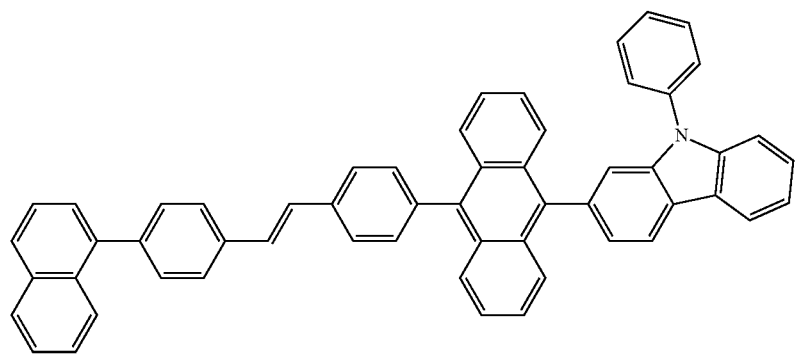
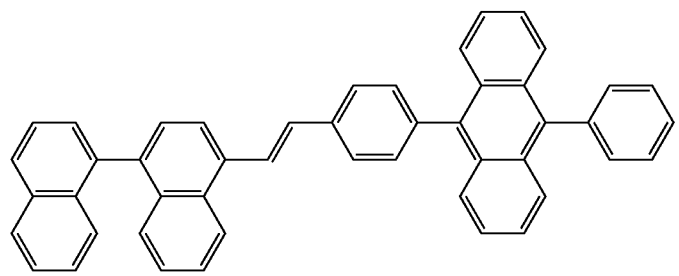
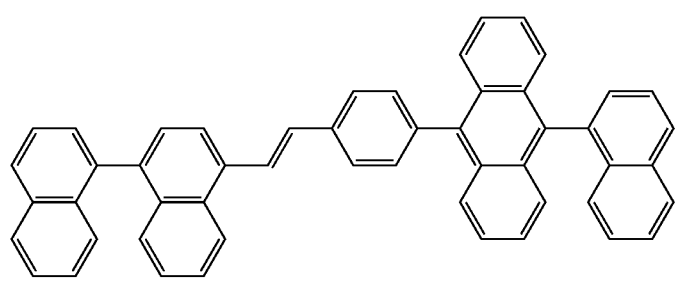

-continued
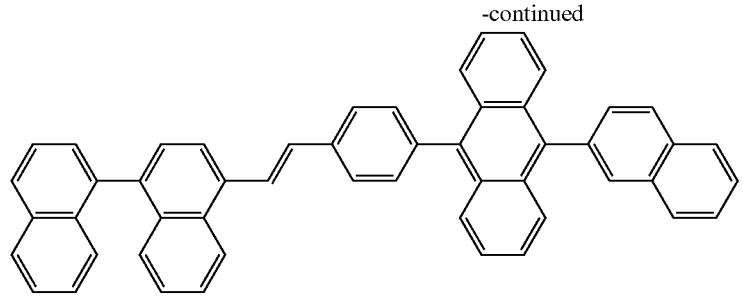
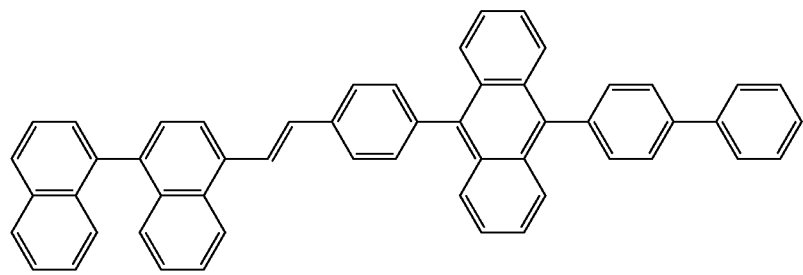
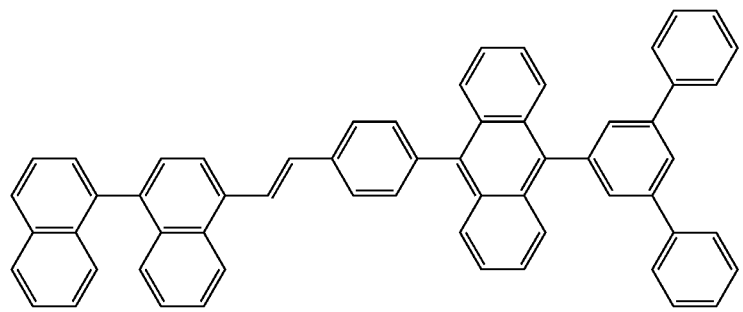
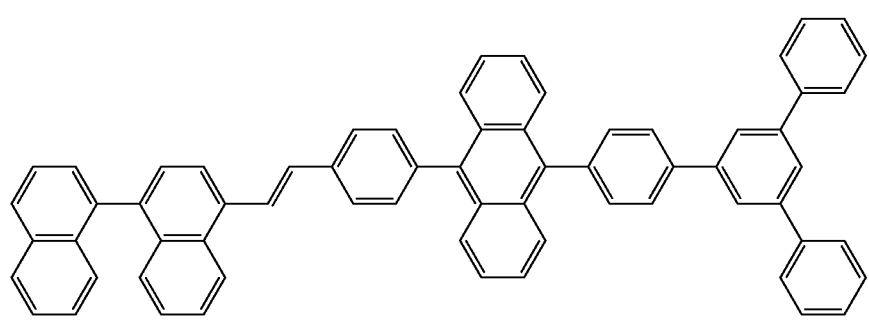
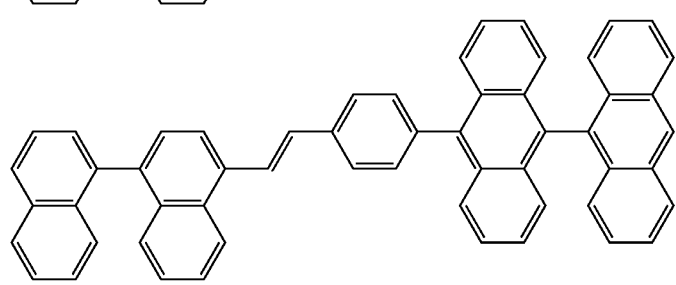
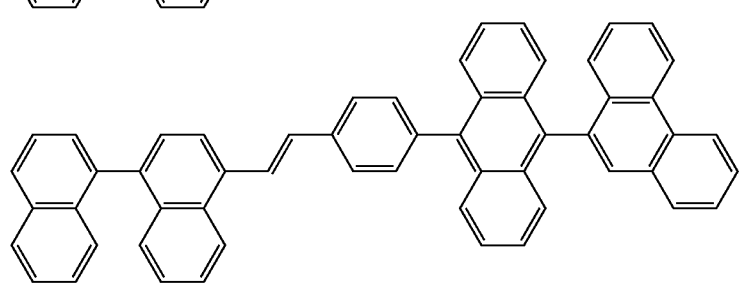

-continued
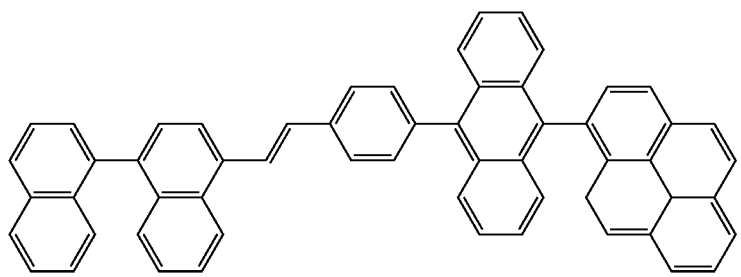
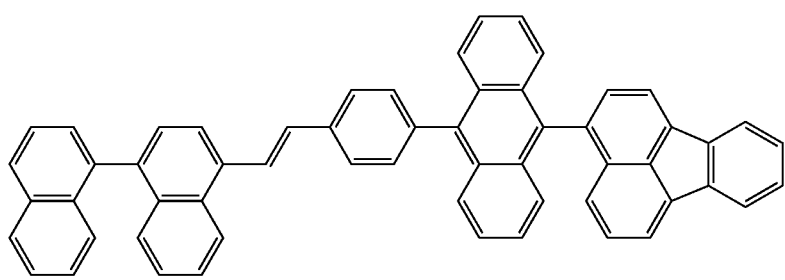
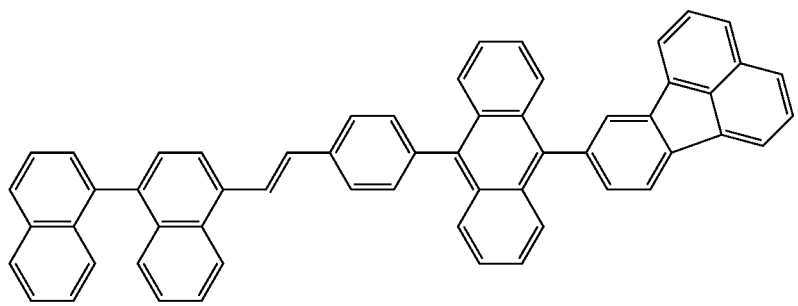
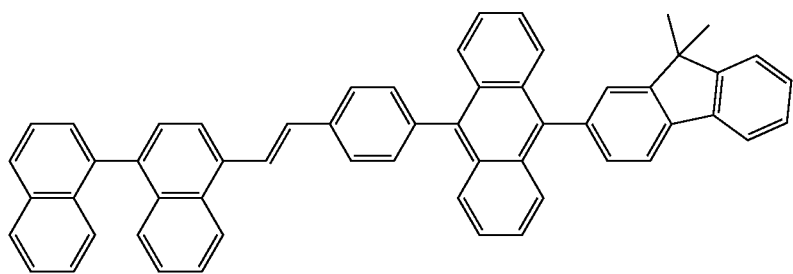
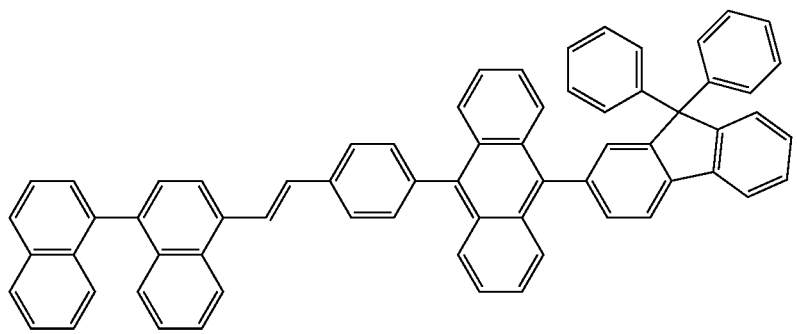

-continued
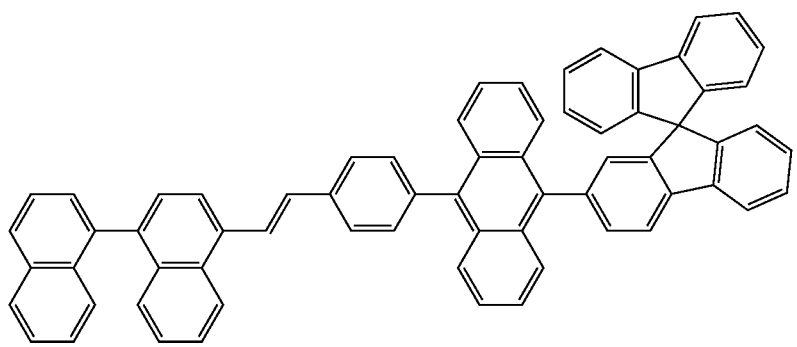
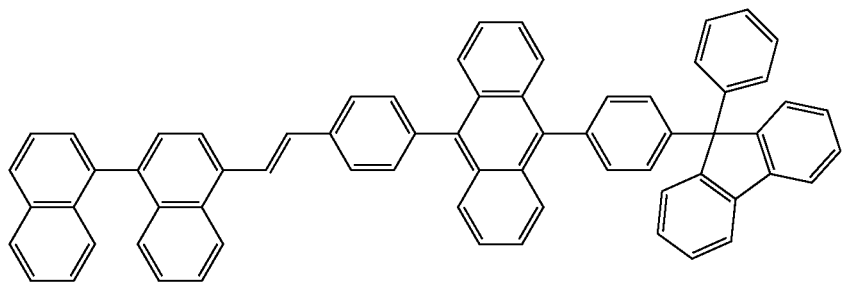
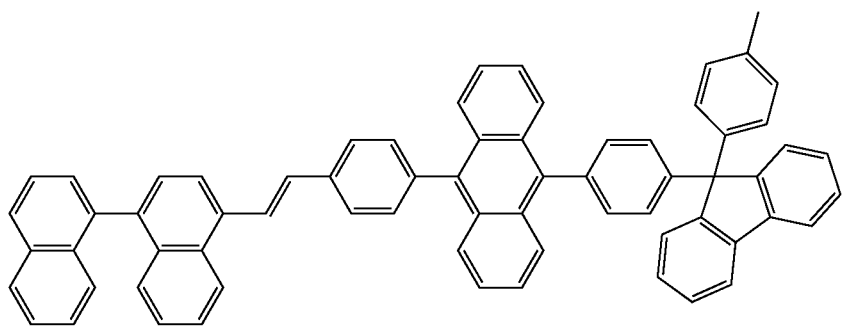
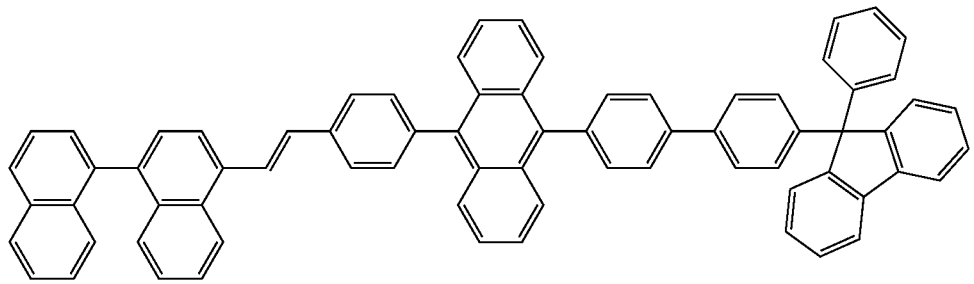
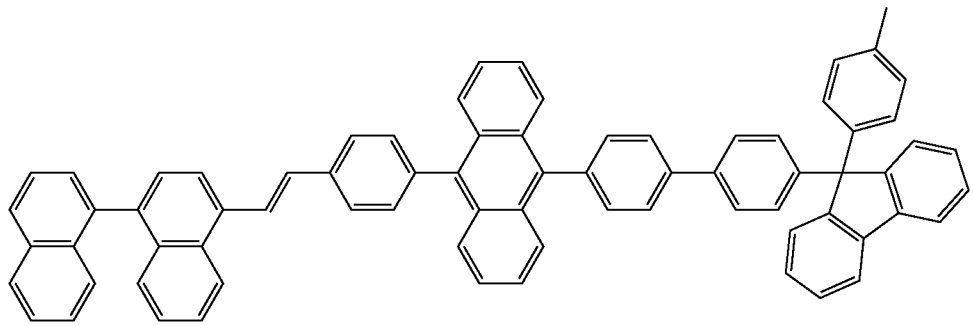

-continued
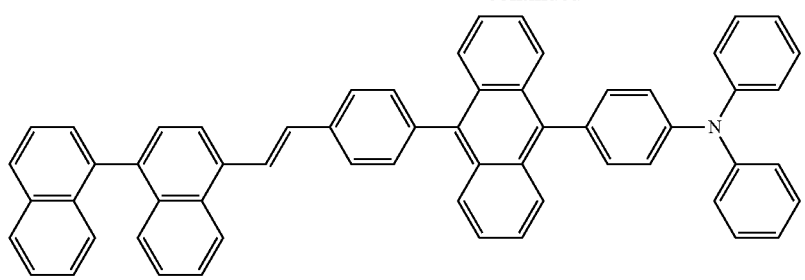
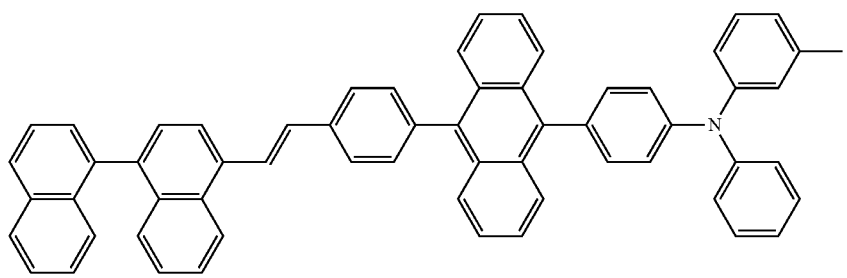
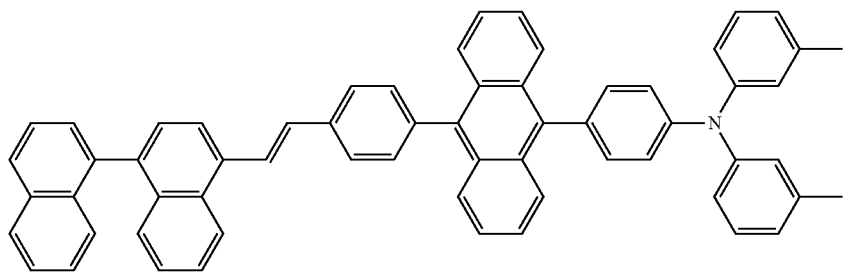
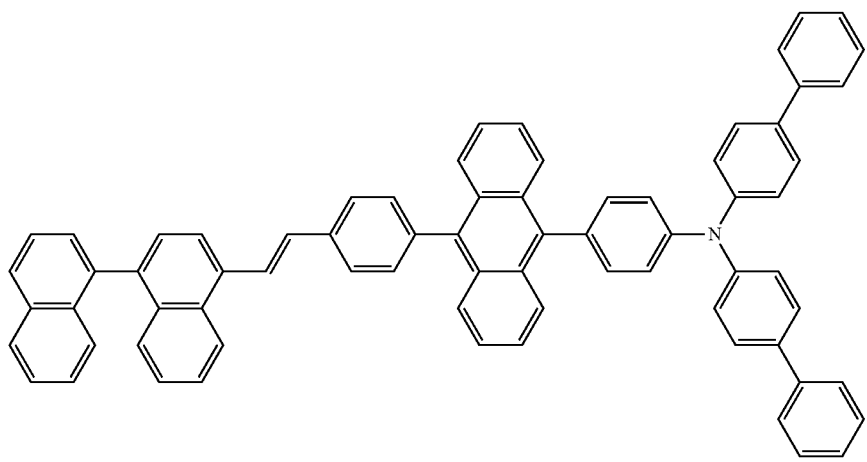
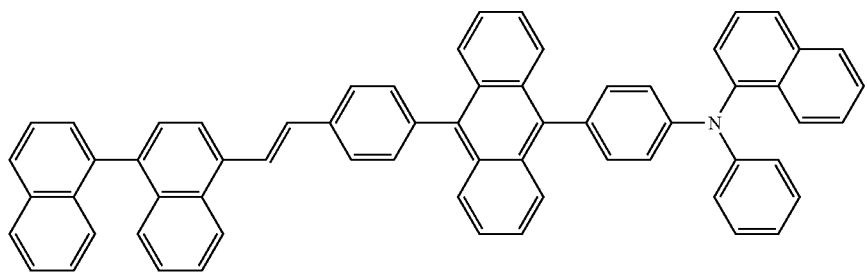

-continued
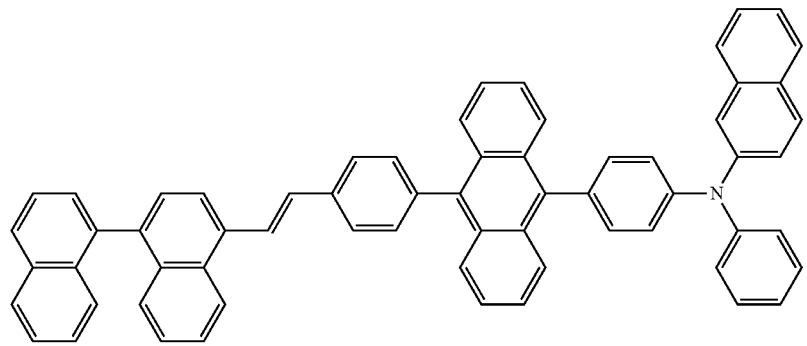
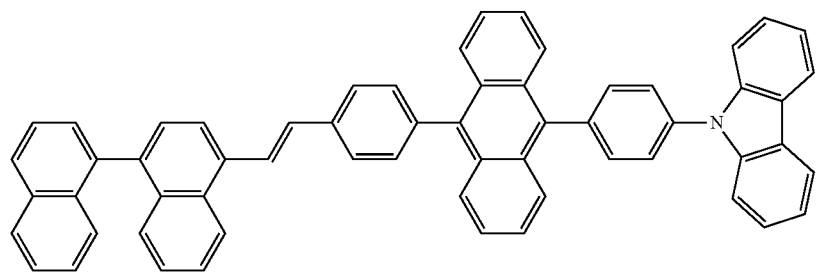
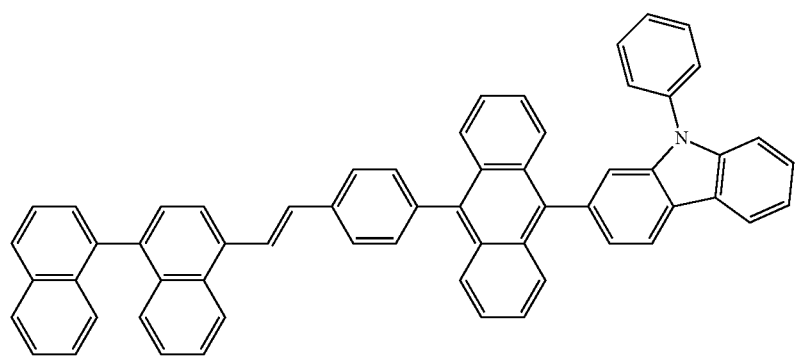
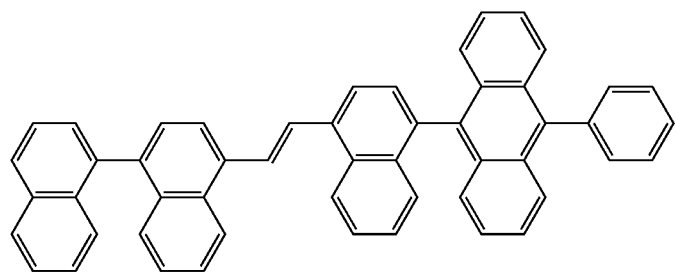
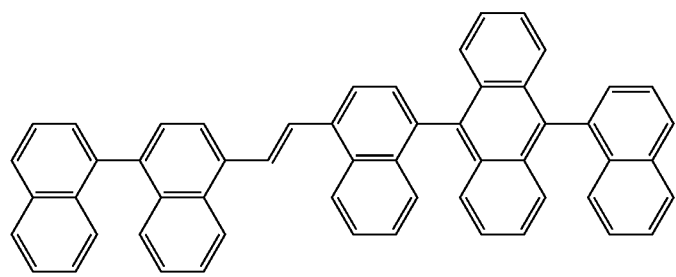

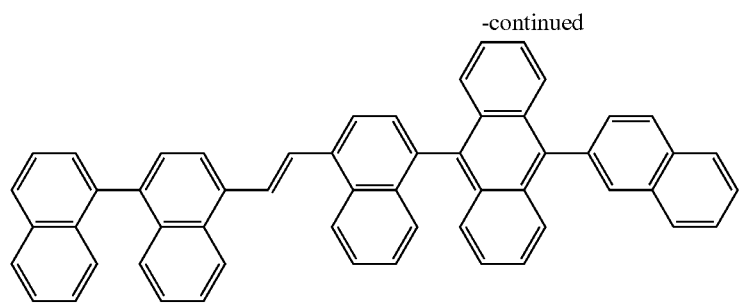
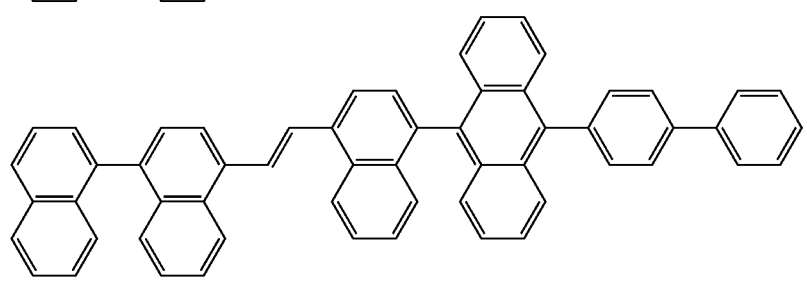
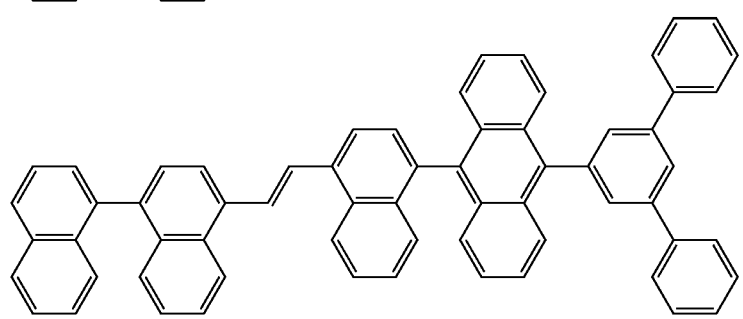
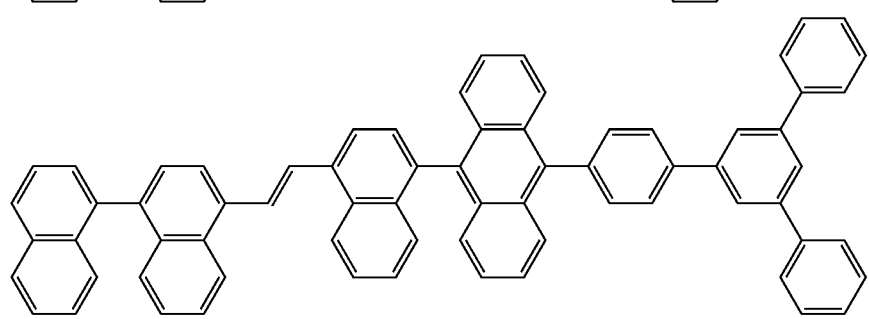
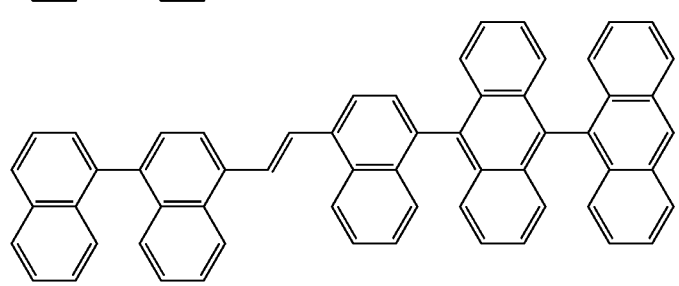
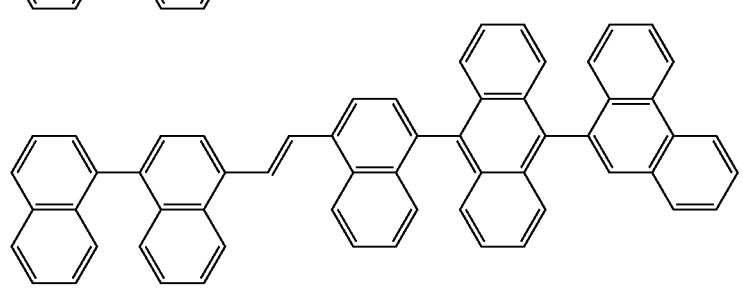

-continued
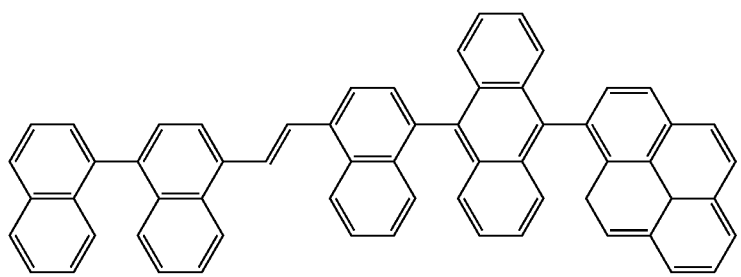
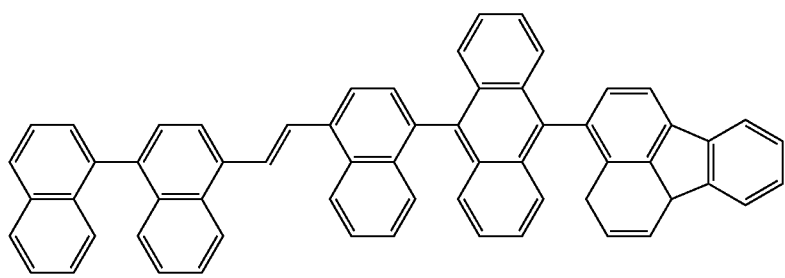
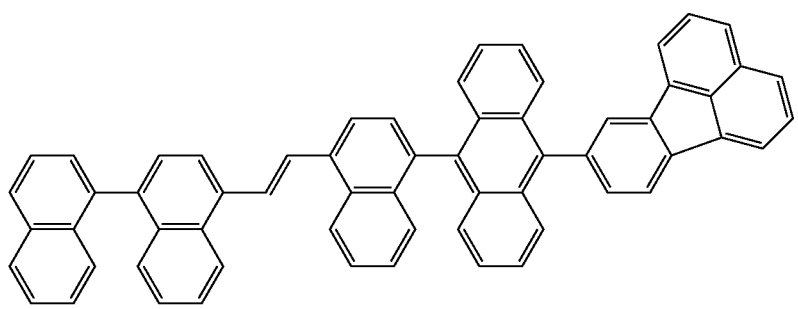
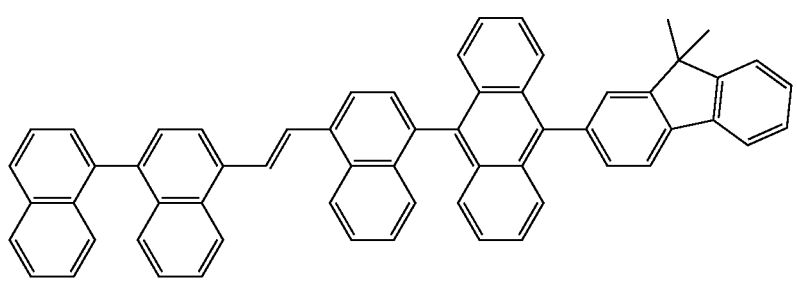
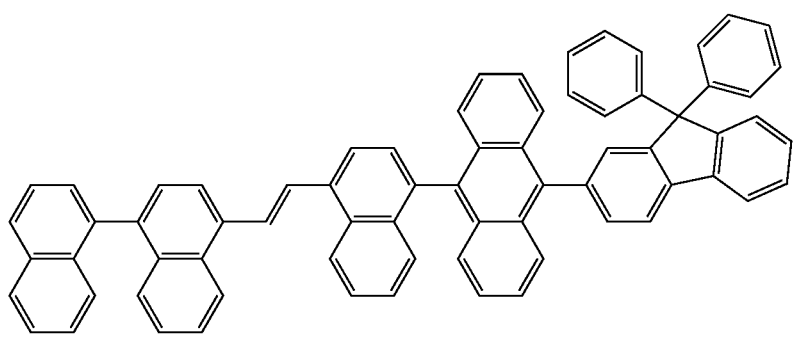

-continued
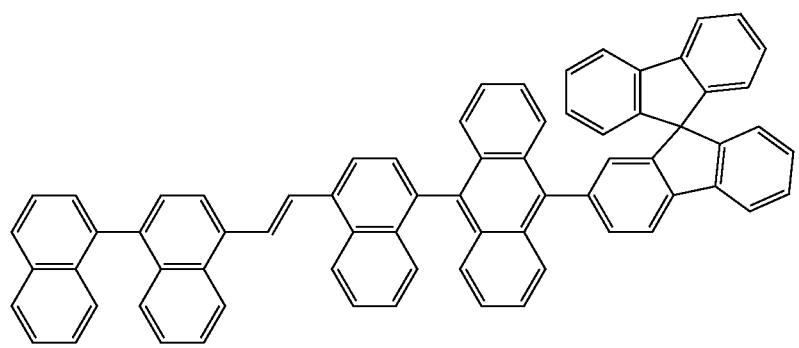
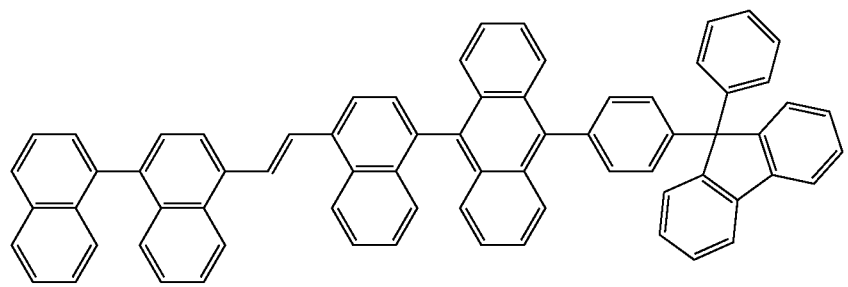
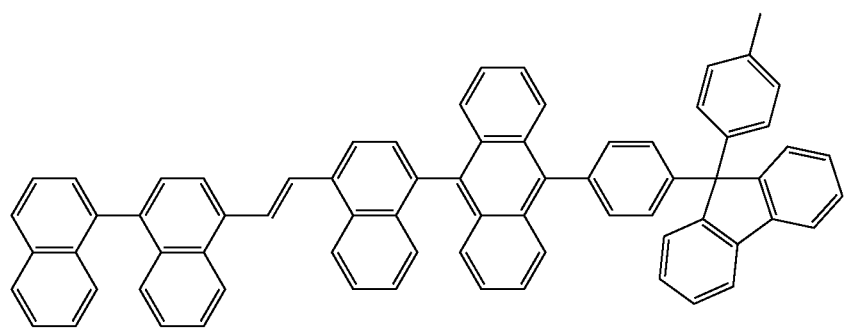
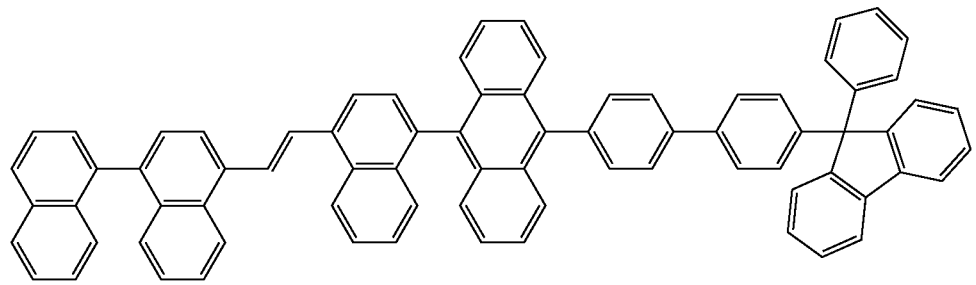
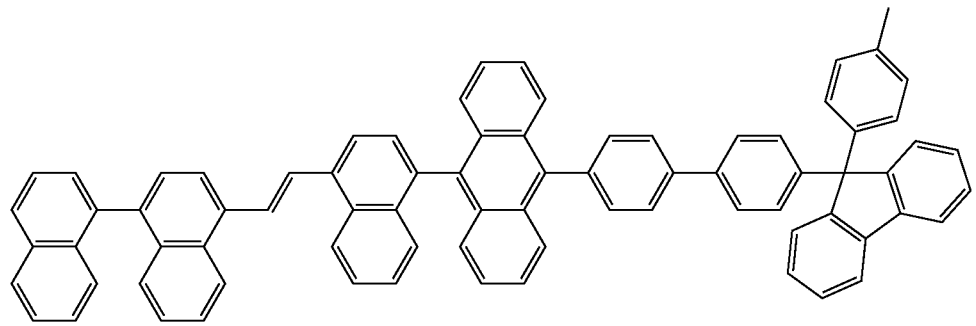

-continued
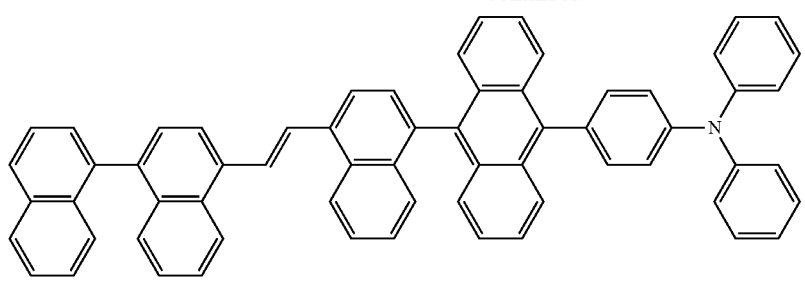
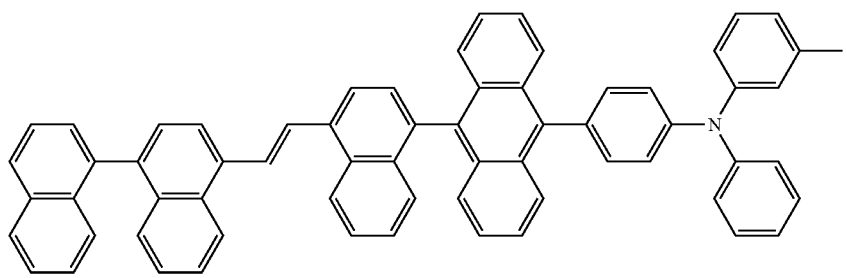
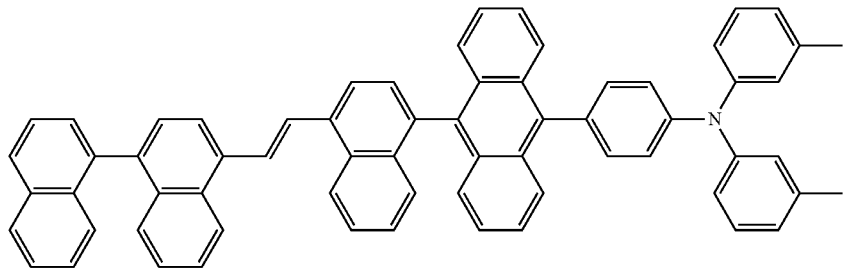
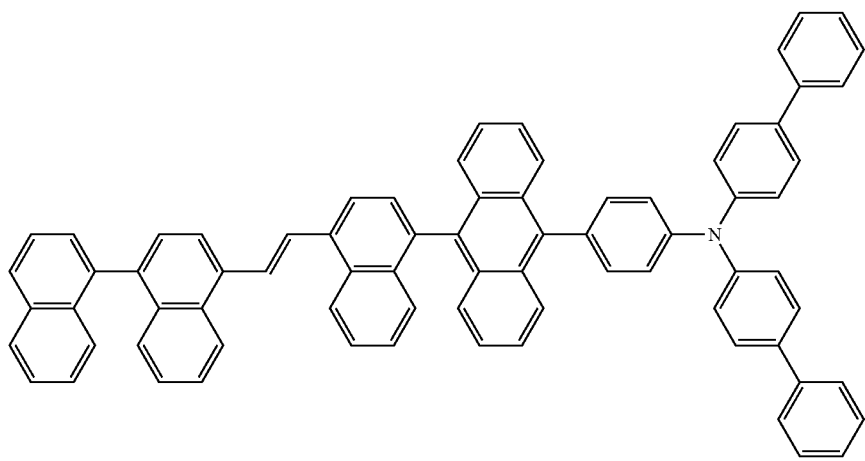
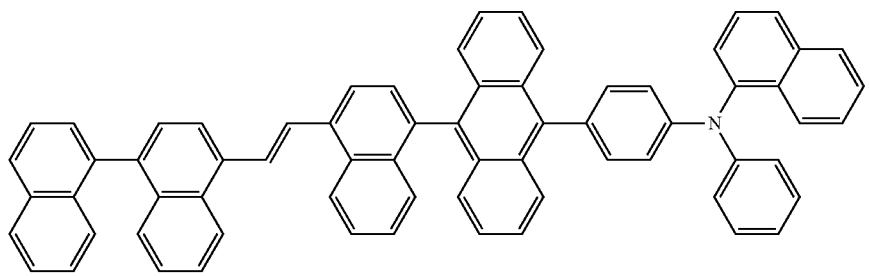

-continued
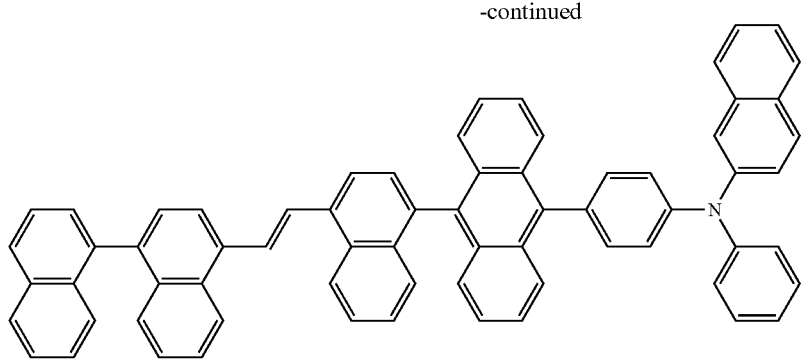
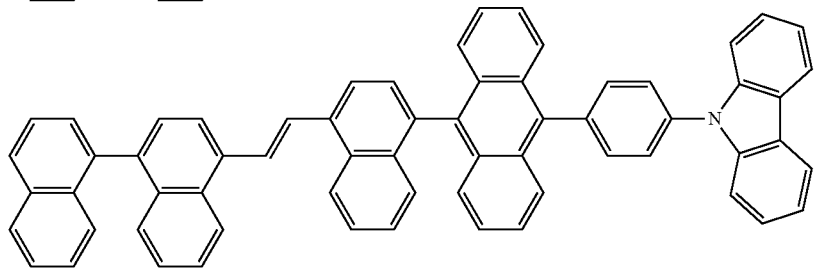
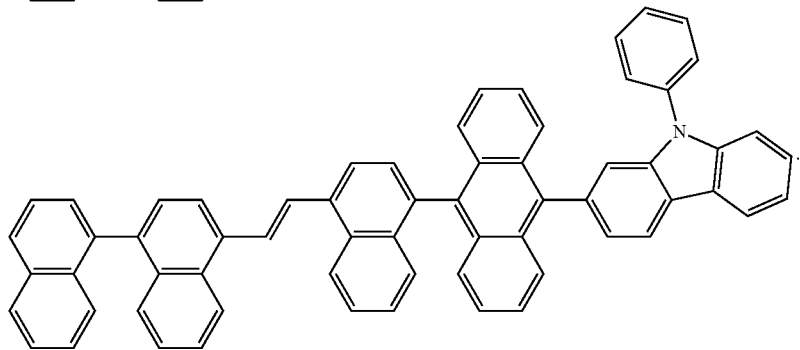
7. The organic electronic material according to claim 6, wherein the structure is one of the following structures:
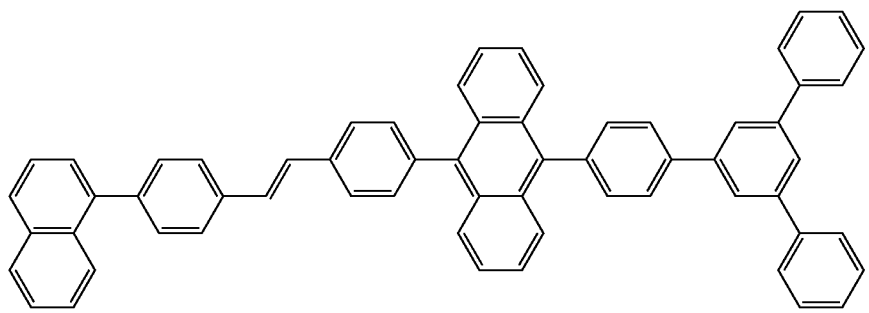
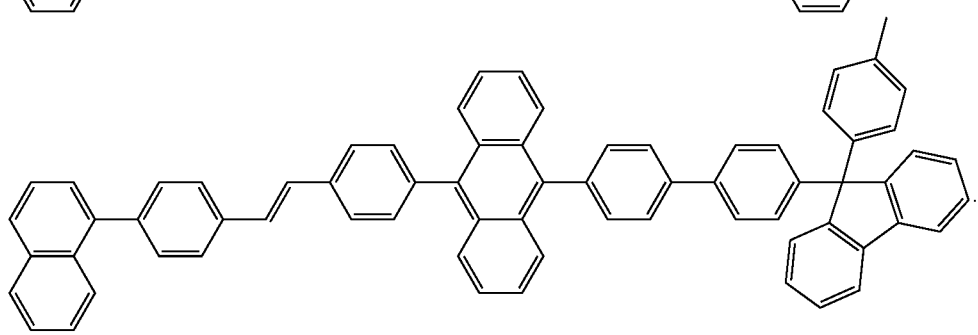

8. The organic electronic material of claim 1, wherein the structure is in an organic light-emitting device, organic solar cell, organic thin-film transistor, or organic photoreceptor.

9. The organic electronic material of claim 2, wherein the structure is in an organic light-emitting device, organic solar cell, organic thin-film transistor, or organic photoreceptor.

10. The organic electronic material of claim 3, wherein the structure is in an organic light-emitting device, organic solar cell, organic thin-film transistor, or organic photoreceptor.

11. The organic electronic material of claim 4, wherein the structure is in an organic light-emitting device, organic solar cell, organic thin-film transistor, or organic photoreceptor.

12. The organic electronic material of claim 5, wherein the structure is in an organic light-emitting device, organic solar cell, organic thin-film transistor, or organic photoreceptor.

13. The organic electronic material of claim 6, wherein the structure is in an organic light-emitting device, organic solar cell, organic thin-film transistor, or organic photoreceptor.

14. The organic electronic material of claim 7, wherein the structure is in an organic light-emitting device, organic solar cell, organic thin-film transistor, or organic photoreceptor.

* * * * *